(12) United States Patent
Caruso et al.

(10) Patent No.: US 8,614,220 B2
(45) Date of Patent: Dec. 24, 2013

(54) SUBSTITUTED PYRAZOLO-QUINAZOLINE DERIVATIVES, PROCESS FOR THEIR PREPARATION AND THEIR USE AS KINASE INHIBITORS

(75) Inventors: Michele Caruso, Milan (IT); Italo Beria, Milan (IT); Maria Gabriella Brasca, Milan (IT); Ron Ferguson, Milan (IT); Helena Posteri, Varese (IT); Barbara Valsasina, Milan (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 871 days.

(21) Appl. No.: 12/520,842

(22) PCT Filed: Dec. 17, 2007

(86) PCT No.: PCT/EP2007/064096
§ 371 (c)(1),
(2), (4) Date: Mar. 10, 2010

(87) PCT Pub. No.: WO2008/074788
PCT Pub. Date: Jun. 26, 2008

(65) Prior Publication Data
US 2010/0216808 A1    Aug. 26, 2010

(30) Foreign Application Priority Data

Dec. 21, 2006 (EP) .................................. 06126902
Oct. 8, 2007 (EP) .................................. 07118039

(51) Int. Cl.
*A61K 31/519*    (2006.01)
*C07D 239/70*    (2006.01)

(52) U.S. Cl.
USPC .......................................... 514/267; 544/251

(58) Field of Classification Search
USPC .................... 514/252.17, 267; 544/251, 395
See application file for complete search history.

(56) References Cited

FOREIGN PATENT DOCUMENTS

| EP | 0 533 267 A1 | 3/1993 |
|---|---|---|
| WO | WO 03/070706 A1 | 8/2003 |
| WO | WO 2004/073634 A2 | 9/2004 |
| WO | WO 2004/104007 A1 | 12/2004 |
| WO | WO 2008/018426 A1 | 2/2008 |

OTHER PUBLICATIONS

Vippagunta et al., Crystalline solids, 2001, Advanced Drug Delivery Reviews, 48, pp. 3 and 18.*
Wolff et al., Burger's Medicinal Chemistry and Drug Discovery, 1994, Wiley-Interscience, Fifth Edition, vol. I: Principles and Practice, pp. 975-977.*
Kwon et al., Handbook of Essential Pharmacokinetics, Pharmacodynamics and Drug Metabolism for Industrial Scientists, 2001, http://www.myilibrary.com/Browse/open.asp?ID=4284&loc=1, Retrieved from the Internet Jun. 16, 2008, p. 213.*
Metabolomics [online], Retrieved from the Internet Jun. 16, 2008, URL: http://www.en.wikipedia.org/wiki/Metabolomics, p. 1.*
Cancer [online], [retrieved on Jun. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Shimma N. et al., "Preparation of 2-(Morpholin-4-yl)-6,7-Dihytiropyrrolo[2,3-5,6,7,8-Tetrahydropyrido[2,3-d]Pyrimidine as Phosphatidylinositol 3-Kinase (P13K) Inhibitors", STN Database Accession No. 2008:192498 Abstract (2008).

* cited by examiner

*Primary Examiner* — Noble Jarrell
(74) *Attorney, Agent, or Firm* — Scully, Scott, Murphy & Presser, P.C.

(57) ABSTRACT

Pyrazolo-quinazoline derivatives of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

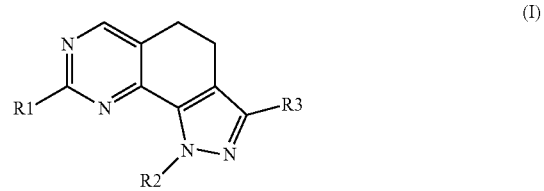

16 Claims, No Drawings

SEQUENCE LISTING

<160> NUMBER OF SEQ ID NOS: 2

<210> SEQ ID NO 1
<211> LENGTH: 82
<212> TYPE: DNA
<213> ORGANISM: Artificial
<220> FEATURE:
<223> OTHER INFORMATION: Forward primer

<400> SEQUENCE: 1

```
ggggacaagt ttgtacaaaa aagcaggctt attcgaaaac ctgtattttc agggccctag    60
tgctgcagtg actgcaggga ag                                            82
```

<210> SEQ ID NO 2
<211> LENGTH: 60
<212> TYPE: DNA
<213> ORGANISM: Artificial
<220> FEATURE:
<223> OTHER INFORMATION: reverse primer

<400> SEQUENCE: 2

```
ggggaccact ttgtacaaga aagctgggtt tcactattta ttgaggactg tgaggggctt    60
```

SUBSTITUTED PYRAZOLO-QUINAZOLINE DERIVATIVES, PROCESS FOR THEIR PREPARATION AND THEIR USE AS KINASE INHIBITORS

The present invention relates to certain substituted pyrazolo-quinazoline compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types. Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle. These checkpoints often go away during oncogenic transformation and this permits cancer cells to tolerate anueploidy and chromosomal instability Inhibition of mitosis in "checkpoint compromised" tumour cells should have catastrophic consequences as cancer cells try to carry forward an aberrant mitosis.

The Polo-like kinase family, comprising 4 serine/threonine kinases (Plk-1-4), are predominantly involved in the entry into, progression through and exit from mitosis. These kinases are characterized by having an n-terminal kinase domain and a unique, c-terminal, "Polo-Box" domain. This domain is responsible for targeting the kinase to various mitotic structures (centrosomes, kinetochores, spindle poles, midbody) and the temporal and spatial regulation of Plks are important for normal progression through mitosis (reviewed in van Vugt and Medema, Oncogene 2005, 24(17):2844-59; Barr et al, Nat Rev Mol Cell Biol. 2004, 5(6):429-40; Dai and Cogswell, Prog Cell Cycle Res. 2003, 5:327-34; Glover et al, Genes Dev. 1998, 12(24):3777-87). The most characterized member of the family is Plk-1 and its activity has been implicated in several processes during mitosis including the G2/M transition by regulating Cdk-1 activity in multiple ways (activation of Cdc25c, nuclear translocation of cyclin B, inactivation of Myt-1 and Wee-1) (Inoue et al, EMBO J. 2005, 24(5): 1057-67; van Vugt et al, J Biol Chem. 2004, 9(35):36841-54; Watanabe et al, Proc Natl Acad Sci USA. 2004, 101(13): 4419-24 2004; Nakajima et al, J Biol Chem. 2003, 278(28): 25277-80; Toyoshima-Morimoto et al, J Biol Chem. 2002, 277(50):48884-8; Bartholomew et al, Mol Cell Biol., 2001 21(15):4949-59; Qian et al, Mol Biol Cell. 2001, 12(6):1791-9; Roshak et al, Cell Signal. 2000, 12(6):405-11); centrosome maturation and separation; regulation of chromosomal-arm cohesion at prophase and sister chromatid separation at metaphase/anaphase transition; activation of the Anaphase Promoting Complex to start mitotic exit; cytokinesis. Plk-1 is over-expressed in several tumour cells including breast, ovarian, non small cell lung, colon, head and neck, endometrial and esophageal carcinomas and its over-expression often correlates with poor prognosis.

Disruption of Plk-1 function by various means in tumoural cells (siRNA and antisense ablation, dominant negative proteins and immunodepletion) results in an aberrant mitosis followed by mitotic catastrophy whilst causing a "checkpoint-mediated" cell cycle arrest in normal cells. Thus, pharmacological attenuation of Plk-1 function may have a therapeutic benefit in the treatment of several diverse cancers.

SUMMARY OF THE INVENTION

Fused bicyclic pyrimidine derivatives for the treatment of hyperproliferative diseases are disclosed in WO 96/40042 in the name of Pfizer Inc.

Fused polycyclic pyrimidine derivatives as protein kinase inhibitors are also disclosed in WO 98/58926 and WO 98/28281, both in the name of Celltech Therapeutics Ltd. Fused tricyclic pyrazole compounds known in the art as protein kinase inhibitors are disclosed in WO 03/070236 and WO 03/070706, in the name of Pharmacia Italia S.P.A. and Pharmacia Corp. respectively.

Pyrazolo-quinazoline derivatives possessing kinase inhibitory activity have been also disclosed in WO 04/104007, in the name of the applicant itself. Some specific compounds of the aforementioned WO 04/104007 are excluded from the present general formula.

Despite these developments, there is still need for effective agents for said diseases. The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted pyrazolo-quinazoline compound represented by formula (I):

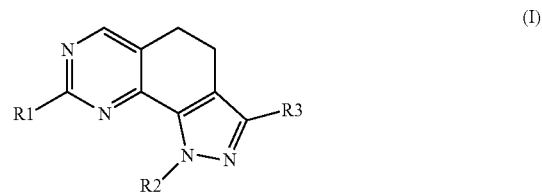

wherein
R1 is an ortho-substituted-arylamino;
R2 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl and heterocyclyl;
R3 is CO—OR' or CO—NR'R", wherein R' and R" are, each independently, hydrogen or an optionally substituted group selected from straight or branched $C_1$-$C_6$ alkyl, $C_3$-$C_6$ cycloalkyl and heterocyclyl, or R' and R" taken together with the nitrogen atom to which they are bonded, may form an optionally substituted heterocyclyl group optionally containing one additional heteroatom selected among N, O or S, provided that:

ethyl 1-methyl-8-(2-methoxy-phenylamino)-4,5-dihydro-1H-pyrazolo[4,3-h]quinazoline-3-carboxylate and 1-methyl-8-(2-methoxyphenylamino)-4,5-dihydro-1H-pyrazolo[4,3-h]quinazoline-3-carboxamide are excluded;
and isomers, tautomers, hydrates, solvates, complexes, metabolites, prodrugs, carriers, N-oxides and pharmaceutically acceptable salts thereof.

The present invention also provides methods of synthesizing the substituted pyrazolo-quinazoline compounds, represented by formula (I), prepared through a process consisting of standard synthetic transformations.

The present invention also provides a method for treating diseases caused by and/or associated with dysregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, IGF-R, PI3K, wee1 kinase, Src, Abl, Akt, MAPK, ILK, MK-2, IKK-2, Cdc7, Nek, Cdk/cyclin kinase family, more particularly PLK-1 and PLK-3, which comprises administering to a mammal, in need thereof, an effective amount of a substituted pyrazolo-quinazoline compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

DETAILED DESCRIPTION OF THE INVENTION

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In the present description, unless otherwise specified, with the term "ortho-substituted-arylamino", which represents R1, we intend any aryl group linked to the rest of the molecule through the —(NH)— moiety, said arylamino being substituted in ortho position, and also optionally substituted in other free positions.

With the term "aryl" we intend carbocyclic or heterocyclic groups containing from 1 to 2 ring moieties, either fused or linked to each other by single bonds, wherein at least one of the rings is aromatic; if present, any aromatic heterocyclic ring also referred to as heteroaryl group, comprises a 5 to 6 membered ring containing from 1 to 3 heteroatoms selected among N, NH, O or S. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

With the term "$C_3$-$C_6$ cycloalkyl" we intend, unless otherwise provided, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

According to the present invention and unless otherwise provided, any of the above $R_1$, $R_2$, $R_3$, R', and R" group may be optionally substituted, in any of their free positions, by one or more groups, for instance 1 to 6 groups, independently selected from: halogen, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term halogen atom we intend a fluorine, chlorine, bromine or iodine atom.

With the term cyano we intend a —CN residue.

With the term nitro we intend a —NO$_2$ group.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above $C_1$-$C_6$ alkyl, aryl or heterocyclyl groups linked to the rest of the molecule through a oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_6$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:

R3 is CO—OH or CO—NR'R", wherein R' and R" are as defined above.

Another preferred class of compounds of formula (I) are the compounds wherein:

R1 is an ortho-substituted-arylamino of the formula:

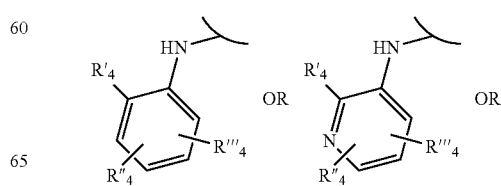

-continued

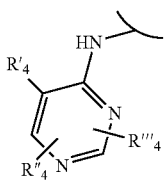

wherein R'$_4$, R"$_4$ and R'''$_4$ are independently selected from a group consisting of: halogen, nitro, cyano, C$_1$-C$_6$ alkyl, polyfluorinated alkyl, polyfluorinated alkoxy, alkenyl, alkynyl, hydroxyalkyl, aryl, arylalkyl, heterocyclyl, C$_3$-C$_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylamino carbonyl, heterocyclylamino carbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

A further preferred class of compounds of formula (I) are the compounds wherein:
R1 is an ortho-substituted-arylamino of the formula:

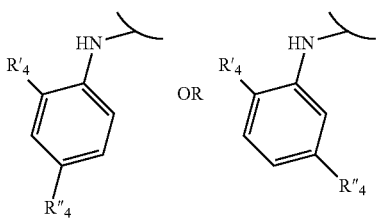

wherein R'$_4$ and R"$_4$ are as above defined and
R2 is an optionally substituted straight or branched C$_1$-C$_6$ alkyl or C$_2$-C$_6$ alkenyl.

A particularly preferred class of compounds of formula (I) are the compounds wherein:
R3 is CO—NR'R", wherein R' and R" are as above defined.

Preferred specific compounds of formula (I) are the compounds listed below (for the meaning of the codes, see Examples section):

1) 1-Methyl-8-(2-methylphenylamino)-4,5-dihydro-1H-pyrazolo[4,3-h]quinazoline-3-carboxamide (A4B1C1Z);
2) 1-Methyl-8-(2-methylamino-phenylamino)-4,5-dihydro-1H-pyrazolo[4,3-h]quinazoline-3-carboxamide (A27B1C1Z);
3) 8-(2-Acetyl-phenylamino)-1-(2-fluoro-ethyl)-4,5-dihydro-1H-pyrazolo[4,3-h]quinazoline-3-carboxamide (A2B2C1Z);
4) 8-[2-Acetyl-5-(4-methyl-piperazin-1-yl)-phenylamino]-1-methyl-4,5-dihydro-1H-pyrazolo[4,3-h]quinazoline-3-carboxamide (A39B1C1Z);
5) 8-[2-Acetyl-5-(4-methyl-piperazin-1-yl)-phenylamino]-1-(2-fluoro-ethyl)-4,5-dihydro-1H-pyrazolo[4,3-h]quinazoline-3-carboxamide (A39B2C1Z);
6) 1-Methyl-8-(2-trifluoromethoxy-phenylamino)-4,5-dihydro-1H-pyrazolo[4,3-h]quinazoline-3-carboxamide (A45B1C1Z);
7) 1-Methyl-8-[5-(4-methyl-piperazin-1-yl)-2-trifluoromethoxy-phenylamino]-4,5-dihydro-1H-pyrazolo[4,3-h]quinazoline-3-carboxamide (A51B1C1Z);
8) Ethyl 1-methyl-8-[5-(4-methyl-piperazin-1-yl)-2-trifluoromethoxy-phenylamino]-4,5-dihydro-1H-pyrazolo[4,3-h]quinazoline-3-carboxylate (A51B1C2Z);
9) 1-Methyl-8-[2-methoxy-5-(4-methyl-piperazin-1-yl)-phenylamino]-1-methyl-4,5-dihydro-1H-pyrazolo[4,3-h]quinazoline-3-carboxamide (A85B1C1Z);
10) 8-[5-(4-Methyl-piperazin-1-yl)-2-trifluoromethoxy-phenylamino]-1-(2-fluoro-ethyl)-4,5-dihydro-1H-pyrazolo[4,3-h]quinazoline-3-carboxamide (A51B2C1Z);
11) 1-Methyl-8-[4-(4-methyl-piperazin-1-yl)-2-trifluoromethoxy-phenylamino]-4,5-dihydro-1H-pyrazolo[4,3-h]quinazoline-3-carboxamide (A48B1C1Z);
12) 1-Methyl-8-(2-trifluoromethoxy-5-piperazin-1-yl-phenylamino]-4,5-dihydro-1H-pyrazolo[4,3-h]quinazoline-3-carboxamide (A97B1C1Z);
13) 1-Methyl-8-[2-methyl-5-(4-methyl-piperazin-1-yl)-phenylamino]-4,5-dihydro-1H-pyrazolo[4,3-h]quinazoline-3-carboxamide (A98B1C1Z);
14) 1-Methyl-8-[5-(4-pyrrolidin-1-yl-piperidin-1-yl)-2-trifluoromethoxy phenylamino]-4,5-dihydro-1H-1H-pyrazolo[4,3-h]quinazoline-3-carboxamide (A99B1C1Z);
15) 1-Methyl-8-[5-(4-methyl-piperazin-1-yl)-2-trifluoromethoxy-phenylamino]-4,5-dihydro-1H-pyrazolo[4,3-h]quinazoline-3-carboxylic acid methylamide (A51B1C4Z);
16) 1-Methyl-8-[5-(4-methyl-piperazin-1-yl)-2-methoxy-phenylamino]-4,5-dihydro-1H-pyrazolo[4,3-h]quinazoline-3-carboxylic acid methylamide (A85B1C4Z);
17) 1-Methyl-8-[2-methyl-5-(4-methyl-piperazine-1-carbonyl)-phenylamino]-4,5-dihydro-1H-pyrazolo[4,3-h]quinazoline-3-carboxamide (A87B1C1Z);
18) 1-Methyl-8-[2-methyl-4-(4-methyl-piperazine-1-carbonyl)-phenylamino]-4,5-dihydro-1H-pyrazolo[4,3-h]quinazoline-3-carboxamide (A86B1C1Z);
19) 1-Methyl-8-{2-trifluoromethoxy-5-[(1-methyl-piperidine-4-carbonyl)-amino]-phenylamino}-4,5-dihydro-1H-pyrazolo[4,3-h]quinazoline-3-carboxamide (A82B1C1Z);
20) Ethyl 1-methyl-8-(2-trifluoromethoxy-phenylamino)-4,5-dihydro-1H-pyrazolo[4,3-h]quinazoline-3-carboxylate (A45B1C2Z);
21) Potassium 8-[5-(4-methyl-piperazin-1-yl)-2-trifluoromethoxy-phenylamino]-1-methyl-4,5-dihydro-1H-pyrazolo[4,3-h]quinazoline-3-carboxylate (A51B1C3Z);
22) Potassium 8-(2-trifluoromethoxy-phenylamino)-4,5-dihydro-1H-pyrazolo[4,3-h]quinazoline-3-carboxylate (A45B8C3Z);
23) 1-(2-Hydroxy-ethyl)-8-(2-trifluoromethoxy-phenylamino)-4,5-dihydro-1H-pyrazolo[4,3-h]quinazoline-3-carboxamide (A45B5C1Z);
24) 1-Ethyl-8-[5-(4-methyl-piperazin-1-yl)-2-trifluoromethoxy-phenylamino]-4,5-dihydro-1H-pyrazolo[4,3-h]quinazoline-3-carboxamide (A51B7C1Z);
25) 1-Methyl-8-[5-(4-methyl-piperazin-1-yl)-2-trifluoromethoxy-phenylamino]-4,5-dihydro-1H-pyrazolo[4,3-h]quinazoline-3-carboxylic acid (2,2,2-trifluoro-ethyl)-amide (A51B1C7Z);

26) 1-(2-Hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B5C1Z);
27) 8-[5-(4-methyl-piperazin-1-yl)-2-trifluoromethoxy-phenylamino]-1-vinyl-4,5-dihydro-1H-pyrazolo[4,3-h]quinazoline-3-carboxamide (A51B10C1Z);
28) 1-(2-Chloro-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B9C1Z);
29) 8-[5-(4-Methyl-piperazin-1-yl)-2-trifluoromethoxy-phenylamino]-4,5-dihydro-1H-pyrazolo[4,3-h]quinazoline-3-carboxamide (A51B8C1Z);
30) Potassium 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (A51B5C3Z);
31) Ethyl 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (A51B5C2Z);
32) 1-Methyl-8-[5-(1-methyl-1,2,3,6-tetrahydro-pyridin-4-yl)-2-trifluoromethoxy-phenylamino]-4,5-dihydro-1H-pyrazolo[4,3-h]quinazoline-3-carboxamide (A113B1C1Z);
33) 1-Methyl-8-[5-(1-methyl-piperidin-4-yl)-2-trifluoromethoxy-phenylamino]-4,5-dihydro-1H-pyrazolo[4,3-h]quinazoline-3-carboxamide (A114B1C1Z);
34) 8-(5-Bromo-2-trifluoromethoxy-phenylamino)-1-methyl-4,5-dihydro-1H-pyrazolo[4,3-h]quinazoline-3-carboxamide (A49B1C1Z), and
35) 8-(5-Bromo-2-trifluoromethoxy-phenylamino)-4,5-dihydro-1H-pyrazolo[4,3-h]quinazoline-3-carboxamide (A49B8C1Z).

For a reference to any specific compound of formula (I) of the invention, optionally in the form of a pharmaceutically acceptable salt, see the experimental section and claims.

The present inventions also provides a process for the preparation of compounds of formula (I) as defined above, characterized in that the process comprises:
st.1) reacting the compound of formula (II):

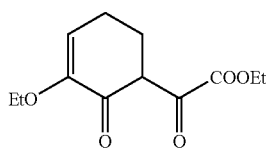

(II)

with a hydrazine derivative of formula (III):

R2-NHNH$_2$ (III)

wherein R2 is as defined above, in the presence of acetic acid to give a compound of formula (IV):

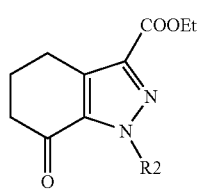

(IV)

wherein R2 is as defined above; or alkylating a compound of formula (IV) wherein R2 is hydrogen with a compounds of formula (V):

R2-Y (V)

wherein Y is a suitable leaving group such as mesyl, tosyl, halogen, and R2 is as defined above but not hydrogen, to give a compound of formula (IV) wherein R2 is as defined above but not hydrogen;
st.2) reacting the compound of formula (IV) with dimethylformamide-di-tert-butylacetale or dimethylformamide-diisopropylacetale to give a compound of formula (VI):

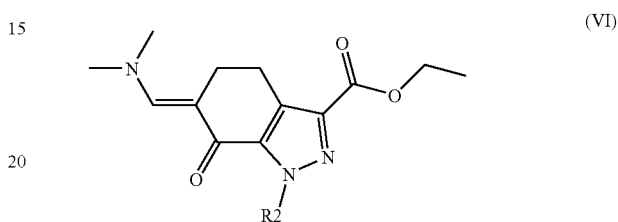

(VI)

wherein R2 is as defined above;
st3.) reacting the compound of formula (VI) according to any one of the alternative steps (st.3a) or (st.3b):
st.3a) with guanidine to give a compound of formula (VII), wherein R2 is as defined above; converting the amino group of the resulting compound of formula (VII) to iodine, and then reacting the resulting iodo-derivative of formula (VIII) with an ortho-substituted-arylamine of formula R1-H (IX) wherein R1 is as defined above, to give a compound of formula (I):

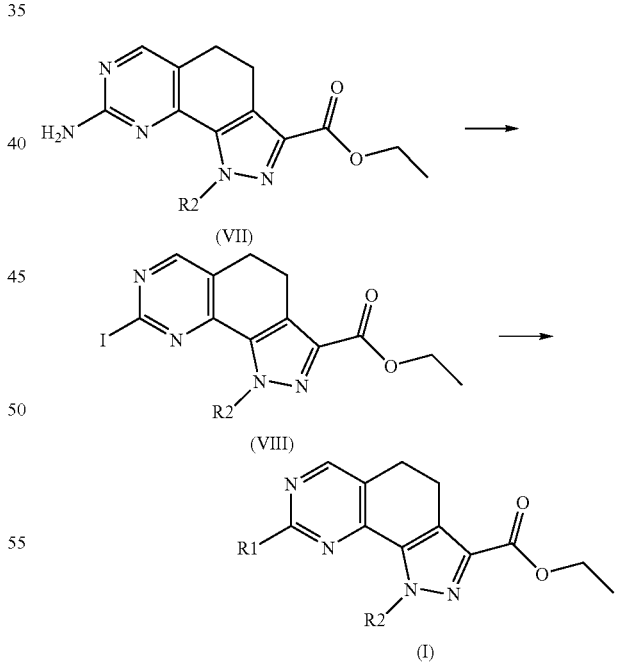

wherein R1 and R2 are as defined above;
st.3b) with a guanidine derivative of formula (X):

R1-C(=NH)NH$_2$ (X)

wherein R1 is as defined above, to give a compound of formula (I)

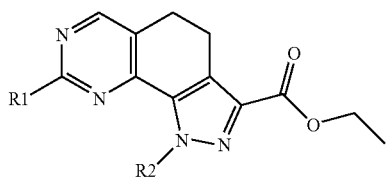

wherein R1 and R2 are as defined above, and
optionally converting it into other derivatives of formula (I) and/or into pharmaceutically acceptable salts thereof.

The present invention further provides a process for the preparation of a compound of formula (I) as defined above, characterized in that the process comprises:

st.4.) converting the ethoxycarbonyl group of the compound of formula (VIII) as defined above, to a compound of formula (XIII) or corresponding salt through acidic or basic hydrolysis; converting the resulting compound of formula (XIII) or corresponding salt into the compound of formula (XIV) through reaction under basic conditions and in presence of a suitable condensing agent, with an amine of formula R'R"-NH (XI) wherein R' and R" are as defined above; reacting the compound of formula (XIV) with an ortho-substituted-arylamine of formula R1-H (IX) wherein R1 is as defined above, to give a compound of formula (I):

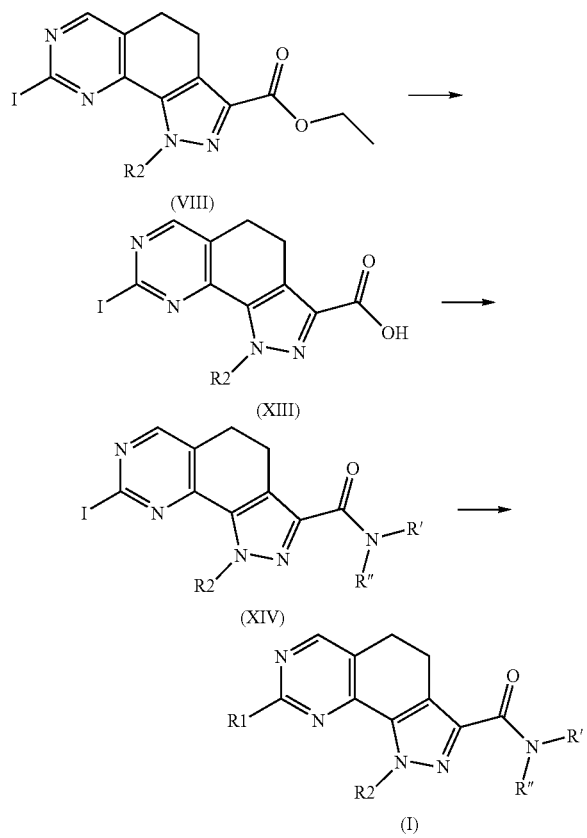

wherein R1 and R2 are as defined above, and
optionally converting it into other derivatives of formula (I) and/or into pharmaceutically acceptable salts thereof.

As defined above, the compounds of formula (I) which are prepared according to the process object of the invention, can be conveniently converted into other compounds of formula (I) by operating according to well-known synthetic conditions, the following being examples of possible conversions:

a) converting a compound of formula (I) wherein R3 is ethoxycarbonyl into a compound of formula (I) wherein R3 is aminocarbonyl by treatment with ammonium hydroxide:

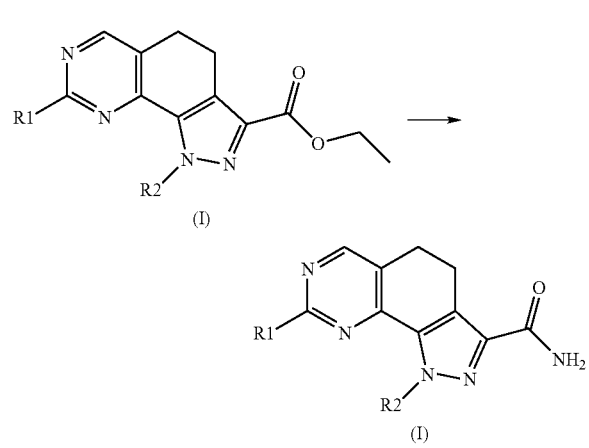

b) converting a compound of formula (I) wherein R3 is ethoxycarbonyl into a compound of formula (I) wherein R3 is a group CO—NR'R" by treatment with an amine of formula R'R"-NH (XI), wherein R' and R" are as defined above:

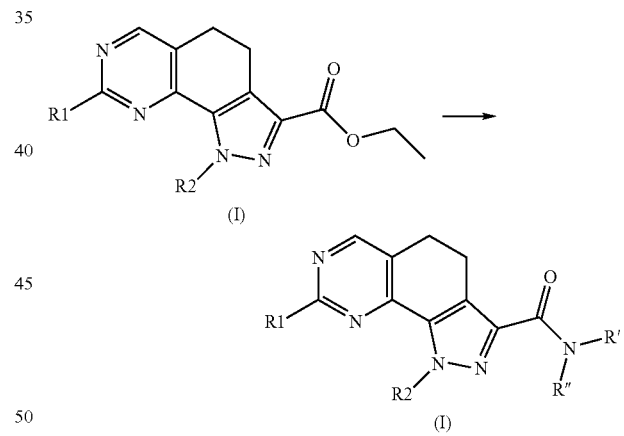

c) converting a compound of formula (I) wherein R3 is ethoxycarbonyl into a compound of formula (I) wherein R3 is a group CO—OH or corresponding salt through acidic or basic hydrolysis:

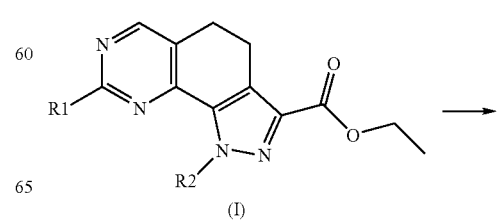

-continued

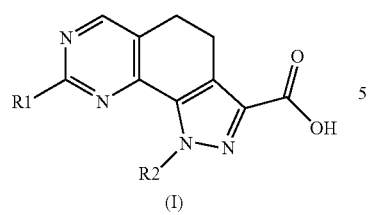

d) converting a compounds of formula (I) wherein R3 is CO—OH or corresponding salt into a compounds of formula (I) wherein R3 is a group CO—NR'R", through reaction with an amine of formula R'R"-NH (XI) under basic conditions and in the presence of a suitable condensing agent, wherein R' and R" are as defined above:

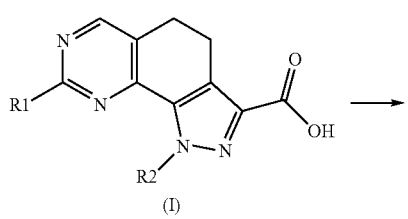

e) converting a compound of formula (I) wherein R2 is Trityl into a compound of formula (I) wherein R2 is hydrogen, under acidic conditions:

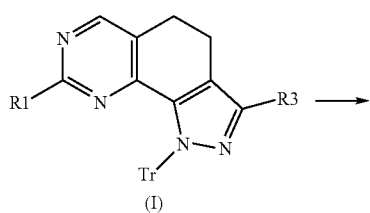

f) converting a compound of formula (I) wherein R2 is hydrogen into a compound of formula (I) wherein R2 is as defined above but not hydrogen, through reaction with an alcohol of formula R2-OH (XII) wherein R2 is as defined above but not hydrogen:

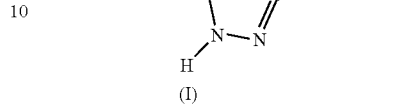

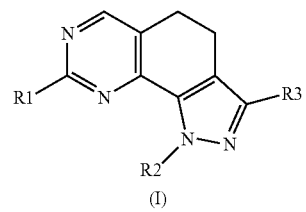

g) converting a compound of formula (I) wherein R2 is hydrogen into a compound of formula (I) wherein R2 is as defined above but not hydrogen, through reaction with a compound of formula R2-X (XV) wherein R2 is as defined above but not hydrogen and X is halogen:

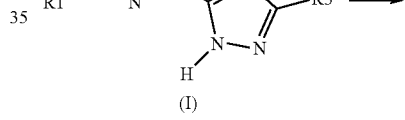

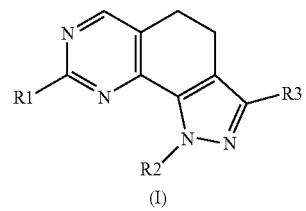

h) converting a compound of formula (I) wherein R2 is an haloethyl into a compound of formula (I) wherein R2 is vinyl:

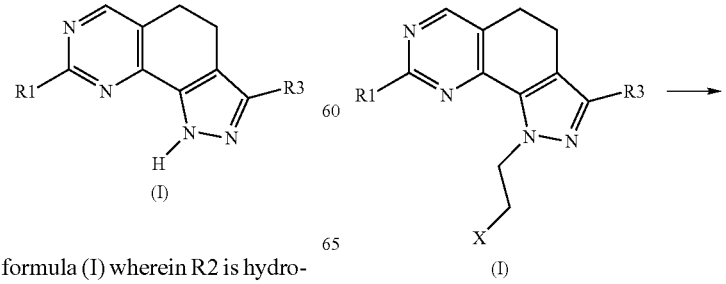

-continued

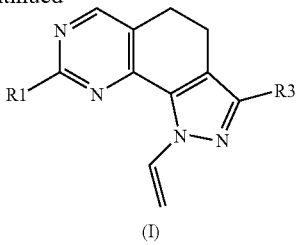

(I)

i) converting a compound of formula (I) wherein R1 is an ortho-substituted-arylamino of the formula:

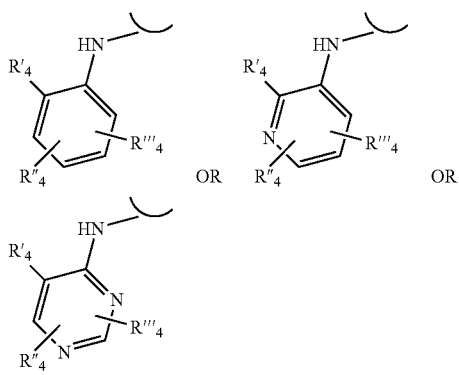

wherein R'$_4$, or R"$_4$ or R'''$_4$ is bromine, into a compound of formula (I) wherein R'$_4$, or R"$_4$ or R'''$_4$ is a group —NR'R" by treatment with an amine of formula R'R"-NH (XI), wherein R' and R" are as defined above.

The above process, in any one of the aforementioned variants, is an analogy process which can be carried out according to well known methods known in the art.

According to step (st.1) of the process, the compound of formula (II) is reacted with the hydrazine derivative of formula (III) in the presence of acetic acid, so as a compound of formula (IV) is obtained. The reaction is preferably carried out at room temperature.

Optionally, the compound of formula (IV) wherein R2 is hydrogen, is reacted with a suitable compound of formula (V) in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so as to obtain compound (IV) wherein R2 is as defined above but not hydrogen.

According to step (st.2) of the process, the compound of formula (IV) is reacted with dimethylformamide-di-tert-butylacetale or dimethylformamide-diisopropylacetale, in the presence of a suitable solvent such as, for instance, dimethylformamide, so as to get the compounds of formula (VI). Preferably, the reaction is carried out at a temperature ranging from room temperature to about 80° C.

According to step (st.3a) of the process, the compound of formula (VI) is reacted with guanidine or guanidine salts as to obtain a compound of formula (VII) through pyrimidine ring formation. Compounds of formula (I) wherein R1 represents an ortho-substituted-arylamino group, can be obtained by the corresponding iodo-derivatives of formula (VIII) which, in their turn, is prepared by the corresponding compounds of formula (VII).

The preparation of the iodo-derivatives of formula (VIII) may be carried out in a suitable solvent such as tetrahydrofuran, diethyl ether or dimethoxyethane, at a temperature ranging from room temperature to about 80° C., and for a time of about 2 to about 48 hours.

The subsequent conversion of the iodo-derivative of formula (VIII) into compounds of formula (I) may be carried out in the presence of an ortho-substituted-arylamine of formula R1-H (IX) in a suitable solvent such as dimethylformamide, dimethoxyethane or acetonitrile and in the presence of catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

According to step (st.3b) of the process, the compound of formula (VI) is reacted with guanidine derivatives of formula (X) so as to obtain the corresponding compound of formula (I) through pyrimidine ring formation. Any of the above reactions are carried out according to conventional methods. As an example, the reactions with guanidine or salts thereof such as hydrochloride, carbonate or nitrate, or with the guanidine derivative of formula (X), as set forth in steps (st.3a) or (st.3b), are carried out in dimethylformamide at a temperature ranging from 80° C. to refluxing temperature eventually in the presence of potassium carbonate.

According to step (st.4) of the process, the compounds of formula (VIII) may be converted into carboxylic acid derivatives of formula (XIII) or corresponding salt through basic or acidic hydrolysis conditions, widely known in the art.

Compounds of formula (XIII) may be converted into carboxamido derivatives of formula (XIV) wherein R' and R" are as defined above. The reaction is carried out in the presence of ammonium chloride or a suitable primary or secondary amine of formula (XI), under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required.

The subsequent conversion of the compound of formula (XIV) to the compound of formula (I) may be carried out in a suitable solvent such as dimethylformamide, dimethoxyethane or acetonitrile and in the presence of an ortho-substituted-arylamine of formula R1-H (IX), catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

As formerly indicated, the compounds of formula (I) previously prepared may be easily converted into several other compounds of formula (I) of the invention.

As an example, compounds of formula (I) bearing R3 as an ethoxycarbonyl group, or even as an alkoxycarbonyl group, can be converted into a variety of derivatives according to methods well-known in the art to convert carboxyester groups (—COOR') into carboxamides (—CONH$_2$), N-substituted carboxamides (—CONHR'), N,N-disubstituted carboxamides (—CONR'R"), and carboxylic acids (—COOH), for instance as defined in conversion (a), (b) and (c).

The operative conditions are those widely known in the art and may comprise, for instance, the conversion of a carboxyester group into a carboxamide group, the reaction with ammonia or ammonium hydroxide in the presence of a suitable solvent such as a lower alcohol, dimethylformamide or mixtures thereof; preferably the reaction is carried out with ammonium hydroxide in a methanol/dimethylformamide mixture, at a temperature ranging from about 50° C. to about 100° C.

Analogous operative conditions apply in the preparation of N-substituted carboxamides or N,N-disubstituted carboxamides wherein a suitable primary or secondary amine is used in place of ammonia or ammonium hydroxide.

Alternatively, carboxyester groups may be converted into carboxamide or N-substituted carboxamides or N,N-disubstituted carboxamides under basic conditions such as lithium bis-trimethylsilylamide 1 N in THF, using ammonium chloride or a suitable primary or secondary amine; preferably the reaction is carried out in tetrahydrofuran at a temperature ranging from 20° C. to reflux.

Likewise, carboxyester groups may be converted into carboxylic acid derivatives through basic or acidic hydrolysis conditions, widely known in the art.

According to conversion (d) of the process, compounds of formula (I) wherein R3 is carboxylic acid (—COOH) may be converted into carboxamido derivatives (—CONR'R") wherein R' and R" are as formerly indicated.

The reaction is carried out in the presence of ammonium chloride or a suitable primary or secondary amine of formula (XI), under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may also be required.

According to conversion(e), the trityl group of the compounds of formula (I) is removed under acidic conditions, for instance with trifluoroacetic acid and in the presence of a suitable solvent such as dichloromethane, so as to give rise to the corresponding compound of formula (I) wherein R2 is hydrogen.

According to conversion (f) of the process, the compounds of formula (I) wherein R2 is hydrogen are reacted with an alcohol of formula R2-OH (XII) wherein R2 is as defined above but not hydrogen, in the presence of di-t-butylazadicarboxylate and triphenylphosphine or triphenylphosphine supported on resin, in a suitable solvent such as, for instance, tetrahydrofurane, so as to obtain the corresponding compounds of formula (I).

According to conversion (g) of the process, the compounds of formula (I) wherein R2 is hydrogen are reacted with a compound of formula R2-X (XV) wherein R2 is as defined above but not hydrogen and X is halogen preferably chlorine, bromine or iodine, in the presence of a base like cesium carbonate in a suitable solvent such, as for instance, dimethylformamide, so as to obtain the corresponding compounds of formula (I).

According to conversion (h) of the process, the compounds of formula (I) wherein R2 is an haloethyl, preferably chloroethyl, are treated with a base, preferably DBU, at a temperature ranging from 20° C. to 80° C., so as to obtain the corresponding compounds of formula (I) wherein R2 is vinyl.

According to conversion (i) of the process, the conversion of a compound of formula (I) wherein R1 is an ortho-substituted-arylamino bearing in any position a bromine, into a compound of formula (I) wherein R1 is an ortho-substituted-arylamino bearing in any position a group —NR'R", can be accomplished in a variety of ways according to conventional methods. Preferably it is carried in a suitable solvent such as tetrahydrofurane or dioxane by treatment with an amine of formula R'R"-NH (XI), and in the presence of catalytic amounts of tris(dibenzilideneacetone)dipalladium, 2-dicyclohexylphosphino-2'-(N,N-dimethylamino)-biphenyl and a base such as $LiN(TMS)_2$ at a temperature ranging from room temperature to reflux and for a time ranging from 1 to about 24 hours.

From all of the above it is clear to the skilled person that any compound of formula (I) bearing a functional group which can be further derivatized to another functional group, by working according to methods well known in the art thus leading to other compounds of formula (I), is intended to be comprised within the scope of the present invention.

According to any variant of the process for preparing the compounds of formula (I), the starting materials and any other reactants are known or easily prepared according to known methods. As an example, whilst the starting material of the compounds of formula (II) is commercially available, the compounds of formula (II) can be prepared as described in the aforementioned WO 04/104007. Compounds of formula (III), (V), (XII) and (XV) are commercially available. Some compounds of formula (IX), (X) and (XI) are commercially available, others were prepared, see following examples 28 to 35 and 43 to 44.

From all of the above, it is clear to the skilled person that when preparing the compounds of formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I), is within the scope of the present invention.

Conventional techniques for racemate resolution include, for instance, partitioned crystallization of diastereoisomeric salt derivatives or preparative chiral HPLC.

In addition, the compounds of formula (I) of the invention may be also prepared according to combinatorial chemistry techniques widely known in the art, for instance by accomplishing the aforementioned reactions between the several intermediates in a parallel and/or serial manner and by working under solid-phase-synthesis (SPS) conditions.

For a general reference to the preparation of the compounds of formula (I) of the invention according to combinatorial chemistry techniques, see the experimental section.

See the experimental section for any specific example concerning the preparation of the compounds of formula (I) of the invention and their conversion into other compounds of formula (I).

Hence, it is a further object of the present invention a library of two or more compounds of formula (I)

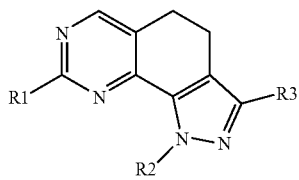

(I)

wherein

R1 is an ortho-substituted-arylamino;

R2 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl and heterocyclyl;

R3 is CO—OR' or CO—NR'R", wherein R' and R" are, each independently, hydrogen or an optionally substituted group selected from straight or branched $C_1$-$C_6$ alkyl, $C_3$-$C_6$ cycloalkyl and heterocyclyl, or R' and R" taken together with the nitrogen atom to which they are bonded, may form an optionally substituted heterocyclyl group optionally containing one additional heteroatom selected among N, O or S, provided that:

ethyl 1-methyl-8-(2-methoxy-phenylamino)-4,5-dihydro-1H-pyrazolo[4,3-h]quinazoline-3-carboxylate and 1-methyl-8-(2-methoxyphenylamino)-4,5-dihydro-1H-pyrazolo[4,3-h]quinazoline-3-carboxamide are excluded;

and isomers, tautomers, hydrates, solvates, complexes, metabolites, prodrugs, carriers, N-oxides and pharmaceutically acceptable salts thereof.

Another object of the present invention is to provide an intermediate of formula (X'):

or of formula (IX'):

wherein R1' is

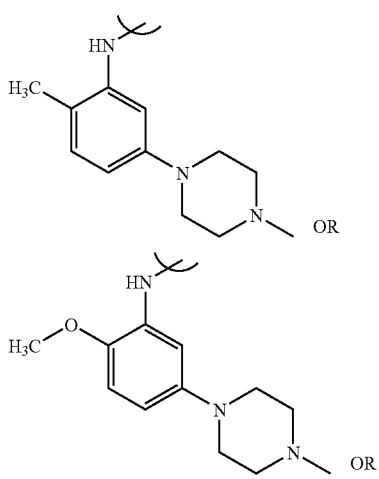

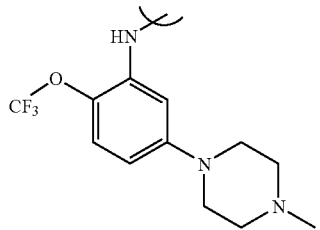

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative PLK-1 inhibitors and the potency of selected compounds was determined through the assay described below.

The short forms and abbreviations used herein have the following meaning:

| | |
|---|---|
| Ci | Curie |
| DMSO | dimethylsulfoxide |
| KDa | kiloDalton |
| microCi | microCurie |
| mg | milligram |
| microg | microgram |
| ng | nanogram |
| L | liter |
| mL | milliliter |
| microL | microliter |
| M | molar |
| mM | millimolar |
| microM | micromolar |
| nM | nanomolar |
| Et | ethyl |

Cloning, Expression and Purification of Recombinant PLK1 Kinase Domain.

PLK1 kinase domain (corresponding to residues 2-345 of the full length sequence, see Swiss-Prot accession number P53350) was PCR amplified from the full-length human PLK1 gene purchased from imaGenes as clone IRATp970A078D.

Amplification was performed using the forward oligonucleotide:

[SEQ ID NO: 1]
5'GGGGACAAGTTTGTACAAAAAAGCAGGCTTATTCGAAAACCTGTATTT

TCAGGGCCCTAGTGCTGCAGTGACTGCAGGGAAG3' and the reverse oligonucleotide:

[SEQ ID NO: 2]
5'GGGGACCACTTTGTACAAGAAAGCTGGGTTTCACTATTTATTGAGGAC

TGTGAGGGGCTT -3'.

For cloning purposes, the oligonucleotides included attB sites in order to obtain an attB-flanked PCR product suitable for cloning using the Gateway® technology (Invitrogen). Furthermore, for purification purposes, forward primer included a TEV® cleavage site (Amersham Biosciences). The resulting PCR product was cloned in the pDONR221 plasmid and then transferred in the baculovirus expression vector pVL1393 (Invitrogen) Gateway®-modified. For expression and purification purposes, a His tag was added N-terminal to the PLK kinase domain. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 48 hours of infection, cells were recovered, pelletted and freezed at −80° C. For purification of recombinant protein, pellet was thawed, resuspended in lysis buffer (PBS, NaCl 150 mM, CHAPS 0.1%, DTT 20 mM, glycerol 10%, protease inhibitors) and lysed by sonication. Lysate was cleared by centrifugation and loaded on a Nichel affinity column. After extensive wash, recombinant protein was cleaved and eluted by incubation with TEV® protease.

Biochemical Assay for Inhibitors of PLK-1 Kinase Activity

The inhibitory activity of putative kinase inhibitors and the potency of selected compounds were determined using a trans-phosphorylation assay.

Specific peptide or protein substrates are trans-phosphorylated by their specific serine-threonine or tyrosine kinase, in the presence of ATP traced with $^{33}P$-γ-ATP, and in the presence of their own optimal buffer and cofactors.

At the end of the phosphorylation reaction, more than 98% cold ATP and radioactive ATP is captured by an excess of the ion exchange dowex resin; the resin then settles down to the bottom of the reaction plate by gravity.

Supernatant, containing the phosphorylated substrate, is subsequently withdrawn and transferred into a counting plate, then evaluated by β-counting.

Reagents/Assay Conditions
i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle, the supernatant is discarded and two volumes of 150 mM sodium formate buffer are added per volume of pellet. The pH is then measured and should be around 3.00. The washed resin is stable for more than one week; the stock resin is kept at 4° C. before use.

ii. Kinase Buffer (KB)

Kinase buffer was composed of 50 mM HEPES pH 7.9 containing 10 mM $MgCl_2$, 1 mM DTT, 3 microM $NaVO_3$, and 0.2 mg/mL BSA, 10 mM β-glycerophosphate.

iii. Assay Conditions

The kinase assay was run with a final enzyme concentration PLK-1 of 3 nM, in presence of 40 microM ATP, 3 nM $^{33}P$-γ-ATP and 85 microM substrate alpha-casein, SIGMA, #C-3240.

Robotized Dowex Assay 1) 3× Enzyme mix (done in Kinase Buffer 3×), 5 microL/well
2) 3× substrate and ATP mix (done in $ddH_2O$), together with $^{33}P$-γ-ATP, 5 microL/well
3) 3× test compounds (diluted into $ddH_2O$-3% DMSO)-5 microL/well Compound Dilution and Assay Scheme is Defined Below.
i. Dilution of Compounds 10 mM stock solutions of test compounds in 100% DMSO were distributed into 96 well 12×8 format microtiter plates.

For % inhibition studies, individual dilution plates at 1 mM, 100 microM and 10 microM are prepared in 100% DMSO, then diluted at a 3× concentration (30, 3 and 0.3 microM) in $ddH_2O$, 3% DMSO. A Multimek 96 (Beckman) is used for dilutions and compound pipetting into the test plates For $IC_{50}$ determination, compounds are received as 1 mM, 100% DMSO solutions, plated into the first column of a microtiter plate (A1 to G1), 100 microL.

A Biomek 2000 (Beckman) is used for serial 1:3 dilutions in water, 3% DMSO, from column A1 to A10 and for all the seven compounds in the plate. In a standard experiment, the highest concentration of all compounds is 30 microM, then diluted in the final test mixture down to 10 microM.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×). At the start of the run, the robot aspirates 5 microL of ATP mix, makes an air gap inside the tips (3 microL) and aspirates 5 microL of PLK1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for $IC_{50}$ determination, for the secondary assays/hit confirmation routines.

Biochemical Assay for Inhibitors of Aurora-2 Kinase Activity

The in vitro kinase inhibition assay was conducted in the same way as described for PLK-1 enzyme.

i. Kinase Buffer (KB) for Aurora-2

The kinase buffer was composed of 50 mM HEPES, pH 7.0, 10 mM $MgCl_2$, 1 mM DTT, 3 microM $NaVO_3$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}P$-γ-ATP, and 8 microM substrate, composed of 4 LRRWSLG repeats.

Inhibition Assay of Cdk2/Cyclin A Activity

Kinase reaction: 1.5 microM histone H1 substrate, 25 microM ATP (0.2 microCi P33γ-ATP), 30 ng of baculovirus co-expressed Cdk2/Cyclin A, 10 microM inhibitor in a final volume of 100 microL buffer (TRIS HCl 10 mM pH 7.5, MgCl$_2$ 10 mM, 7.5 mM DTT) were added to each well of a 96 U bottom well plate. After 10 min at 37° C. incubation, reaction was stopped by 20 microL EDTA 120 mM.

Capture: 100 microL were transferred from each well to MultiScreen plate, to allow substrate binding to phosphocellulose filter. Plates were then washed 3 times with 150 microL/well PBS Ca$^{++}$/Mg$^{++}$ free and filtered by MultiScreen filtration system.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% CO$_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 microL/well reagent solution are added to each wells and after 5 minutes shacking microplates are red by a luminometer. The luminescent signal is proportional to the number of cells present in culture.

Given the above inhibition assays, the compounds of formula (I) of the invention resulted to possess a remarkable PLK inhibitory activity, typically with IC$_{50}$ lower than 0.07 microM.

See, as an example, the following Table A reporting the experimental data of some representative compounds of the invention of formula (I) (for the meanings of the codes, see the Examples section) being tested in biochemical assay as PLK-1 inhibitors and in A2780 cell proliferation assay (IC$_{50}$ microM) in comparison with the closest compound of the prior art, described in the aforementioned WO 04/104007, page 105, Table IX, compound B08-X00-M00(C01)-D03.

TABLE A

| Code | PLK-1 IC$_{50}$ (microM) Biochemical Assay | A2780 IC$_{50}$ (microM) Cell proliferation Assay |
| --- | --- | --- |
| Reference compound | 0.070 | 1.1 |
| A85B1C1Z | 0.010 | 0.010 |
| A97B1C1Z | 0.002 | 0.020 |
| A51B5C1Z | 0.003 | 0.042 |
| A4B1C1Z | 0.014 | 0.80 |
| A51B2C1Z | 0.005 | 0.013 |
| A51B10C1Z | 0.001 | 0.010 |
| A45B2C1Z | 0.026 | 0.50 |
| A98B1C3Z | 0.005 | 1.30 |
| A51B1C1Z | 0.001 | 0.008 |
| A51B1C3Z | 0.010 | 0.086 |
| A51B9C1Z | 0.013 | 0.031 |
| A85B1C4Z | 0.026 | 0.10 |
| A113B1C1Z | 0.008 | 0.036 |
| A101B1C1Z | 0.046 | 0.520 |
| A47B1C1Z | 0.007 | 0.147 |

Surprisingly, the PLK-1 inhibitory activity of the compounds of the present invention resulted to be markedly superior to that of the reference compound.

So far, the novel compounds of the invention are unexpectedly endowed with a PLK-1 inhibitory activity significantly higher than that of the structurally closest prior art compounds of the aforementioned WO 04/104007 and are thus particularly advantageous, in therapy, against proliferative disorders associated with an altered cell cycle dependent kinase activity.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route. For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The synthetic preparation of some compounds of formula (I) of the invention is described in the following examples. All the compounds were conveniently and unambiguously identified through a coding system (see following table IV), some of them were herewith listed and indicated also according to their chemical name whilst others were conveniently and unambiguously identified through a coding system, together with their $^1$H-NMR data or HPLC/Mass data (see following tables V to XX). Each code, which unambiguosly identifies a single specific compound of formula (I), consists of four units A-B—C—Z.

Code A represents any R1 substituent, as per formula (I), being attached to the rest of the molecule to the position 8; each A group is represented through the proper chemical formula in the following table I, also indicating its point of attachment to the rest of the molecule.

Code B represents the R2 group being attached to the rest of the molecule through the pyrazole nitrogen atom, as per formula (I). Each B group is represented through the proper chemical formula in the following table II, also indicating its point of attachment to the rest of the molecule.

Code C represents the R3 group being attached to the rest of the molecule to the position 3, as per formula (I). Each C group is represented through the proper chemical formula in the following table III, also indicating its point of attachment to the rest of the molecule.

Each specific A B and C group is represented and consecutively numbered in the following table I, II and III respectively.

Finally, code Z refers to the central core of the molecule (I). From all of the above it is clear to the skilled person that Z is substituted by R1 (code A), R2 (code B), and R3 (code C), as defined in formula (I), also indicating the positions of the other substituents.

Therefore, the coding system presently used for some compounds of formula (I) can be shortly summarised as follows:

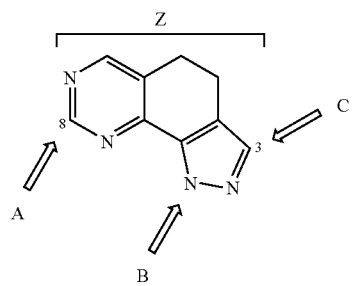

Just as an example, which is not intended to limit the scope of the present invention, the compound A45B8C2Z (see example) represents the pyrazolo-quinazoline derivative of formula (I) wherein the central core is represented by the moiety Z, R1 is the group of formula A45 of table I, R2 is the group of formula B8 of table II, R3 is the group of formula C2 of table III, having formula

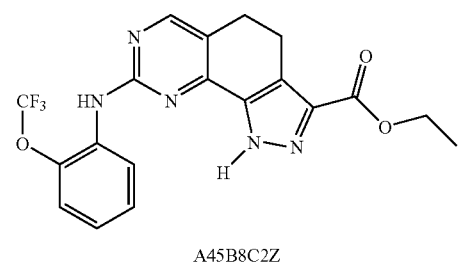 [SMILES: CCOC(=O)c1n[nH]c2c1CCc1cnc(Nc3ccccc3OC(F)(F)F)nc1-2]

A45B8C2Z

TABLE I

| Code | A |
|---|---|
| A1 | 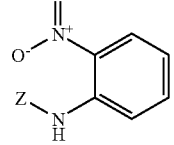 |
| A2 | 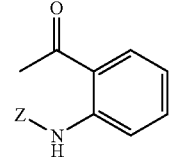 |
| A3 | 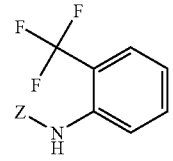 |
| A4 | 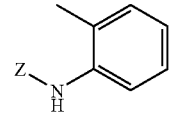 |

TABLE I-continued

| Code | A |
|---|---|
| A5 | 2-fluoroaniline with Z-NH |
| A6 | 2-(hydroxymethyl)aniline with Z-NH |
| A7 | benzene-1,2-diamine (one NH₂, one Z-NH) |
| A8 | 1H-pyrrole-2-carboxamide linked to 2-(Z-NH)aniline |
| A9 | (2-(Z-NH)phenyl)(phenyl)methanone |
| A10 | 2-(Z-NH)biphenyl |
| A11 | 2-(Z-NH)benzonitrile |
| A12 | tert-butyl (2-(Z-NH)phenyl)carbamate |
| A13 | 2-(Z-NH)benzenesulfonamide |
| A14 | N-cyclohexyl-N-methyl-(2-(Z-NH)benzyl)amine |
| A15 | 2-(Z-NH)-N-phenylbenzamide |
| A16 | 4-(2-(Z-NH)phenyl)morpholine |
| A17 | 1-(2-(Z-NH)phenyl)-1H-pyrrole |
| A18 | 1-methyl-4-(2-(Z-NH)phenyl)piperazine |
| A19 | 2-(Z-NH)benzamide |
| A20 | 2-(Z-NH)phenyl phenyl sulfide |
| A21 | N-(2-(Z-NH)phenyl)acetamide |

TABLE I-continued
| Code | A |
|---|---|
| A22 | 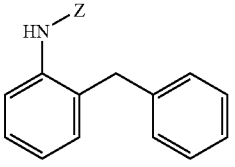 |
| A23 | 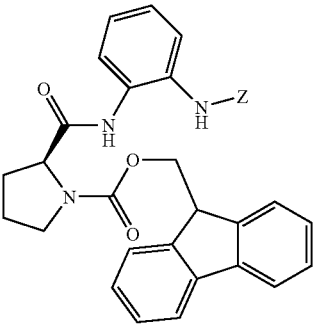 |
| A24 | 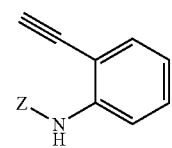 |
| A25 | 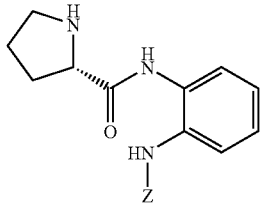 |
| A26 | 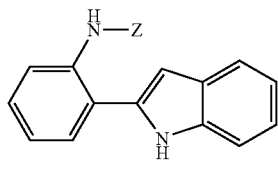 |
| A27 | 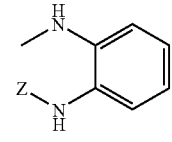 |
| A28 | 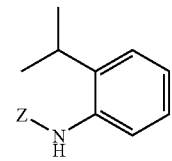 |
| A29 | 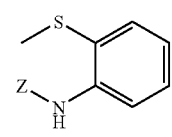 |
| A30 | 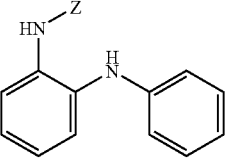 |
| A31 | 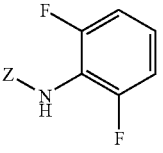 |
| A32 | 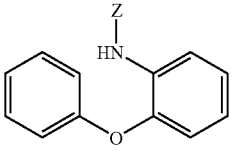 |
| A33 |  |
| A34 | 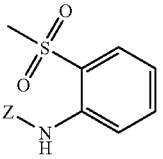 |
| A35 | 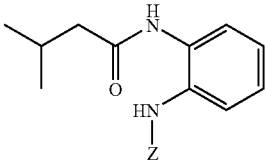 |
| A36 | 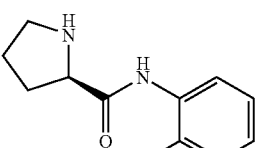 |
| A37 | 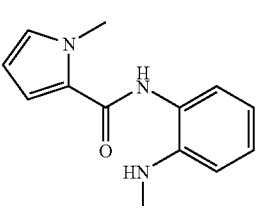 |

TABLE I-continued

| Code | A |
|---|---|
| A38 | 2-(NHZ)-N-(2-aminophenyl)-3,3,3-trifluoropropanamide structure |
| A39 | 4-(4-methylpiperazin-1-yl)-2-(NHZ)-acetophenone structure |
| A40 | 3-(4-methylpiperazin-1-yl)-2-acetyl-NHZ-phenyl structure |
| A41 | N-(1-methylpiperidin-4-yl)-4-(NHZ)-3-(trifluoromethoxy)benzamide structure |
| A42 | 3-methoxy-N-(1-methylpiperidin-4-yl)-4-(NHZ)-benzamide structure |
| A43 | 4-bromo-2-(trifluoromethoxy)-NHZ-aniline structure |
| A44 | 5-nitro-2-(trifluoromethoxy)-NHZ-aniline structure |
| A45 | 2-(trifluoromethoxy)-NHZ-aniline structure |
| A46 | 5-amino-2-(trifluoromethoxy)-NHZ-aniline structure |
| A47 | 4-methoxy-3-(NHZ)-benzyl alcohol structure |
| A48 | 4-(4-methylpiperazin-1-yl)-2-(trifluoromethoxy)-NHZ-aniline structure |
| A49 | 5-bromo-2-(trifluoromethoxy)-NHZ-aniline structure |
| A50 | 4-(trifluoromethoxy)-3-(NHZ)-phenyl prolinamide structure |
| A51 | 4-(4-methylpiperazin-1-yl)-2-(trifluoromethoxy)-NHZ-aniline structure |
| A52 | 2-(thiophen-2-yl)-NHZ-aniline structure |

TABLE I-continued
| Code | A |
|---|---|
| A53 | 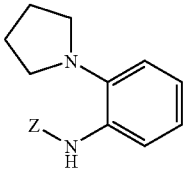 |
| A54 | 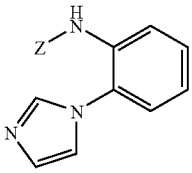 |
| A55 | 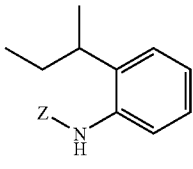 |
| A56 | 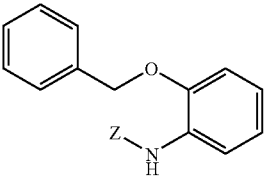 |
| A57 | 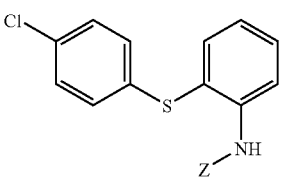 |
| A58 | 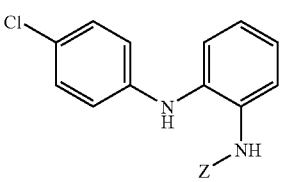 |
| A59 | 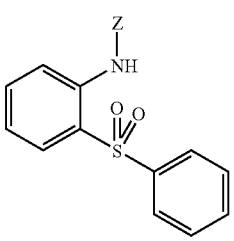 |
| A60 |  |
| A61 | 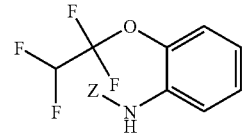 |
| A62 | 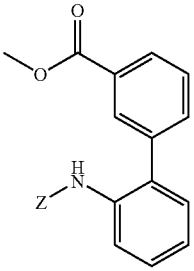 |
| A63 | 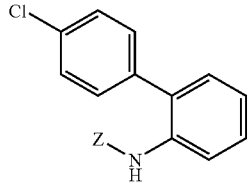 |
| A64 | 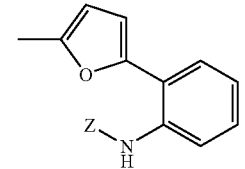 |
| A65 | 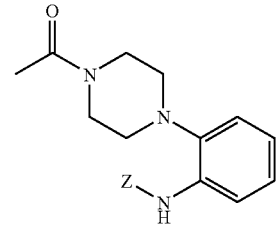 |
| A66 | 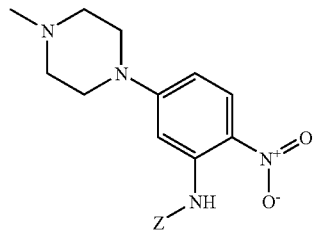 |
| A67 | 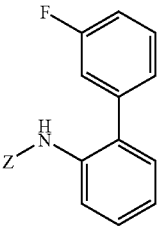 |

TABLE I-continued

| Code | A |
|---|---|
| A68 | |
| A69 | |
| A70 | |
| A71 | |
| A72 | |
| A73 | |
| A74 | |
| A75 | |
| A76 | |
| A77 | |
| A78 | |
| A79 | |
| A80 | |
| A81 | |
| A82 | |

TABLE I-continued

| Code | A |
|---|---|
| A83 | 3-methyl-4-(Z-amino)-N-hydroxybenzamide |
| A84 | 2-acetyl-4-(4-methylpiperazin-1-yl)-N-Z-aniline |
| A85 | 2-methoxy-5-(4-methylpiperazin-1-yl)-N-Z-aniline |
| A86 | [4-(Z-amino)-3-methylphenyl]-(4-methylpiperazin-1-yl)methanone |
| A87 | [3-(Z-amino)-4-methylphenyl]-(4-methylpiperazin-1-yl)methanone |
| A88 | 4-(Z-amino)-3-methylbenzamide |
| A89 | 2-methoxy-4-(4-methylpiperazin-1-yl)-N-Z-aniline |
| A90 | 2-cyano-4-(4-methylpiperazin-1-yl)-N-Z-aniline |
| A91 | 4-methyl-5-[(4-methylpiperazin-1-yl)methyl]-N-Z-aniline |
| A92 | 5-[(diethylamino)methyl]-4-methyl-N-Z-aniline |
| A93 | 4-methyl-3-(Z-amino)-N-hydroxybenzamide |
| A94 | 5-(4-methylpiperazin-1-yl)-2-(trifluoromethoxy)-N-Z-aniline |
| A95 | 5-[(1-methylpiperidin-4-yl)amino]-2-(trifluoromethoxy)-N-Z-aniline |
| A96 | tert-butyl 4-[3-(Z-amino)-4-(trifluoromethoxy)phenyl]piperazine-1-carboxylate |

(Structures as drawn in the table.)

TABLE I-continued

| Code | A |
|---|---|
| A97 | 4-(piperazin-1-yl)-2-(trifluoromethoxy)aniline with Z-NH substituent |
| A98 | 4-(4-methylpiperazin-1-yl)-2-methylaniline with Z-NH substituent |
| A99 | 4-(4-(pyrrolidin-1-yl)piperidin-1-yl)-2-(trifluoromethoxy)aniline with Z-NH substituent |
| A100 | N-(3-(4-methylpiperazin-1-yl)propyl)-4-(trifluoromethoxy)benzene-1,3-diamine with Z-NH |
| A101 | 4-(4-(3-(dimethylamino)propyl)piperazin-1-yl)-2-(trifluoromethoxy)aniline with Z-NH substituent |
| A102 | 4-(4-methyl-4-oxidopiperazin-4-ium-1-yl)-2-(trifluoromethoxy)aniline with Z-NH substituent |
| A103 | 4-(4-methyl-1,4-dioxidopiperazine-1,4-diium-1-yl)-2-(trifluoromethoxy)aniline with Z-NH substituent |
| A104 | Fmoc-protected prolyl amide of Z-NH-phenylamine |
| A105 | 2-methoxy-3-(Z-amino)pyridine |
| A106 | 5-methoxy-4-(Z-amino)pyrimidine |
| A107 | (S)-1-(4-(trifluoromethoxy)-3-(Z-amino)phenyl)-2-(pyrrolidin-1-ylmethyl)pyrrolidine |

TABLE I-continued

| Code | A |
|---|---|
| A108 | 4-(trifluoromethoxy)-N1-methyl-N1-(2-(diethylamino)ethyl)benzene-1,3-diamine with HN-Z on position 3 |
| A109 | 4-(trifluoromethoxy)-N-(2-(1-methylpyrrolidin-2-yl)ethyl)benzene-1,3-diamine with HN-Z |
| A110 | N-(1,2,2,6,6-pentamethylpiperidin-4-yl)-4-(trifluoromethoxy)benzene-1,3-diamine with Z-NH |
| A111 | 4-(trifluoromethoxy)-3-(1-(4-methyl-1,4-diazepan-1-yl))aniline with HN-Z |
| A112 | 4-(trifluoromethoxy)-N-(pyrrolidin-3-yl)benzene-1,3-diamine with HN-Z |
| A113 | 4-(trifluoromethoxy)-5-(1-methyl-1,2,3,6-tetrahydropyridin-4-yl)aniline with Z-NH |
| A114 | 4-(trifluoromethoxy)-5-(1-methylpiperidin-4-yl)aniline with Z-NH |
| A115 | 4-(trifluoromethoxy)-3-(4-methyl-2-(hydroxymethyl)piperazin-1-yl)aniline with HN-Z |
| A116 | N-acetyl-4-(4-methylpiperazin-1-yl)benzene-1,2-diamine with HN-Z |
| A117 | 4-(trifluoromethoxy)-3-(4-methyl-2-(hydroxymethyl)piperazin-1-yl)aniline (enantiomer) with HN-Z |
| A118 | 5-bromo-2-methoxyaniline with HN-Z |

TABLE I-continued
| Code | A |
|------|---|
| A119 |  |
| A120 |  |
TABLE II
| Code | B |
|------|---|
| B1 |  |
| B2 | 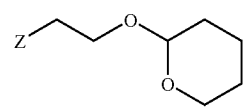 |
| B3 | 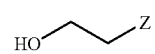 |
| B4 | 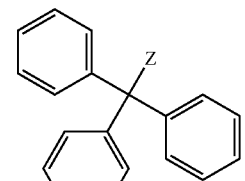 |
| B5 |  |
| B6 |  |
| B7 | 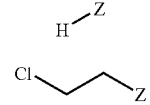 |
| B8 |  |
| B9 | 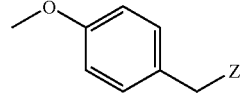 |
TABLE II-continued
| Code | B |
|------|---|
| B10 | 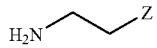 |
| B11 | 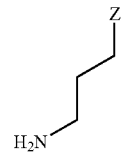 |
| B12 | 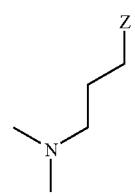 |
| B13 | 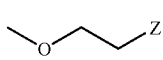 |
| B14 | 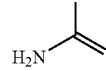 |
| B15 |  |
TABLE III
| Code | C |
|------|---|
| C1 |  |
| C2 | 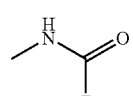 |
| C3 | 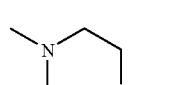 |
| C4 |  |
| C5 |  |
| C6 |  |

TABLE III-continued

| Code | C |
|------|---|
| C7 | CF$_3$-CH$_2$-NH-C(=O)-Z |
| C8 | 4-methoxybenzyl-NH-C(=O)-Z |

TABLE IV

| | | | | | |
|---|---|---|---|---|---|
| A1B1C1Z | A32B1C1Z | A48B1C1Z | A80B1C3Z | A97B1C1Z | A51B13C1Z |
| A2B1C1Z | A33B1C1Z | A39B1C4Z | A81B1C3Z | A98B1C2Z | A115B1C1Z |
| A3B1C1Z | A34B1C1Z | A48B1C2Z | A82B1C1Z | A98B1C3Z | A116B1C1Z |
| A4B1C1Z | A35B1C2Z | A50B1C1Z | A83B1C1Z | A98B1C1Z | A117B1C1Z |
| A5B1C1Z | A36B1C1Z | A35B1C3Z | A51B6C1Z | A49B8C2Z | A51B14C1Z |
| A6B1C1Z | A35B1C1Z | A51B1C2Z | A84B1C1Z | A49B7C2Z | A118B1C1Z |
| A7B1C2Z | A37B1C2Z | A51B1C3Z | A85B1C2Z | A49B7C1Z | A51B15C1Z |
| A8B1C2Z | A37B1C3Z | A51B1C1Z | A85B1C3Z | A49B7C3Z | A85B1C8Z |
| A8B1C3Z | A37B1C1Z | A52B1C1Z | A85B1C1Z | A99B1C1Z | A51B8C2Z |
| A8B1C1Z | A38B1C2Z | A53B1C1Z | A86B1C1Z | A100B1C1Z | A51B8C3Z |
| A7B1C1Z | A2B2C1Z | A54B1C1Z | A87B1C1Z | A101B1C1Z | A102 B5C1Z |
| A9B1C1Z | A39B1C1Z | A55B1C1Z | A88B1C1Z | A104B1C2Z | A103 B5C1Z |
| A10B1C1Z | A39B2C1Z | A56B1C1Z | A51B8C1Z | A105B1C1Z | |
| A11B1C1Z | A40B1C1Z | A57B1C1Z | A89B1C4Z | A106B1C1Z | |
| A12B1C2Z | A40B2C1Z | A58B1C1Z | A89B1C6Z | A107B1C1Z | |
| A13B1C1Z | A39B1C2Z | A59B1C1Z | A51B2C1Z | A108B1C1Z | |
| A14B1C1Z | A39B1C3Z | A60B1C1Z | A51B7C1Z | A109B1C1Z | |
| A15B1C1Z | A41B1C1Z | A61B1C1Z | A90B1C2Z | A110B1C1Z | |
| A16B1C1Z | A42B1C1Z | A62B1C1Z | A90B1C3Z | A111B1C1Z | |
| A17B1C1Z | A43B1C4Z | A63B1C1Z | A91B1C1Z | A112B1C1Z | |
| A18B1C1Z | A44B1C1Z | A64B1C1Z | A92B1C1Z | A49B8C3Z | |
| A19B1C1Z | A45B1C1Z | A65B1C1Z | A93B1C1Z | A49B8C1Z | |
| A20B1C1Z | A45B1C2Z | A66B1C1Z | A85B1C4Z | A51B5C2Z | |
| A21B1C2Z | A45B6C2Z | A67B1C1Z | A51B1C4Z | A51B5C3Z | |
| A22B1C1Z | A45B8C2Z | A68B1C1Z | A89B1C1Z | A51B5C1Z | |
| A23B1C2Z | A45B3C1Z | A69B1C1Z | A48B1C4Z | A51B8C1Z | |
| A24B1C1Z | A45B2C1Z | A70B1C1Z | A89B1C3Z | A51B9C1Z | |
| A25B1C1Z | A45B8C3Z | A71B1C1Z | A102B1C1Z | A51B10C1Z | |
| A21B1C3Z | A45B8C1Z | A72B1C1Z | A103B1C1Z | A113B1C1Z | |
| A21B1C1Z | A45B4C1Z | A73B1C1Z | A51B1C7Z | A114B1C1Z | |
| A26B1C1Z | A45B5C1Z | A74B1C1Z | A49B1C2Z | A49B6C1Z | |
| A27B1C1Z | A43B1C2Z | A75B1C1Z | A49B1C3Z | A49B4C1Z | |
| A28B1C1Z | A43B1C5Z | A76B1C1Z | A49B1C1Z | A51B4C1Z | |
| A29B1C1Z | A43B1C1Z | A77B1C1Z | A94B1C1Z | A49B11C1Z | |
| A30B1C1Z | A46B1C1Z | A78B1C1Z | A95B1C1Z | A51B11C1Z | |
| A31B1C1Z | A47B1C1Z | A79B1C1Z | A96B1C1Z | A51B12C1Z | |

The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ HPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 microm Waters Acquity HPLC (2.1×50 mm) column. Mobile phase A was formic acid 0.1% pH=3.3 buffer with acetonitrile (98:2), and mobile phase B was H$_2$O/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytic Method 2

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 30° C. at a flow rate of 1.0 mL/min using a C18, 3 microm Phenomenex (4.6×50 mm) column. Mobile phase A was ammonium acetate 5 mM pH=5.2 buffer with acetonitrile (95:5), and mobile phase B was H$_2$O/acetonitrile (5:95); the gradient was from 10 to 90% B in 8 minutes then ramp to 100% B in 1.0 minutes. The injection volume was 10 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytic Method 3

The HPLC equipment consisted of a Waters Acquity™ HPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 microm Waters Acquity HPLC (2.1×50 mm) column. Mobile phase A was ammonium hydroxide 0.05% pH=10 buffer with acetonitrile (95:5), and mobile phase B was H₂O/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES⁺) and 28 V (ES⁻); the source temperature was 120° C.; cone was 14 V (ES⁺) and 2.8 KV (ES⁻); full scan, mass range from 100 to 800 amu was set up.
HPLC/MS Analytical Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 1 mL/min using a RP18 Waters X Terra (3.0×20 mm) column. Mobile phase A was ammonium hydroxide 0.05% pH=10 buffer with acetonitrile (95:5), and Mobile phase B was H₂O/acetonitrile (5:95); the gradient was from 10 to 90% B in 4 minutes then hold 90% B 1 minutes. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of formula (I), as prepared according to the following examples, were purified by preparative HPLC.

The operative conditions are defined below:
HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 microm (19×250 mm) column. Mobile phase A was ammonium hydroxide 0.05% pH=10 buffer with acetonitrile (95:5), and Mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.
HPLC/MS Preparative Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 microm (19×250 mm) column. Mobile phase A was 0.1% trifluoro acetic acid in water/acetonitrile (95:5), and mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

Example 1

Ethyl 1-methyl-7-oxo-4,5,6,7-tetrahydro-1H-indazole-3-carboxylate

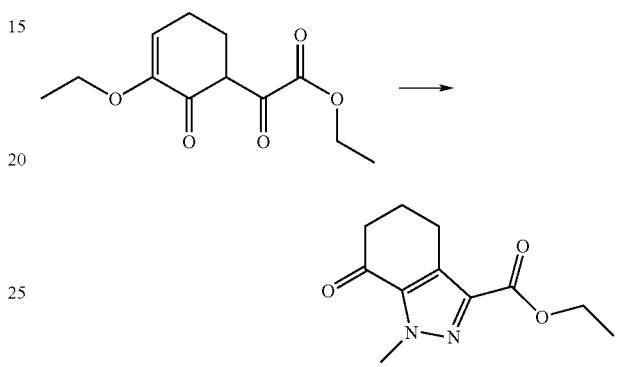

30 g (0.125 mol) of ethyl (3-ethoxy-2-oxocyclohex-3-en-1-yl)(oxo)acetate were dissolved in 150 mL of glacial acetic acid and 6.5 mL of methylhydrazine (0.125 mol) were added. The mixture was stirred at room temperature for 6 hours. The solvent was then evaporated and the crude redissolved in water, made basic with 30% NH₄OH and extracted with dichlormethane. The organic layer was then dried over Na₂SO₄ and concentrated. The residue was crystallized from diethyl ether to give 19.2 g (68% yield) of title compound.

¹H NMR (400 MHz, DMSO-d₆) δ ppm 1.12 (t, J=6.89 Hz, 3 H) 1.51 (t, J=6.94 Hz, 3 H) 2.06-2.58 (m, 4 H) 3.57 (m, 1 H) 3.86 (q, J=6.83 Hz, 2 H) 4.38 (q, J=6.94 Hz, 2 H) 6.09 (m, 1 H).

According to the same method, but employing the suitably substituted hydrazine derivative, the following compounds were prepared:

ethyl 1-(2-hydroxyethyl)-7-oxo-4,5,6,7-tetrahydro-1H-indazole-3-carboxylate

¹H NMR (400 MHz), DMSO-d₆) δ ppm 1.3 (t, J=7.20 Hz, 3 H) 1.9-2.9 (3 m, 6 H) 3.7 (m, 2 H) 4.3 (q, J=7.20 Hz, 2 H) 4.53 (t, J=5.85, 2 H) 4.77 (t, J=5.73, OH);

ethyl 1-(2-fluoroethyl)-7-oxo-4,5,6,7-tetrahydro-1H-indazole-3-carboxylate;

ethyl 1-ethyl-7-oxo-4,5,6,7-tetrahydro-1H-indazole-3-carboxylate

1H NMR (400 MHz, DMSO-d₆) δ ppm 1.32 (t, J=7.13 Hz, 3 H) 1.38-1.42 (m, 3 H) 2.73-2.79 (m, 2 H) 2.90-2.96 (m, 2 H) 4.30 (q, J=7.07 Hz, 2 H) 4.81 (q, J=7.19 Hz, 2 H) 6.59 (bs, 2H) 8.19 (s, 1 H);

ethyl 1-isopropyl-7-oxo-4,5,6,7-tetrahydro-1H-indazole-3-carboxylate.

Example 2

Ethyl 7-oxo-1-trityl-4,5,6,7-tetrahydro-1H-indazole-3-carboxylate

Step 1. Ethyl 7-oxo-4,5,6,7-tetrahydro-1H-indazole-3-carboxylate

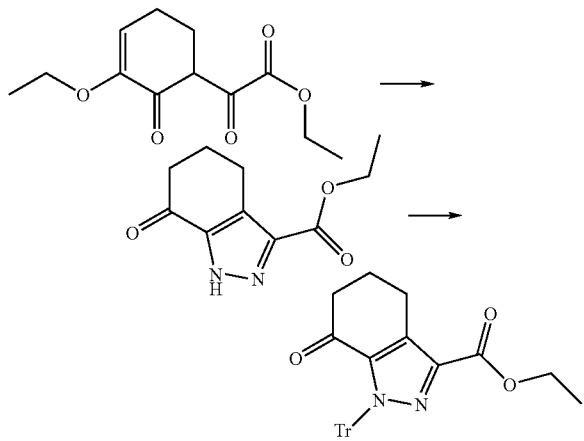

10.0 g (42 mmol) of ethyl (3-ethoxy-2-oxocyclohex-3-en-1-yl)(oxo)acetate were dissolved in 100 mL of ethanol, 2.1 mL of hydrazine hydrate were added and the solution stirred at reflux for one day. The solvent was then evaporated and the residue redissolved with dichloromethane. The organic layer was washed with water, dried over $Na_2SO_4$ and concentrated. The crude was triturated with diethyl ether and filtered to give 6.0 g of the title compound (70% yield).

$^1$H NMR (400 MHz, DMSO-$d_6$) δ ppm 1.28 (t, J=7.07 Hz, 3 H) 2.04 (m, 2 H) 2.51 (m, 2 H) 2.87 (t, J=6.10 Hz, 2 H) 4.27 (q, J=7.11 Hz, 2 H) 14.39 (s, 1 H).

Step 2. Ethyl 7-oxo-1-trityl-4,5,6,7-tetrahydro-1H-indazole-3-carboxylate 2.08 g (10.0 mmol) of ethyl 7-oxo-4,5,6,7-tetrahydro-1H-indazole-3-carboxylate were dissolved in 100 mL of dichloromethane and 0.76 mL of triethylamine and 3.07 g (11.0 mmol) of triphenylmethyl chloride were added. The solution was stirred at room temperature for 6 hours. Then the solution was further diluted with dichloromethane and washed with water. The organic layer was treated with anhydrous $Na_2SO_4$ and evaporated to dryness. The final product was obtained by crystallization from diethyl ether (3.24 g, 72% yield).

$^1$H NMR (400 MHz, DMSO-$d_6$) δ ppm 1.25 (t, J=7.01 Hz, 3 H) 2.16 (m, 2 H) 2.48 (m, 2 H) 2.98 (t, J=6.10 Hz, 2 H) 4.25 (q, J=7.01 Hz, 2 H) 6.92-7.33 (2m, 15 H).

Example 3

Ethyl 6-[(dimethylamino)methylene]-1-methyl-7-oxo-4,5,6,7-tetrahydro-1H-indazole-3-carboxylate

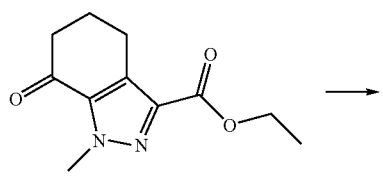

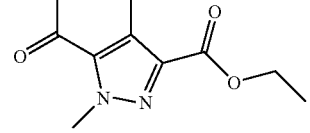

16 g (72 mmol) of ethyl 1-methyl-7-oxo-4,5,6,7-tetrahydro-1H-indazole-3-carboxylate were dissolved in 100 mL of dimethylformamide and 32 mL of dimethylformamide ditertbutyl acetate were added. The mixture was stirred at 60° C. for 8 hours. The solvent was then evaporated in vacuo and the product crystallized from ethanol to give the title compound (17.96 g, 90% yield).

$^1$H NMR (400 MHz, DMSO-$d_6$) δ ppm 1.31 (t, J=7.07 Hz, 3 H) 2.83 (m, 2 H) 2.92 (m, 2 H) 3.13 (s, 6 H) 4.14 (s, 3 H) 4.24 (q, J=7.07 Hz, 2 H) 7.49 and 7.52 (2 s, 1 H).

By working according to the same method the following compounds were prepared:

ethyl 6-[(dimethylamino)methylene]-7-oxo-1-trityl-4,5,6,7-tetrahydro-1H-indazole-3-carboxylate $^1$H NMR (400 MHz, DMSO-$d_6$) δ ppm 1.30 (t, J=7.07 Hz, 3 H) 2.75 (m, 2 H) 2.91 (m, 2 H) 2.94 (s, 6 H) 4.21 (q, J=7.07 Hz, 2 H) 6.90-7.30 (m, 15 H) 7.47 and 7.54 (2 s, 1 H);

ethyl 6-[(dimethylamino)methylene]-1-(2-hydroxyethyl)-7-oxo-4,5,6,7-tetrahydro-1H-indazole-3-carboxylate $^1$H NMR (400 MHz), DMSO-$d_6$) δ ppm 2.80 (t, J=6.34 Hz, 2 H) 2.88 (t, J=6.21, 2H) 3.70 (m, 2 H) 4.24 (q, J=7.07 Hz, 3 H) 4.58 (t, J=5.97 Hz, 2 H) 4.79 (bs, OH) 7.47 (bs, 1 H);

ethyl 6-[(dimethylamino)methylene]-1-(2-fluoroethyl)-7-oxo-4,5,6,7-tetrahydro-1H-indazole-3-carboxylate ethyl 6-[(dimethylamino)methylene]-1-ethyl-7-oxo-4,5,6,7-tetrahydro-1H-indazole-3-carboxylate ethyl 6-[(dimethylamino)methylene]-1-isopropyl-7-oxo-4,5,6,7-tetrahydro-1H-indazole-3-carboxylate.

Example 4

Ethyl 8-amino-1-methyl-1H-pyrazolo[4,3-h]quinazoline-3-carboxylate

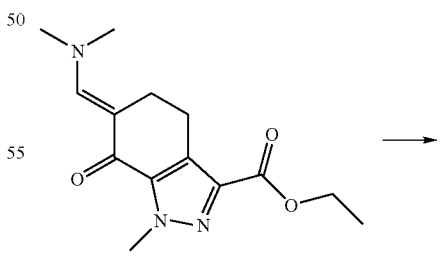

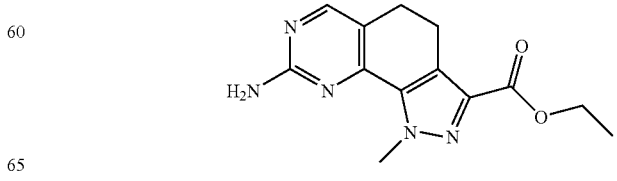

To a solution of 16.62 g (60 mmol) of ethyl 6-[(dimethylamino)methylene]-7-oxo-1-methyl-4,5,6,7-tetrahydro-1H-indazole-3-carboxylate in 0.5 L of DMF, 27 g (150 mmol) of guanidine carbonate was added. The mixture was stirred at 110° C. overnight. After cooling the mixture was poured into water (2.5 L) and stirred for 30 minutes. The precipitate was filtered, washed with water and dried to yield 26.83 g of title compound (91%).

$^1$H NMR (400 MHz, DMSO-$d_6$) δ ppm: 1.32 (t, J=7.07 Hz, 3 H) 2.76 (m, 2 H) 2.93 (m, 2 H) 4.25 (q, J=7.07 Hz, 2 H) 4.30 (s, 3 H) 6.57 (bs, 2 H) 8.19 (m, 1 H).

By working according to the same method the following compounds were prepared:

ethyl 8-amino-1-trityl-4,5-dihydro-1H-pyrazolo[4,3-h]quinazoline-3-carboxylate $^1$H NMR (400 MHz, DMSO-$d_6$) δ ppm: 1.29 (t, J=7.07 Hz, 3 H) 2.62 (m, 2 H) 2.98 (m, 2 H) 4.26 (q, J=7.07 Hz, 2 H) 6.45 (bs, 2 H) 7.06-7.45 (m, 15 H) 7.94 (s, 1 H);

ethyl 8-amino-1-(2-hydroxyethyl)-4,5-dihydro-1H-pyrazolo[4,3-h]quinazoline-3-carboxylate $^1$H NMR (400 MHz, DMSO-$d_6$) δ ppm 1.32 (t, J=7.07 Hz, 3 H) 2.76 (t, J=7.68 Hz, 2 H) 2.94 (t, J=7.50 Hz, 2 H) 3.79-3.88 (m, 2 H) 4.30 (q, J=7.07 Hz, 2 H) 4.80 (t, J=5.79 Hz, 1 H) 4.84 (t, J=5.97 Hz, 2 H) 6.55 (s, 2 H) 8.19 (s, 1 H);

ethyl 8-amino-1-(2-fluoroethyl)-4,5-dihydro-1H-pyrazolo[4,3-h]quinazoline-3-carboxylate ethyl 8-amino-1-ethyl-4,5-dihydro-1H-pyrazolo[4,3-h]quinazoline-3-carboxylate $^1$H NMR (400 MHz, DMSO-$d_6$) δ ppm 1.32 (t, J=7.13 Hz, 3 H) 1.38-1.42 (m, 3 H) 2.73-2.79 (m, 2 H) 2.90-2.96 (m, 2 H) 4.30 (q, J=7.07 Hz, 2 H) 4.81 (q, J=7.19 Hz, 2 H) 6.59 (bs, 2 H) 8.19 (s, 1 H);

ethyl 8-amino-1-isopropyl-4,5-dihydro-1H-pyrazolo[4,3-h]quinazoline-3-carboxylate ethyl 8-(5-bromo-2-trifluoromethoxy-phenylamino)-4,5-dihydro-1H-pyrazolo[4,3-h]quinazoline-3-carboxylate (A49B8C2Z)

$^1$H NMR (400 MHz, DMSO-$d_6$) δ ppm 1.34 (t, J=7.13 Hz, 3 H) 2.89 (m, 2 H) 2.99 (m, 2 H) 4.33 (q, J=7.13 Hz, 2 H) 7.34 (m, 2 H) 8.31 (s, 1 H) 8.43 (m, 1 H) 8.70 (s, 1 H) 9.06 (s, 1 H) 14.28 (br. s., 1 H);

ethyl 8-[5-(4-methyl-piperazin-1-yl)-2-trifluoromethoxy-phenylamino]-4,5-dihydro-1H-pyrazolo[4,3-h]quinazoline-3-carboxylate (A51B8C2Z)

$^1$H NMR (400 MHz, DMSO-$d_6$) δ ppm 1.32 (t, J=7.1 Hz, 3 H) 2.25 (s, 3 H) 2.46 (m, 4 H) 2.84 (m, 2 H) 2.98 (m, 2 H) 3.15 (m, 4 H) 4.19 (s, 3 H) 4.31 (q, J=7.1 Hz, 2 H) 6.79 (m, 1 H) 7.20 (m, 1 H) 7.30 (m, 1 H) 8.38 (bs, 1 H) 8.94 (s, 1 H);

ethyl 8-[2-methoxy-5-bromo-phenylamino]-4,5-dihydro-1H-pyrazolo[4,3-h]quinazoline-3-carboxylate (A118B1C2Z)

$^1$H NMR (400 MHz, DMSO-$d_6$) δ ppm 1.32 (t, J=7.07 Hz, 3 H) 2.88 (d, J=7.93 Hz, 2 H) 2.96-3.03 (m, 2 H) 3.88 (s, 3 H) 4.30 (q, J=7.15 Hz, 2 H) 4.34 (s, 3 H) 7.03 (d, J=8.78 Hz, 1 H) 7.19 (dd, J=8.66, 2.44 Hz, 1 H) 8.26 (s, 1 H) 8.37 (d, J=2.44 Hz, 1 H) 8.47 (s, 1 H).

Example 5

Ethyl 8-iodo-1-methyl-4,5-dihydro-1H-pyrazolo[4,3-h]quinazoline-3-carboxylate

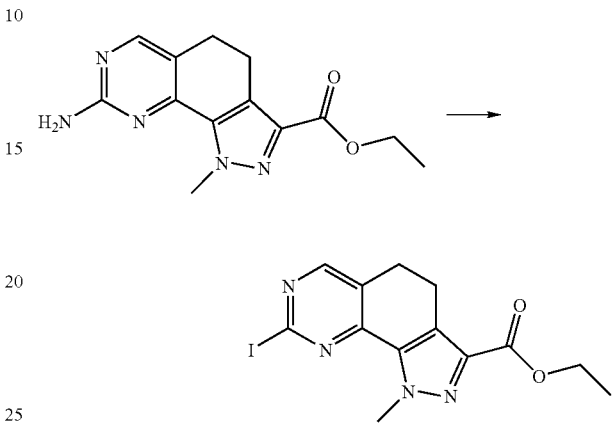

To a well stirred suspension of ethyl 8-amino-1-methyl-4,5-dihydro-1H-pyrazolo[4,3-h]quinazoline-3-carboxylate (9.0 g, 33 mmol) in dimethoxyethane (0.7 L) under $N_2$, cesium iodide (8.6 g, 33 mmol), bisublimated iodine (4.19 g, 16.5 mmol), copper iodide (2.0 g, 10 mmol) and isopentyl nitrite (6.62 mL, 49.5 mmol) were added in sequence. The reaction mixture was stirred vigorously at 65-70° C. for 3 hours. After cooling in an ice-water bath, the solid was filtered off. The filtrate was diluted with dichloromethane (2.0 L), washed with 30% ammonium hydroxide (150 mL), sodium thiosulphate (300 mL), brine, dried over anhydrous $Na_2SO_4$ and concentrated to give 5.69 g of the title compound (46% yield).

$^1$H NMR (400 MHz, DMSO-$d_6$), δ ppm 1.28 (t, J=7.07 Hz, 3 H) 2.81-3.07 (2t, J=8.90 Hz, 4 H) 4.24 (s, 3 H) 4.27 (q, J=7.07 Hz, 2 H) 8.5 (bs, 1 H).

By working according to this method, the following compounds were prepared:

ethyl 8-iodo-1-trityl-4,5-dihydro-1H-pyrazolo[4,3-h]quinazoline-3-carboxylate $^1$H NMR (400 MHz, DMSO-$d_6$) δ ppm: 1.28 (t, J=7.07 Hz, 3 H) 2.77 (m, 2 H) 3.06 (m, 2 H) 4.28 (q, J=7.07 Hz, 2 H) 7.06-7.28 (m, 15 H) 8.21 (s, 1 H);

ethyl 8-iodo-1-(2-hydroxyethyl)-4,5-dihydro-1H-pyrazolo[4,3-h]quinazoline-3-carboxylate ethyl 8-iodo-1-(2-fluoroethyl)-4,5-dihydro-1H-pyrazolo[4,3-h]quinazoline-3-carboxylate ethyl 8-iodo-1-ethyl-4,5-dihydro-1H-pyrazolo[4,3-h]quinazoline-3-carboxylate 1H NMR (400 MHz, DMSO-$d_6$) δ ppm 1.28-1.35 (m, 3 H) 1.42 (t, J=7.19 Hz, 3 H) 2.89-2.97 (m, 2 H) 2.99-3.05 (m, 2 H) 4.26-4.34 (m, 2 H) 4.69 (q, J=7.19 Hz, 2 H) 8.48 (s, 1 H);

ethyl 8-iodo-1-isopropyl-4,5-dihydro-1H-pyrazolo[4,3-h]quinazoline-3-carboxylate.

Example 6

Ethyl 1-methyl-8-(2-(t-butoxycarbonylaminophenylamino)-4,5-dihydro-1H-pyrazolo[4,3-h]quinazoline-3-carboxylate (A12B1C2Z)

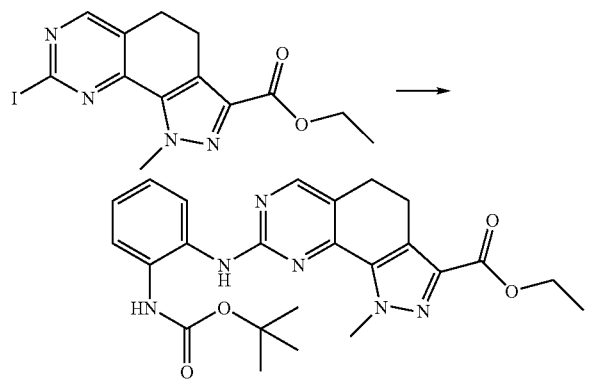

Palladium acetate [Pd(OAc)$_2$] (101 mg, 0.45 mmol), (±)-BINAP (280 mg, 0.45 mmol) and dimethylformamide (65 mL) were charged to a round-bottom flask flushed with argon. The flask was evacuated and backfilled with argon. The mixture was stirred under argon for 30 minutes and added to a mixture of 2-(t-butoxycarbonylamino)aniline (2.6 g, 12.5 mmol), ethyl 8-iodo-1-methyl-4,5-dihydro-1H-pyrazolo[4,3-h]quinazoline-3-carboxylate (1.6 g, 4.16 mmol), and potassium carbonate (5.74 g, 41.6 mmol) in dimethylformamide (50 mL). The resulting mixture was stirred at 70° C. for 6 hours under argon. After cooling to room temperature, the reaction mixture was filtered on a pad of celite. The solvent was concentrated, the crude solid was purified by flash chromatography on silica gel (eluant: hexane/ethyl acetate 60/40) to afford 1.18 g (61% yield) of the title compound.

$^1$H NMR (400 MHz, DMSO-d$_6$) δ ppm 1.32 (t, J=7.1 Hz, 3 H) 1.46 (s, 9 H) 2.84 (m, 4 H) 2.96 (m, 2 H) 4.20 (s, 3 H) 4.30 (q, J=7.1 Hz, 2 H) 7.12 (m, 2 H) 7.51 (m, 1 H) 7.71 (m, 1 H) 8.38 (s, 1 H) 8.65 (s, 1 H) 8.60 (s, 1 H).

By working according to the above method, the following compounds were prepared:

TABLE V

| Code | NMR data |
|---|---|
| A45B1C2Z | $^1$H NMR (400 MHz, DMSO-d$_6$) δ ppm 1.30 (t, J = 7.1 Hz, 3 H) 2.84 (m, 2 H) 2.97 (m, 2 H) 4.18 (s, 3 H) 4.29 (q, J = 7.1 Hz, 2 H) 7.23 (m, 1 H) 7.40 (m, 2 H) 7.85 (m, 1 H) 8.38 (s, 1 H) 9.08 (s, 1 H) |
| A43B1C2Z | $^1$H NMR (400 MHz, DMSO-d$_6$) δ ppm 1.30 (t, J = 7.07 Hz, 3 H) 2.86 (m, 2 H) 2.99 (m, 2 H) 4.23 (s, 3 H) 4.30 (q, J = 7.07 Hz, 2 H) 7.61 (m, 1 H) 7.64 (m, 1 H) 7.91 (m, 1 H) 8.41 (s, 1 H) 9.25 (s, 1 H) |
| A48B1C2Z | $^1$H NMR (400 MHz, DMSO-d$_6$) δ ppm 1.30 (t, J = 7.1 Hz, 3 H) 2.23 (s, 3 H) 2.47 (m, 4 H) 2.80 (m, 2 H) 2.95 (m, 2 H) 3.15 (m, 4 H) 4.16 (s, 3 H) 4.28 (q, J = 7.1 Hz, 2 H) 6.87 (d, J = 2.7 Hz, 1 H) 6.96 (dd, J = .9.1 and 2.7 Hz, 1 H) 7.48 (d, J = 9.1 1 H) 8.30 (bs, 1 H) 8.79 (s, 1 H) |
| A51B1C2Z | $^1$H NMR (400 MHz, DMSO-d$_6$) δ ppm 1.32 (t, J = 7.1 Hz, 3 H) 2.25 (s, 3 H) 2.46 (m, 4 H) 2.84 (m, 2 H) 2.98 (m, 2 H) 3.15 (m, 4 H) 4.19 (s, 3 H) 4.31 (q, J = 7.1 Hz, 2 H) 6.79 (m, 1 H) 7.20 (m, 1 H) 7.30 (m, 1 H) 8.38 (bs, 1 H) 8.94 (s, 1 H) |
| A39B1C2Z | $^1$H NMR (400 MHz, DMSO-d$_6$) δ ppm 1.31 (t, J = 7.1 Hz, 3 H) 2.25 (s, 3 H) 2.47 (m, 4 H) 2.54 (s, 3 H) 2.90 (m, 2 H) 2.99 (m, 2 H) 3.37 (m, 4 H) 4.30 (q, J = 7.1 Hz, 2 H) 4.36 (s, 3 H) 6.61 (dd, J = 9.27 and 2.56 Hz, 1 H) 7.86 (d, J = 9.27 Hz, 1 H) 8.28 (d, J = 2.56 Hz, 1 H) 8.53 (bs, 1 H) 12.12 (s, 1 H) |
| A85B1C2Z | $^1$H NMR (400 MHz, DMSO-d$_6$) δ ppm 1.31 (t, J = 7.07 Hz, 3 H) 2.23 (s, 3 H) 2.44-2.48 (m, 4 H) 2.83 (t, J = 7.62 Hz, 2 H) 2.97 (t, J = 7.87 Hz, 2 H) 2.99-3.02 (m, 4 H) 3.78 (s, 3 H) 4.29 (q, J = 7.07 Hz, 2 H) 4.28 (s, 3 H) 6.59 (dd, J = 8.78, 2.93 Hz, 1 H) 6.91 (d, J = 8.90 Hz, 1 H) 7.68 (d, J = 2.80 Hz, 1 H) 8.11 (s, 1 H) 8.39 (s, 1 H) |
| A90B1C2Z | $^1$H NMR (400 MHz, DMSO-d$_6$) δ ppm 1.30 (t, J = 7.07 Hz, 3 H) 2.28 (bs, 3 H) 2.83 (t, J = 7.68 Hz, 2 H) 2.96 (t, J = 7.38 Hz, 2 H) 3.20 (bs, 2 H) 4.17 (s, 3 H) 4.28 (q, J = 7.15 Hz, 2 H) 7.25-7.30 (m, 1 H) 7.29 (bs, 1 H) 7.41 (d, J = 9.75 Hz, 1 H) 8.34 (s, 1 H) 9.31 (s, 1 H) |
| A45B6C2Z | $^1$H NMR (400 MHz, DMSO-d$_6$) δ ppm 1.28 (t, J = 7.07 Hz, 3 H) 2.77 (m, 2 H) 3.06 (m, 2 H) 4.28 (q, J = 7.07 Hz, 2 H) 7.06-7.28 (m, 16 H) 7.40 (m, 2 H) 7.85 (m, 1 H) 8.38 (s, 1 H) 9.08 (s, 1 H) |
| A49B1C2Z | $^1$H NMR (400 MHz, DMSO-d$_6$) δ ppm 1.31 (t, J = 7.13 Hz, 3 H) 2.83-2.89 (m, 2 H) 2.94-3.01 (m, 2 H) 4.26 (s, 3 H) 4.30 (q, J = 7.13 Hz, 2 H) 7.37 (d, J = 0.85 Hz, 2 H) 8.26 (t, J = 1.28 Hz, 1 H) 8.45 (s, 1 H) 9.29 (s, 1 H) |
| A98B1C2Z | $^1$H NMR (400 MHz, DMSO-d$_6$) δ ppm 1.30 (t, J = 7.07 Hz, 3 H) 2.12 (s, 3 H) 2.22 (s, 3 H) 2.42-2.47 (m, 4 H) 2.80 (t, J = 7.68 Hz, 2 H) 2.92-2.97 (m, 2 H) 3.03-3.08 (m, 4 H) 4.14 (s, 3 H) 4.28 (q, J = 7.15 Hz, 1 H) 6.67 (dd, J = 8.29, 2.56 Hz, 1 H) 7.01 (d, J = 2.56 Hz, 1 H) 7.05 (d, J = 8.78 Hz, 1 H) 8.30 (s, 1 H) 8.68 (s, 1 H) |

TABLE V-continued

| Code | NMR data |
|---|---|
| A49B7C2Z | $^1$H NMR (400 MHz, DMSO-d$_6$) δ ppm 1.25 (t, J = 7.13 Hz, 3 H) 1.32 (t, J = 7.07 Hz, 3 H) 2.84-2.89 (m, 2 H) 2.95-3.01 (m, 2 H) 4.30 (q, J = 7.15 Hz, 2 H) 4.64 (q, J = 7.19 Hz, 2 H) 7.37-7.41 (m, 1 H) 7.41-7.45 (m, 1 H) 8.07 (d, J = 2.20 Hz, 1 H) 8.45 (s, 1 H) 9.29 (s, 1 H) |
| A49B6C2Z | $^1$H NMR (400 MHz, DMSO-d$_6$) δ ppm 1.29 (t, J = 7.07 Hz, 3 H) 2.77 (m, 2 H) 3.06 (m, 2 H) 4.28 (q, J = 7.07 Hz, 2 H) 7.06-7.28 (m, 15 H) 7.28-7.38 (m, 2 H) 8.33 (s, 1 H) 8.58 (s, 1 H) |
| A113B1C2Z | $^1$H NMR (400 MHz, DMSO-d$_6$) δ ppm 1.31 (t, J = 7.07 Hz, 3 H) 2.29 (s, 3 H) 2.43-2.49 (m, 2 H) 2.55-2.60 (m, 2 H) 2.80-2.88 (m, 2 H) 2.94-3.00 (m, 2 H) 3.00-3.05 (m, 2 H) 4.15 (s, 3 H) 4.29 (q, J = 7.07 Hz, 2 H) 6.13-6.21 (m, 1 H) 7.25-7.31 (m, 1 H) 7.32-7.38 (m, 1 H) 7.83 (d, J = 2.19 Hz, 1 H) 8.39 (s, 1 H) 9.10 (s, 1 H) |
| A114B1C2Z | $^1$H NMR (400 MHz, DMSO-d$_6$) δ ppm 1.31 (t, J = 7.13 Hz, 3 H) 1.74-1.87 (m, 2 H) 1.99-2.08 (m, 2 H) 2.80-2.89 (m, 6 H) 2.95-3.01 (m, 2 H) 3.02-3.14 (m, 2 H) 3.49-3.56 (m, 2 H) 4.20 (s, 3 H) 4.29 (q, J = 7.11 Hz, 2 H) 7.10 (dd, J = 8.29, 2.32 Hz, 1 H) 7.36-7.41 (m, 1 H) 7.71 (d, J = 2.19 Hz, 1 H) 8.40 (s, 1 H) 9.12 (s, 1 H) |

Example 7

Ethyl 1-methyl-8-(2-aminophenylamino)-4,5-dihydro-1H-pyrazolo[4,3-h]quinazoline-3-carboxylate hydrochloride salt (A7B1C2Z)

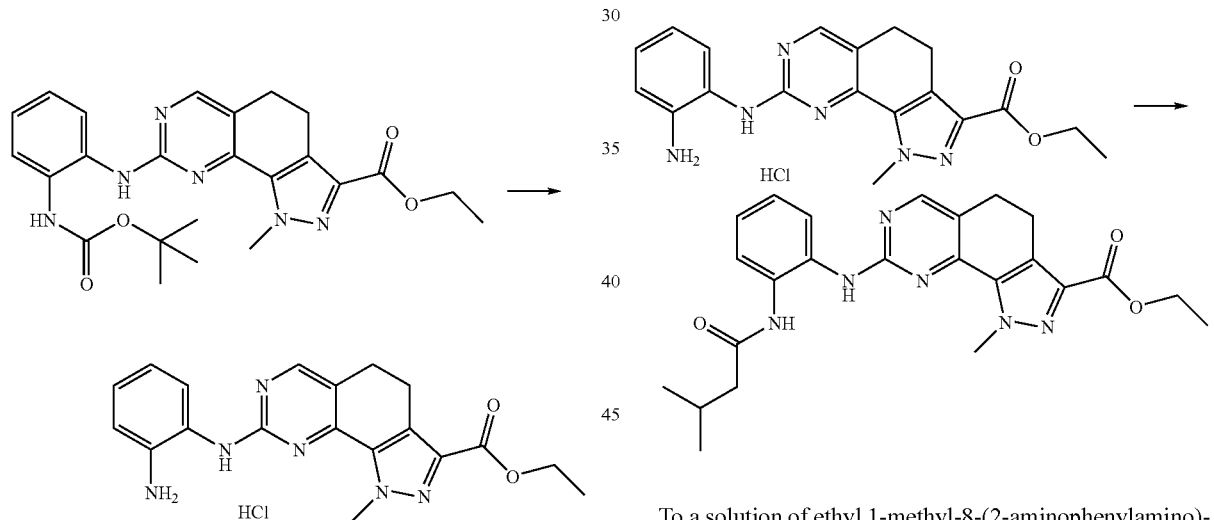

0.85 g (1.83 mmol) of ethyl 1-methyl-8-(2-(t-butoxycarbonylaminophenylamino)-4,5-dihydro-1H-pyrazolo[4,3-h]quinazoline-3-carboxylate were dissolved in 50 mL of dichloromethane to which 30 mL of HCl 4N in dioxane were added. The solution was stirred at room temperature 2 h and the solvent removed in vacuo. The residue was crystallized from diethyl ether to give 0.70 g of the title compound (96% yield).

$^1$H NMR (400 MHz, DMSO-d$_6$) δ ppm (as free base) 1.32 (t, J=7.1 Hz, 3 H) 2.82 (m, 4 H) 2.96 (m, 2 H) 4.19 (s, 3 H) 4.28 (q, J=7.1 Hz, 2 H) 4.85 (bs, 2 H) 6.58 (m, 1 H) 6.76 (m, 1 H) 6.90 (m, 1 H) 7.32 (m, 1 H) 8.32 (s, 1 H) 8.52 (s, 1 H).

Example 8

Ethyl 1-methyl-8-[2-(3-methyl-butyrylamino)-phenylamino]-4,5-dihydro-1H-pyrazolo[4,3-h]quinazoline-3-carboxylate (A35B1C2Z)

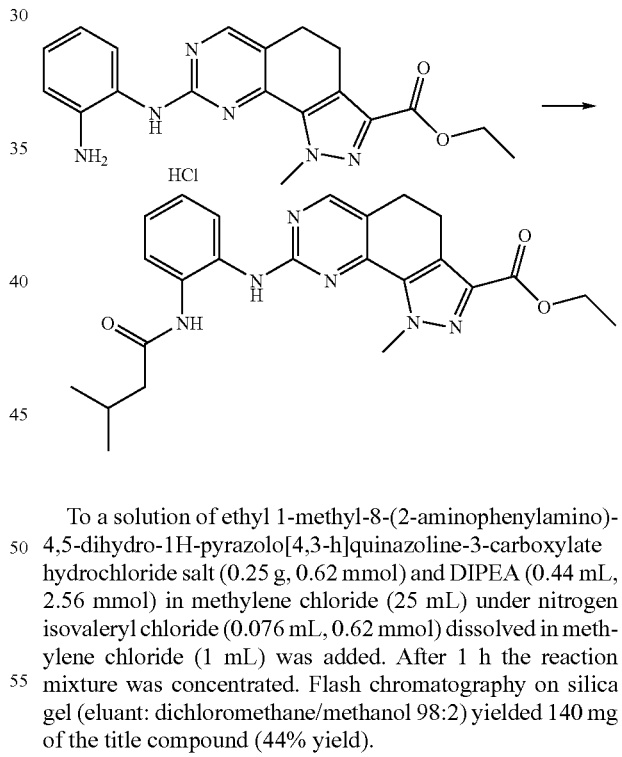

To a solution of ethyl 1-methyl-8-(2-aminophenylamino)-4,5-dihydro-1H-pyrazolo[4,3-h]quinazoline-3-carboxylate hydrochloride salt (0.25 g, 0.62 mmol) and DIPEA (0.44 mL, 2.56 mmol) in methylene chloride (25 mL) under nitrogen isovaleryl chloride (0.076 mL, 0.62 mmol) dissolved in methylene chloride (1 mL) was added. After 1 h the reaction mixture was concentrated. Flash chromatography on silica gel (eluant: dichloromethane/methanol 98:2) yielded 140 mg of the title compound (44% yield).

$^1$H NMR (400 MHz, DMSO-d$_6$) δ ppm 0.93 (d, J=6.6 Hz, 6 H) 1.32 (t, J=7.07 Hz, 3 H) 2.06 (m, 1 H) 2.24 (d, J=7.2 Hz, 2 H) 2.84 (m, 2 H) 2.97 (m, 2 H) 4.18 (s, 3 H) 4.30 (q, J=7.12 Hz, 1 H) 7.21 (m, 1 H) 7.23 (m, 1 H) 7.43 (d, J=7.7 Hz, 1 H) 7.80 (d, J=7.7 Hz, 1 H) 8.37 (s, 1 H) 8.47 (bs, 1 H) 9.68 (bs, 1H).

By working according to the above method, after preparing the acyl chloride from the corresponding carboxylic acid, the following compounds were prepared:

TABLE VI

| Code | NMR data |
| --- | --- |
| A21B1C2Z | $^1$H NMR (400 MHz, DMSO-$d_6$) δ ppm 1.30 (t, J = 7.07 Hz, 3 H) 2.07 (s, 3 H) 2.83 (m, 2 H) 2.95 (m, 2 H) 4.18 (s, 3 H) 4.28 (q, J = 7.07 Hz, 1 H) 7.09 (m, 1 H) 7.17 (m, 1 H) 7.48 (d, J = 7.7 Hz, 1 H) 7.77 (d, J = 7.7 Hz, 1 H) 8.37 (s, 1 H) 8.58 (bs, 1 H) 9.62 (bs, 1 H) |
| A38B1C2Z | $^1$H NMR (400 MHz, DMSO-$d_6$) δ ppm 1.32 (t, J 7.19 Hz, 3 H) 2.07 (s, 3 H) 2.85 (m, 2 H) 2.97 (m, 2 H) 3.55 (q, J = 1.22 Hz, 2 H) 4.16 (s, 3 H) 4.29 (q, J = 7.19 Hz, 1 H) 7.15 (m, 1 H) 7.22 (m, 1 H) 7.60 (dd, J = 7.93 1.46 Hz, 1 H) 7.73 (dd, J = 7.93 1.46 Hz, 1 H) 8.39 (s, 1 H) 8.59 (bs, 1 H) 9.82 (bs, 1 H) |
| A37B1C2Z | $^1$H NMR (400 MHz, DMSO-$d_6$) δ ppm 1.32 (t, J = 7.07 Hz, 3 H) 2.84 (m, 2 H) 2.96 (m, 2 H) 3.38 (s, 3 H) 4.20 (s, 3 H) 4.30 (q, J = 7.07 Hz, 1 H) 6.09 (m, 1 H) 6.89 (m, 1 H) 7.02 (m, 1 H) 7.16 (m, 1 H) 7.23 (m, 1 H) 7.53 (m, 1 H) 7.80 (m, 1 H) 8.38 (s, 1 H) 8.70 (s, 1 H) 9.56 (s, 1 H) |
| A8B1C2Z | $^1$H NMR (400 MHz, DMSO-$d_6$) δ ppm 1.32 (t, J = 7.07 Hz, 3 H) 2.84 (m, 2 H) 2.97 (m, 2 H) 4.21 (s, 3 H) 4.29 (q, J = 7.07 Hz, 1 H) 6.17 (m, 1 H) 6.89 (m, 1 H) 6.98 (m, 1 H) 7.17 (m, 1 H) 7.25 (m, 1 H) 7.52 (m, 1 H) 7.83 (m, 1 H) 8.37 (s, 1 H) 8.72 (s, 1 H) 9.68 (s, 1 H) 11.78 (s, 1 H) |
| A23B1C2Z | $^1$H NMR (400 MHz, DMSO-$d_6$) δ ppm 1.32 (t, J = 7.07 Hz, 3 H) 1.82 (m, 2 H) 1.98 (m, 1 H) 2.28 (m, 1 H) 2.66 (m, 2 H) 2.74 (m, 2 H) 2.87 (m, 2 H) 3.99 (s, 3 H) 4.10 (s, 2 H) 4.18 (s, 3 H) 4.29 (q, J = 7.07 Hz, 1 H) 4.52 (m, 1 H) 7.09 (m, 1 H) 7.0-7.91 (m, 12 H) 8.08, 8.26 (s, 1 H) 8.58, 8.70 (s, 1 H) 9.50, 9.70 (s, 1 H) |
| A104B1C2Z | $^1$H NMR (400 MHz, DMSO-$d_6$) δ ppm 1.32 (t, J = 7.07 Hz, 3 H) 1.82 (m, 2 H) 1.98 (m, 1 H) 2.28 (m, 1 H) 2.66 (m, 2 H) 2.74 (m, 2 H) 2.87 (m, 2 H) 3.99 (s, 3 H) 4.10 (s, 2 H) 4.18 (s, 3 H) 4.29 (q, J = 7.07 Hz, 1 H) 4.52 (m, 1 H) 7.09 (m, 1 H) 7.0-7.91 (m, 12 H) 8.08, 8.26 (s, 1 H) 8.58, 8.70 (s, 1 H) 9.50, 9.70 (s, 1 H) |

Example 9

Ethyl 8-(2-(trifluoromethoxyphenylamino)-4,5-dihydro-1H-pyrazolo[4,3-h]quinazoline-3-carboxylate (A45B8C2Z)

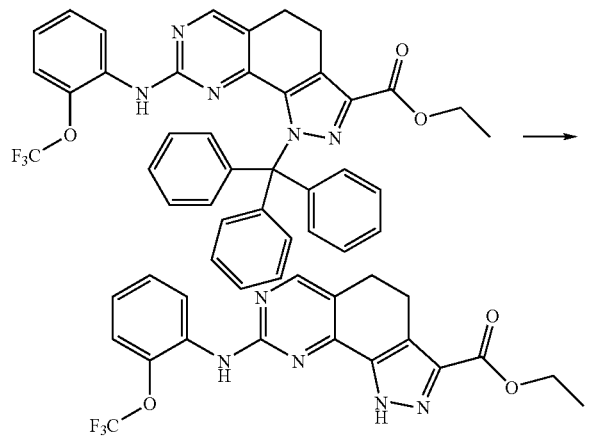

Ethyl 1-trityl-8-(2-(trifluoromethoxyphenylamino)-4,5-dihydro-1H-pyrazolo[4,3-h]quinazoline-3-carboxylate (140 mg, 0.21 mmol) in DCM (10 mL) was treated with trifluoroacetic acid (1 mL). The resulting mixture was stirred at room temperature for 1 hour and the solvent removed in vacuo. The residue was redissolved in dichloromethane and washed with a saturated solution of NaHCO$_3$. The organic layer was then dried over Na$_2$SO$_4$ and the solvent evaporated to dryness. The crude solid was purified by flash chromatography on silica gel (eluant: hexane/ethyl acetate 60/40) to afford in quantitative yield 88 mg of the title compound.

$^1$H NMR (400 MHz, DMSO-$d_6$) δ ppm 1.33 (t, J=7.1 Hz, 3 H) 2.87 (m, 2 H) 2.99 (m, 2 H) 4.32 (q, J=7.1 Hz, 2 H) 7.17 (m, 1 H) 7.40 (m, 2 H) 8.20 (m, 1 H) 8.37 (s, 1H) 8.70 (s, 1H).

Example 10

8-{2-[((S)-pyrrolidine-2-carbonyl)-amino]-phenylamino}-1-methyl-1H-pyrazolo[4,3-h]quinazoline-3-carboxamide (A25B1C1Z)

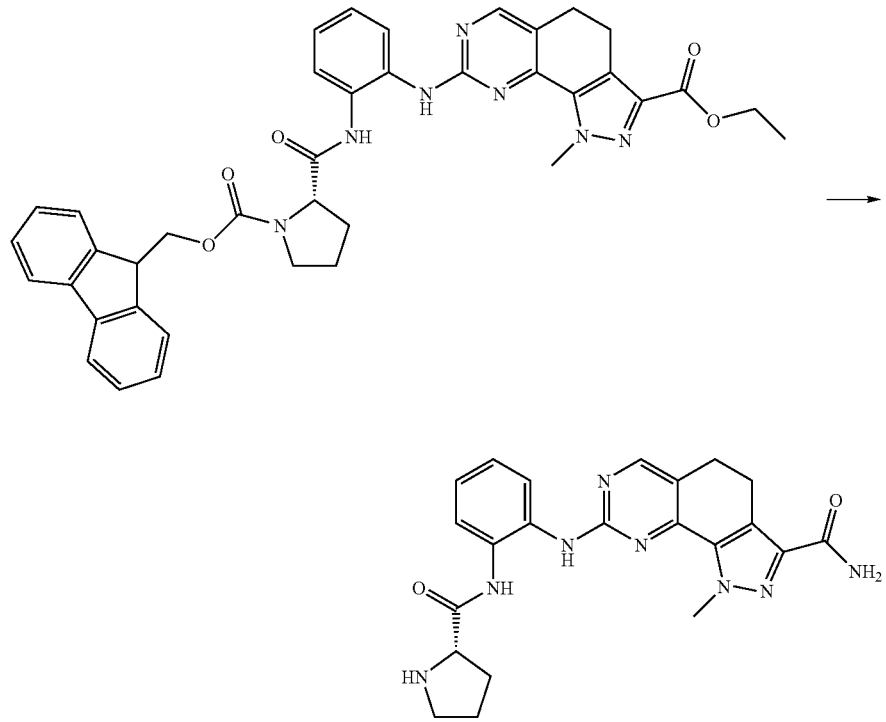 [SMILES: CCOC(=O)c1nn(C)c2c1CCc1cnc(Nc3ccccc3NC(=O)[C@@H]3CCCN3C(=O)OCC3c4ccccc4-c4ccccc43)nc1-2 ; Cn1nc(C(N)=O)c2c1-c1nc(Nc3ccccc3NC(=O)[C@@H]3CCCN3)ncc1CC2]

Ethyl 8-{2-[((S)—N-FMOC-pyrrolidine-2-carbonyl)-amino]-phenylamino}-1-methyl-1H-pyrazolo[4,3-h]quinazoline-3-carboxylate (200 mg, 0.29 mmol) was suspended in 20 mL of ethanol and 20 mL of NH$_4$OH 30% mixture. The mixture was maintained at 65° C. under stirring for 12 h in a closed bottle. The solvent was then evaporated to dryness, the residue redissolved with dichloromethane and washed with water. The organic layer was dried over Na$_2$SO$_4$ and evaporated. The crude product was purified by flash chromatography on silica gel (eluant: dichloromethane/methanol 94/6) to afford 60 mg (47% yield) of the title compound.

$^1$H NMR (400 MHz, DMSO-d$_6$) δ ppm 1.25 (m, 1 H) 1.45 (m, 1 H) 1.61 (m, 1 H) 1.92 (m, 1 H) 2.21 (m, 1 H) 2.69 (m, 1 H) 2.80 (m, 2 H) 2.95 (m, 2 H) 3.64 (m, 1 H) 3.98 (s, 3 H) 7.12 (m, 1 H) 7.23 (m, 2 H) 7.33 (m, 1 H) 7.45 (m, 1 H) 8.02 (m, 1 H) 8.36 (s, 1H).

By working according to this method, the following compounds were prepared:

TABLE VII

| Code | NMR data |
| --- | --- |
| A36B1C1Z | $^1$H NMR (400 MHz, DMSO-d$_6$) δ ppm 1.25 (m, 1 H) 1.45 (m, 1 H) 1.61 (m, 1 H) 1.92 (m, 1 H) 2.21 (m, 1 H) 2.69 (m, 1 H) 2.80 (m, 2 H) 2.95 (m, 2 H) 3.64 (m, 1 H) 3.98 (s, 3 H) 7.12 (m, 1 H) 7.23 (m, 2 H) 7.33 (m, 1 H) 7.45 (m, 1 H) 8.02 (m, 1 H) 8.36 (s, 1 H) |
| A45B1C1Z | $^1$H NMR (400 MHz, DMSO-d$_6$) δ ppm 2.82 (m, 2 H) 2.99 (m, 2 H) 4.17 (s, 3 H) 7.23 (m, 2 H) 7.39 (m, 2 H) 7.46 (bs, 1 H) 7.89 (m, 1 H) 8.38 (s, 1 H) 9.05 (s, 1 H) |
| A7B1C1Z | $^1$H NMR (400 MHz, DMSO-d$_6$) δ ppm 2.79 (m, 4 H) 2.97 (m, 2 H) 4.16 (s, 3 H) 4.85 (bs, 2 H) 6.58 (m, 1 H) 6.75 (m, 1 H) 6.90 (m, 1 H) 7.23 (bs, 1 H) 7.34 (m, 1 H) 7.44 (bs, 1 H) 8.31 (s, 1 H) 8.49 (s, 1 H) |

Example 11

1-methyl-8-(2-trifluoromethoxy-4-bromophenylamino]-4,5-dihydro-1H-pyrazolo[4,3-h]quinazoline-3-carboxamide (A43B1C1Z)

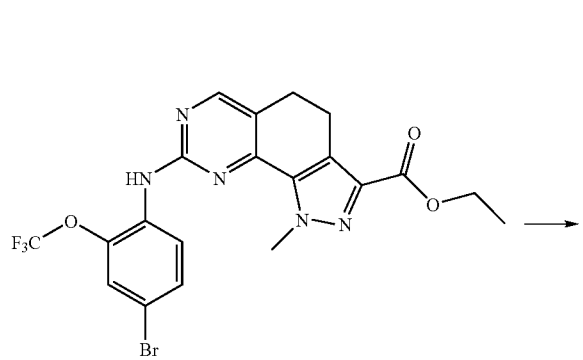

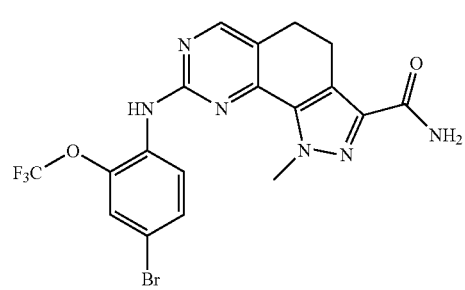

Ethyl 1-methyl-8-(2-trifluoromethoxy-4-bromophenylamino]-4,5-dihydro-1H-pyrazolo[4,3-h]quinazoline-3-carboxylate (330 mg, 0.64 mmol) was suspended in 10 mL of tetrahydrofuran. Ammonium chloride (106 mg 2.0 mmol) and LiN(TMS)$_2$ 1 N in THF (4.0 mL, 4.0 mmol) were added. The mixture was stirred at room temperature for 0.5 h. The solvent was then evaporated to dryness, the residue suspended in water and filtered to afford 288 mg (93% yield) of the title compound.

$^1$H NMR (400 MHz, DMSO-d$_6$) δ ppm 2.81 (m, 2 H) 2.98 (m, 2 H) 4.19 (s, 3 H) 7.24 (bs, 1 H) 7.42 (bs, 1 H) 7.60 (m, 1 H) 7.62 (m, 1 H) 7.92 (m, 1 H) 8.39 (s, 1 H) 9.19 (s, 1 H).

By working according to this method, the following compounds were prepared:

Example 12

Potassium 8-iodo-1-methyl-4,5-dihydro-1H-pyrazolo[4,3-h]quinazoline-3-carboxylate

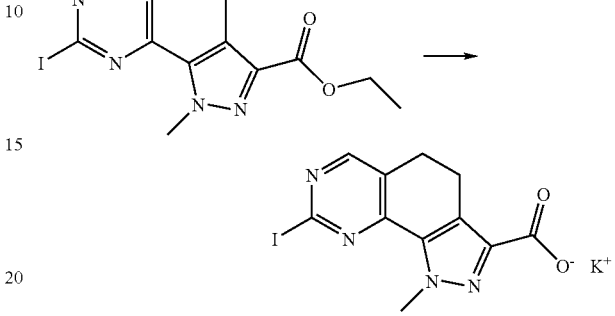

Ethyl 8-iodo-1-methyl-4,5-dihydro-1H-pyrazolo[4,3-h]quinazoline-3-carboxylate (384 mg, 1 mmol) was suspended in anhydrous ethanol (10 mL) and treated with a 1.5 M solution of potassium hydroxide in ethanol (6.6 mL, 10 mmol) at room temperature, overnight. The resulting precipitate was collected by filtration to give the title compound (323 mg, 82% yield) as a white solid.

$^1$H NMR (400 MHz, DMSO-d$_6$) δ ppm 2.79 (m, 2 H) 2.96 (m, 2 H) 4.10 (s, 3 H) 8.34 (s, 1 H).

By working according to the above method the following compounds were prepared:

potassium 8-iodo-1-trityl-4,5-dihydro-1H-pyrazolo[4,3-h]quinazoline-3-carboxylate $^1$H NMR (400 MHz, DMSO-d$_6$) δ ppm 2.66 (m, 2 H) 3.04 (m, 2 H) 7.15-7.25 (m, 15 H) 8.10 (s, 1 H);

potassium 8-amino-1-trityl-4,5-dihydro-1H-pyrazolo[4,3-h]quinazoline-3-carboxylate $^1$H NMR (400 MHz, DMSO-d$_6$) δ ppm 2.54 (m, 2 H) 2.94 (m, 2 H) 4.99 (bs 2 H) 7.12-7.18 (m, 15 H) 8.57 (s, 1 H);

potassium 8-amino-1-methyl-4,5-dihydro-1H-pyrazolo[4,3-h]quinazoline-3-carboxylate $^1$H NMR (400 MHz, DMSO-d$_6$) δ ppm 2.70 (m, 2H) 2.94 (m, 2H) 4.10 (s, 3H) 4.98 (bs 2H) 8.55 (s, 1H).

TABLE VIII

| Code | NMR data |
|---|---|
| A43B1C4Z | $^1$H NMR (400 MHz, DMSO-d$_6$) δ ppm 2.73 (d, J = 4.76 Hz, 3 H) 2.82 (m, 2 H) 2.98 (m, 2 H) 4.19 (s, 3 H) 7.60 (m, 1 H) 7.62 (m, 1 H) 7.92 (m, 1 H) 8.08 (q, J = 4.76 Hz, 1 H) 8.39 (s, 1 H) 9.20 (s, 1 H) |
| A43B1C5Z | $^1$H NMR (400 MHz, DMSO-d$_6$) δ ppm 2.24 (s, 3 H) 2.38 (m, 4 H) 3.31 (m, 4 H) 3.62 (m, 2 H) 3.80 (m, 2 H) 4.17 (s, 3 H) 7.59 (dd, J = 8.78 and 2.32 Hz, 1 H) 7.62 (m, 1 H) 7.91 (d, J = 8.78 Hz, 1 H) 8.08 (q, J = 4.76 Hz, 1 H) 8.39 (s, 1 H) 9.20 (s, 1 H) |
| A48B1C1Z | $^1$H NMR (400 MHz, DMSO-d$_6$) δ ppm 2.23 (s, 3 H) 2.46 (m, 4 H) 2.77 (m, 2 H) 2.95 (m, 2 H) 3.15 (m, 4 H) 4.13 (s, 3 H) 6.86 (d, J = 2.7 Hz, 1 H) 6.96 (dd, J = .9.1 and 2.7 Hz, 1 H) 7.23 (bs, 1 H) 7.42 (bs, 1 H) 7.51 (d, J = 9.1 1 H) 8.28 (bs, 1 H) 8.75 (s, 1 H) |

TABLE IX

| Code | NMR data |
| --- | --- |
| A21B1C3Z | $^1$H NMR (400 MHz, DMSO-$d_6$) δ ppm 2.1 (s, 3 H) 2.72 (m, 2 H) 2.94 (m, 2 H) 4.06 (s, 3 H) 7.07 (m, 1 H) 7.17 (m, 1 H) 7.47 (d, J = 7.7 Hz, 1 H) 7.81 (d, J = 7.7 Hz, 1 H) 8.26 (s, 1 H) 8.48 (bs, 1 H) 9.73 (bs, 1 H) |
| A35B1C3Z | $^1$H NMR (400 MHz, DMSO-$d_6$) δ ppm 0.94 (d, J = 6.6 Hz, 6 H) 2.09 (m, 1 H) 2.25 (d, J = 7.3 Hz, 2 H) 2.72 (m, 2 H) 2.93 (m, 2 H) 4.06 (s, 3 H) 7.08 (m, 1 H) 7.23 (m, 1 H) 7.40 (d, J = 7.7 Hz, 1 H) 7.84 (d, J = 7.7 Hz, 1 H) 8.26 (s, 1 H) 8.32 (bs, 1 H) 9.72 (bs, 1 H) |
| A37B1C3Z | $^1$H NMR (400 MHz, DMSO-$d_6$) δ ppm 2.72 (m, 2 H) 2.94 (m, 2 H) 3.90 (s, 3 H) 4.10 (s, 3 H) 6.06 (m, 1 H) 6.83 (m, 1 H) 6.97 (m, 1 H) 7.08 (m, 1 H) 7.20 (m, 1 H) 7.59 (m, 1 H) 7.85 (m, 1 H) 8.27 (s, 1 H) 8.58 (s, 3 H) 9.61 (s, 1 H) 12.10 (s, 1 H) |
| A8B1C3Z | $^1$H NMR (400 MHz, DMSO-$d_6$) δ ppm: 2.70 (m, 2 H) 2.92 (m, 2 H) 4.05 (s, 3 H) 6.17 (m, 1 H) 6.91 (bd, 1 H) 6.98 (bd, 1 H) 7.13 (m, 1 H) 7.22 (m, 1 H) 7.52 (d, J = 7.7 Hz, 1 H) 7.87 (d, J = 7.7 Hz, 1 H) 8.25 (s, 1 H) 8.58 (s, 1 H) 9.98 (s, 1 H) 12.10 (s, 1 H) |
| A39B1C3Z | $^1$H NMR (400 MHz, DMSO-$d_6$) δ ppm 2.23 (s, 3 H) 2.32 (s, 3 H) 2.45 (m, 4 H) 2.76 (m, 2 H) 2.95 (m, 2 H) 3.34 (m, 4 H) 4.20 (s, 3 H) 6.57 (d, J = 8.5 Hz, 1 H) 7.83 (bd, J = 8.5 Hz, 1 H) 8.32 (bs, 1 H) 8.41 (s, 1 H) 12.04 (s, 1 H) |
| A45B8C3Z | $^1$H NMR (400 MHz, DMSO-$d_6$) δ ppm 2.74 (m, 2 H) 2.89 (m, 2 H) 7.12 (m, 1 H) 7.36 (m, 2 H) 8.26 (s, 1 H) 8.28 (bs, 1 H) 8.54 (bs, 1 H) 12.10 (s, 1 H) |
| A51B1C3Z | $^1$H NMR (400 MHz, DMSO-$d_6$) δ ppm 2.22 (s, 3 H) 2.44 (m, 4 H) 2.71 (m, 2 H) 2.91 (m, 2 H) 3.13 (m, 4 H) 4.04 (s, 3 H) 6.72 (dd, J = 8.5 and 3.0 Hz, 1 H) 7.18 (dd J = 8.5 and 3.0 Hz, 1 H) 7.36 (d, J = 3.0 Hz, 1 H) 8.26 (bs, 1 H) 8.65 (s, 1 H) |
| A85B1C3Z | $^1$H NMR (400 MHz, DMSO-$d_6$) δ ppm 2.22 (s, 3 H) 2.46 (m, 4 H) 2.72 (m, 2 H) 2.93 (m, 2 H) 3.01 (m, 4 H) 3.79 (s, 3 H) 4.15 (s, 3 H) 6.56 (dd, J = 8.9 and 2.7 Hz, 1 H) 6.90 (d J = 8.9, 1 H) 7.81 (d, J = 2.7 Hz, 1 H) 8.30 (bs, 1 H) 8.55 (s, 1 H) |
| A48B1C3Z | $^1$H NMR (400 MHz, DMSO-$d_6$) δ ppm 2.22 (m, 3 H) 2.42-2.49 (m, 4 H) 2.60 (br s, 2 H) 2.87 (t, J = 7.87 Hz, 2 H) 3.08 (br s, 4 H) 4.04 (s, 3 H) 6.76 (br s, 1 H) 6.87 (br s, 1 H) 7.49-7.56 (m, 1 H) 8.02 (br s, 1 H) 8.57 (br s, 1 H) |
| A90B1C3Z | $^1$H NMR (400 MHz, DMSO-$d_6$) δ ppm 2.24 (m, 3 H) 2.45 (m, 4 H) 2.60 (m, 2 H) 2.87 (m, 2 H) 3.08 (m, 4 H) 4.03 (s, 3 H) 7.01-7.34 (m, 2 H) 8.23 (br s, 1 H) 8.55 (br s, 1 H) |
| A49B1C3Z | $^1$H NMR (400 MHz, DMSO-$d_6$) δ ppm 2.78 (t, 2 H) 2.96 (t, 2 H) 4.16 (s, 3 H) 7.35 (m, 2 H) 8.34 (d, J = 1.83 Hz, 1 H) 8.38 (s, 1 H) 9.11 (s, 1 H) |
| A98B1C3Z | $^1$H NMR (400 MHz, DMSO-$d_6$) δ ppm 2.13 (s, 3 H) 2.21 (s, 3 H) 2.41-2.46 (m, 4 H) 2.69 (t, J = 7.62 Hz, 2 H) 2.92 (t, J = 7.62 Hz, 2 H) 3.02-3.08 (m, 4 H) 4.02 (s, 3 H) 6.65 (dd, J = 8.41, 2.56 Hz, 1 H) 7.04 (d, J = 8.78 Hz, 1 H) 7.07 (d, J = 2.44 Hz, 1 H) 8.21 (s, 1 H) 8.47 (s, 1 H) |
| A80B1C3Z | $^1$H NMR (400 MHz, DMSO-$d_6$) δ ppm 1.35 (s, 9 H) 2.78 (t, J = 7.68 Hz, 2 H) 2.94 (t, J = 7.44 Hz, 2 H) 3.96 (s, 3 H) 7.17-7.26 (m, 3 H) 7.42-7.46 (m, 1 H) 8.27 (s, 1 H) 8.51 (s, 1 H) 12.77 (bs, 1 H) |
| A81B1C3Z | $^1$H NMR (400 MHz, DMSO-$d_6$) δ ppm 2.76 (t, J = 7.68 Hz, 2 H) 2.92 (t, J = 7.74 Hz, 2 H) 4.11 (s, 3 H) 7.20 (dd, J = 8.90 Hz, 2 H) 7.27 (ddd, J = 7.44, 1.22 Hz, 1 H) 7.35 (dd, J = 7.80, 1.60 Hz, 1 H) 7.40 (ddd, J = 7.62, 1.71 Hz, 1 H) 7.45 (dd, J = 8.78, 5.61 Hz, 2 H) 7.64 (d, J = 7.07 Hz, 1 H) 8.24 (s, 1 H) 8.56 (s, 1 H) 12.78 (bs, 1 H) |
| A49B8C3Z | $^1$H NMR (400 MHz, DMSO-$d_6$) δ ppm 2.73 (m, 2 H) 2.90 (m, 2 H) 7.23 (m, 1 H) 7.28 (m, 1 H) 8.28 (bs, 1 H) 8.52 (s, 1 H) 8.77 (bs, 1 H) |
| A51B8C3Z | $^1$H NMR (400 MHz, DMSO-$d_6$) δ ppm 2.22 (s, 3 H) 2.44 (m, 4 H) 2.71 (m, 2 H) 2.91 (m, 2 H) 3.13 (m, 4 H) 6.72 (dd, J = 8.5 and 3.0 Hz, 1 H) 7.18 (dd J = 8.5 and 3.0 Hz, 1 H) 7.36 (d, J = 3.0 Hz, 1 H) 8.26 (bs, 1 H) 8.65 (s, 1 H) |
| A118B1C3Z | $^1$H NMR (400 MHz, DMSO-$d_6$) δ ppm 2.76 (t, J = 7.62 Hz, 2 H) 2.96 (t, J = 7.62 Hz, 2 H) 3.89 (s, 3 H) 4.21 (s, 3 H) 7.02 (d, J = 8.78 Hz, 1 H) 7.15 (dd, J = 8.66, 2.56 Hz, 1 H) 8.03 (s, 1 H) 8.37 (s, 1 H) 8.48 (d, J = 2.44 Hz, 1 H) |

Example 13

8-Iodo-1-methyl-4,5-dihydro-1H-pyrazolo[4,3-h]quinazoline-3-carboxamide

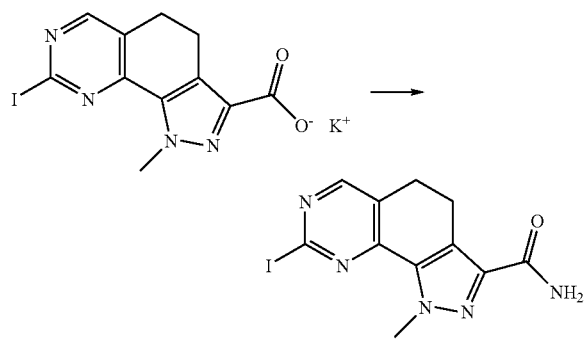

A suspension of potassium 8-iodo-1-methyl-4,5-dihydro-1H-pyrazolo[4,3-h]quinazoline-3-carboxylate (394 mg, 1.0 mmol) in anhydrous dimethylformamide (10 mL) was treated with N-ethyl-N',N'-diisopropyl carbodiimide hydrochloride (EDCI) (287 mg, 1.5 mmol) and with ammonium 1H-1,2,3-benzotriazol-1-ate (304 mg, 2 mmol). The reaction was stirred at room temperature overnight. The reaction was diluted with water and the resulting precipitate was collected by filtration to afford the title compound (320 mg, 90% yield).

$^1$H NMR (400 MHz, DMSO-$d_6$) δ ppm 2.99 (m, 4 H) 4.25 (s, 3 H) 7.31 (s, 1 H) 7.51 (s, 1 H) 8.47 (s, 1 H).

By working according to the above method and using the suitable amine the following compounds were prepared:

8-Amino-1-methyl-1H-pyrazolo[4,3-h]quinazoline-3-carboxamide $^1$H NMR (400 MHz, DMSO-$d_6$) δ ppm 2.68 and 2.90 (2 m, 4 H) 4.28 (s, 3 H) 6.50 (bs, 2 H) 7.32 (bs, 2H) 8.15 (s, 1 H).

8-iodo-1-trityl-4,5-dihydro-1H-pyrazolo[4,3-h]quinazoline-3-carboxamide $^1$H NMR (400 MHz, DMSO-$d_6$) δ ppm: 2.76 (m, 2 H) 3.08 (m, 2 H) 6.63 (s, 1 H) 7.08-7.30 (m, 15 H) 7.43 (s, 1 H) 8.21 (s, 1 H).

8-iodo-1-methyl-4,5-dihydro-1H-pyrazolo[4,3-h]quinazoline-3-carboxylic acid methylamide $^1$H NMR (400 MHz, DMSO-$d_6$) δ ppm 2.75 (d, J=4.63 Hz, 3 H) 2.90 (m, 2 H) 3.03 (m, 2 H) 4.24 (s, 3 H) 6.14 (q, J=4.63 Hz, 1 H)) 8.47 (s, 1H).

TABLE X

| Code | NMR data |
|---|---|
| A8B1C1Z | $^1$H NMR (400 MHz, DMSO-$d_6$) δ ppm 2.80 (m, 2 H) 2.98 (m, 2 H) 4.19 (s, 3 H) 6.17 (m, 1 H) 6.941 (m, 1 H) 6.96 (m, 1 H) 7.16 (m, 1 H) 7.25 (m, 2 H) 7.45 (m, 1 H) 7.52 (dd, J = 7.7 and 1.4 Hz, 1 H) 7.84 (dd, J = 7.7 and 1.4 Hz, 1 H) 8.36 (s, 1 H) 8.69 (s, 1 H) 9.66 (s, 1 H) 11.75 (s, 1 H) |
| A45B8C1Z | $^1$H NMR (400 MHz, DMSO-$d_6$) δ ppm 2.87 (m, 2 H) 3.02 (m, 2 H) 7.10 (m, 1 H) 7.26 (bs, 1 H) 7.40 (m, 2 H) 7.52 (bs, 1 H) 8.31 (m, 1 H) 8.39 (s, 1 H) 8.48 (s, 1 H) 14.02 (s, 1 H) |
| A21B1C1Z | $^1$H NMR (400 MHz, DMSO-$d_6$) δ ppm: 2.09 (s, 3 H) 2.81 (m, 2 H) 2.99 (m, 2 H) 4.18 (s, 3 H) 7.10 (m, 1 H) 7.19 (m, 1 H) 7.25 (bs, 1 H) 7.46 (bs, 1 H) 7.49 (d, J = 7.7 Hz, 1 H) 7.80 (d, J = 7.7 Hz, 1 H) 8.37 (s, 1 H) 8.57 (bs, 1 H) 9.64 (bs, 1 H) |
| A35B1C1Z | $^1$H NMR (400 MHz, DMSO-$d_6$) δ ppm 0.94 (d, J = 6.6 Hz, 6 H) 2.09 (m, 1 H) 2.25 (d, J = 7.3 Hz, 2 H) 2.81 (m, 2 H) 2.98 (m, 2 H) 4.16 (s, 3 H) 7.11 (m, 1 H) 7.23 (m, 1 H) 7.24 (bs, 1 H) 7.42 (d, J = 7.7 Hz, 1 H) 7.46 (bs, 1 H) 7.81 (d, J = 7.7 Hz, 1 H) 8.36 (s, 1 H) 8.46 (s, 1 H) 9.67 (bs, 1 H) |
| A37B1C1Z | $^1$H NMR (400 MHz, DMSO-$d_6$) δ ppm 2.80 (m, 2 H) 2.97 (m, 2 H) 3.88 (s, 3 H) 4.18 (s, 3 H) 6.10 (m, 1 H) 6.89 (m, 1 H) 7.02 (m, 1 H) 7.15 (m, 1 H) 7.24 (m, 1 H) 7.25 (m, 1 H) 7.46 (m, 1 H) 7.52 (m, 1 H) 7.81 (m, 1 H) 8.36 (s, 1 H) 8.68 (s, 3 H) 9.56 (s, 1 H) |
| A51B1C1Z | $^1$H NMR (400 MHz, DMSO-$d_6$) δ ppm 2.22 (s, 3 H) 2.44 (m, 4 H) 2.80 (m, 2 H) 2.97 (m, 2 H) 3.12 (m, 4 H) 4.16 (s, 3 H) 6.75 (dd, J = 9.2 and 3.0 Hz, 1 H) 7.19 (dd J = 9.2 and 3.0 Hz, 1 H) 7.24 (bs, 1 H) 7.30 (d, J = 3.0 Hz, 1 H) 7.43 (bs, 1 H) 8.35 (s, 1 H) 8.87 (s, 1 H) |
| A51B1C4Z | $^1$H NMR (400 MHz, DMSO-$d_6$) δ ppm 2.26 (s, 3 H) 2.46-2.52 (m, 4 H) 2.74 (d, J = 4.76 Hz, 3 H) 2.81 (t, J = 7.74 Hz, 2 H) 2.98 (t, J = 7.74 Hz, 2 H) 3.13-3.18 (m, 4 H) 4.17 (s, 3 H) 6.77 (dd, J = 9.02, 3.05 Hz, 1 H) 7.19-7.23 (m, 1 H) 7.31 (d, J = 2.93 Hz, 1 H) 8.07 (q, J = 4.59 Hz, 1 H) 8.36 (s, 1 H) 8.89 (s, 1 H) |
| A51B1C7Z | $^1$H NMR (400 MHz, DMSO-$d_6$) δ ppm 2.22 (s, 3 H) 2.42-2.46 (m, 4 H) 2.82 (t, J = 7.68 Hz, 2 H) 2.98 (t, J = 7.62 Hz, 2 H) 3.11-3.16 (m, 4 H) 3.93-4.05 (m, 2 H) 4.19 (s, 3 H) 6.76 (dd, J = 9.02, 2.80 Hz, 1 H) 7.20 (d, J = 8.54 Hz, 1 H) 7.30 (d, J = 2.80 Hz, 1 H) 8.36 (s, 1 H) 8.71 (t, J = 6.46 Hz, 1 H) 8.91 (s, 1 H) |
| A85B1C1Z | $^1$H NMR (400 MHz, DMSO-$d_6$) δ ppm: 2.23 (s, 3 H) 2.46 (m, 4 H) 2.81 (m, 2 H) 2.99 (m, 2 H) 3.02 (m, 4 H) 3.79 (s, 3 H) 4.27 (s, 3 H) 6.59 (dd, J = 8.9 and 2.9 Hz, 1 H) 6.92 (d J = 8.9, 1 H) 7.26 (bs, 1 H) 7.46 (bs, 1 H) 7.73 (d, J = 2.9 Hz, 1 H) 8.07 (s, 1 H) 8.39 (s, 1 H) |
| A85B1C4Z | $^1$H NMR (400 MHz, DMSO-$d_6$) δ ppm 2.35 (m, 3 H) 2.62 (m, 4 H) 2.75 (d, J = 4.76 Hz, 3 H) 2.81 (t, J = 7.62 Hz, 2 H) 2.99 (t, J = 7.74 Hz, 2 H) 3.06 (m, 4 H) 3.79 (s, 3 H) 4.27 (s, 3 H) 6.61 (dd, J = 8.84, 2.87 Hz, 1 H) 6.93 (d, J = 8.90 Hz, 1 H) 7.73 (d, J = 2.80 Hz, 1 H) 8.07 (m, 1 H) 8.09 (s, 1 H) 8.39 (s, 1 H) |

TABLE X-continued

| Code | NMR data |
|---|---|
| A39B1C4Z | $^1$H NMR (400 MHz, DMSO-$d_6$) δ ppm: 2.29 (s, 3 H) 2.45 (m, 4 H) 2.75 (d, J = 4.76 Hz, 3 H) 2.85 (t, J = 7.8 Hz, 2 H) 3.00 (t, J = 7.8 Hz, 2 H) 3.41 (m, 4 H) 4.33 (s, 3 H) 6.60 (dd, J = 9.2 and 2.3 Hz, 1 H) 7.85 (d, J = 9.2 Hz, 1 H) 8.10 (m, 1H) 8.32 (d, J = 2.3 Hz, 1 H) 8.51 (s, 1 H) |
| A48B1C1Z | $^1$H NMR (400 MHz, DMSO-$d_6$) δ ppm 2.23 (s, 3 H) 2.46 (m, 4 H) 2.77 (t, J = 7.68 Hz, 2 H) 2.95 (t, J = 7.68 Hz, 2 H) 3.15 (m, 4 H) 4.13 (s, 3 H) 6.86 (bs, 1 H) 6.96 (dd, J = 8.62, 2.50 Hz, 1 H) 7.23 (bs, 1 H) 7.42 (s, 1 H) 7.51 (d, J = 8.62 Hz, 1 H) 8.28 (s, 1 H) |
| A48B1C4Z | $^1$H NMR (400 MHz, DMSO-$d_6$) δ ppm 2.27 (s, 3 H) 2.52 (m, 4 H) 2.74 (d, J = 4.76 Hz, 3 H) 2.78 (t, J = 7.62 Hz, 2 H) 2.97 (t, J = 7.62 Hz, 2 H) 3.17 (m, 4 H) 4.15 (s, 3 H) 6.88 (m, 1 H) 6.98 (dd, J = 8.96, 2.74 Hz, 1 H) 7.53 (d, J = 9.02 Hz, 1 H) 8.05 (q, J = 4.67 Hz, 1 H) 8.29 (s, 1 H) 8.77 (s, 1 H) |
| A89B1C6Z | $^1$H NMR (400 MHz, DMSO-$d_6$) δ ppm 2.23 (s, 3 H) 2.46 (m, 4 H) 2.77 (m, 4 H) 2.97 (s, 3 H) 3.12 (m, 4 H) 3.21 (s, 3 H) 3.80 (s, 3 H) 4.20 (s, 3 H) 6.49 (dd, J = 8.78, 2.56 Hz, 1 H) 6.63 (d, J = 2.56 Hz, 1 H) 7.65 (d, J = 8.78 Hz, 1 H) 7.99 (s, 1 H) 8.28 (s, 1 H) |
| A89B1C4Z | $^1$H NMR (400 MHz, DMSO-$d_6$) δ ppm 2.27 (s, 3 H) 2.52 (m, 4 H) 2.74 (d, J = 4.76 Hz, 3 H) 2.78 (t, J = 7.62 Hz, 2 H) 2.97 (t, J = 7.62 Hz, 2 H) 3.17 (m, 4 H) 3.80 (s, 3 H) 4.15 (s, 3 H) 6.49 (dd, J = 8.78, 2.56 Hz, 1 H) 6.63 (d, J = 2.56 Hz, 1 H) 7.65 (d, J = 8.78 Hz, 1 H) 7.99 (s, 1 H) 8.05 (q, J = 4.67 Hz, 1 H) 8.28 (s, 1 H) 8.77 (s, 1 H) |
| A89B1C1Z | $^1$H NMR (400 MHz, DMSO-$d_6$) δ ppm 2.31 (bs, 3 H) 2.54-2.62 (m, 4 H) 2.78 (t, J = 7.68 Hz, 2 H) 2.94-3.00 (m, 2 H) 3.12-3.19 (m, 4 H) 3.82 (s, 3 H) 4.23 (s, 3 H) 6.51 (dd, J 8.72, 2.50 Hz, 1 H) 6.65 (d, J = 2.44 Hz, 1 H) 7.24 (bs, 1 H) 7.44 (s, 1 H) 7.66 (d, J = 8.78 Hz, 1 H) 8.01 (s, 1 H) 8.30 (s, 1 H) |
| A49B1C1Z | $^1$H NMR (400 MHz, DMSO-$d_6$) δ ppm 2.83 (t, J = 7.74 Hz, 2 H) 2.96-3.02 (m, 2 H) 4.24 (s, 3 H) 7.26 (br s, 1 H) 7.36 (d, J = 1.10 Hz, 1 H) 7.46 (bs, 1 H) 8.29 (dd, J = 1.59, 0.98 Hz, 1 H) 8.44 (s, 1 H) 9.26 (s, 1 H) |
| A98B1C1Z | $^1$H NMR (400 MHz, DMSO-$d_6$) δ ppm 2.13 (s, 3 H) 2.21 (s, 3 H) 2.41-2.45 (m, 4 H) 2.77 (t, J = 7.82 Hz, 2 H) 2.96 (t, J = 7.82 Hz, 2 H) 3.03-3.07 (m, 4 H) 4.11-4.14 (m, 3 H) 6.67 (dd, J = 8.35, 2.62 Hz, 1 H) 7.06 (d, J = 8.30 Hz, 1 H) 7.04 (d, J = 2.40 Hz, 1 H) 7.23 (bs, 1 H) 7.42 (bs, 1 H) 8.30 (s, 1 H) 8.64 (s, 1 H) |
| A49B7C1Z | $^1$H NMR (400 MHz, DMSO-$d_6$) δ ppm 1.27 (t, J = 7.13 Hz, 3 H) 2.83 (t, J = 7.62 Hz, 2 H) 2.93-3.06 (m, 2 H) 4.61 (q, J = 7.07 Hz, 2 H) 7.26 (bs, 1 H) 7.39-7.46 (m, 3 H) 8.09 (d, J = 2.20 Hz, 1 H) 8.43 (s, 1 H) 9.25 (s, 1 H) |
| A49B8C1Z | $^1$H NMR (400 MHz, DMSO-$d_6$) δ ppm 2.83 (t, J 7.74 Hz, 2 H) 2.98 (m, 2 H) 7.26 (bs, 1 H) 7.36 (d, J 1.10 Hz, 1 H) 7.46 (bs, 1 H) 8.29 (dd, J 1.59, 0.98 Hz, 1 H) 8.44 (s, 1 H) 9.26 (s, 1 H) |
| A118B1C1Z | $^1$H NMR (400 MHz, DMSO-$d_6$) δ ppm 2.84 (t, J = 7.68 Hz, 2 H) 3.00 (t, J = 7.68 Hz, 2 H) 3.88 (s, 3 H) 4.32 (s, 3 H) 7.03 (d, J = 8.78 Hz, 1 H) 7.18 (dd, J = 8.66, 2.56 Hz, 1 H) 7.27 (br. s., 1 H) 7.47 (br. s., 1 H) 8.22 (s, 1 H) 8.40 (d, J = 2.56 Hz, 1 H) 8.46 (s, 1 H) |
| A118B1C8Z | $^1$H NMR (400 MHz, DMSO-$d_6$) δ ppm 2.84 (t, J = 7.72 Hz, 2 H) 3.00 (t, J = 7.72 Hz, 2 H) 3.75 (s, 3 H) 3.82 (s, 3 H) 3.88 (s, 3 H) 4.32-4.36 (m, 2 H) 4.33 (s, 3 H) 6.48 (dd, J = 8.35, 2.38 Hz, 1 H) 6.57 (d, J = 2.44 Hz, 1 H) 7.03 (d, J = 8.78 Hz, 1 H) 7.09 (d, J = 8.29 Hz, 1 H) 7.18 (dd, J = 8.66, 2.44 Hz, 1 H) 8.20-8.23 (m, 1 H) 8.23 (s, 1 H) 8.39 (d, J = 2.44 Hz, 1 H) 8.46 (s, 1 H) |
| A85B1C8Z | $^1$H NMR (400 MHz, DMSO-$d_6$) δ ppm 2.23 (s, 3 H) 2.43-2.49 (m, 4 H) 2.77-2.85 (m, 2 H) 2.96-3.00 (m, 2 H) 3.01-3.04 (m, 4 H) 4.28 (s, 3 H) 4.34 (d, J = 6.22 Hz, 2 H) 6.48 (dd, J = 8.35, 2.38 Hz, 1 H) 6.57 (d, J = 2.32 Hz, 1 H) 6.60 (dd, J = 8.90, 2.93 Hz, 1 H) 6.92 (d, J = 8.78 Hz, 1 H) 7.09 (d, J = 8.41 Hz, 1 H) 7.72 (d, J = 2.80 Hz, 1 H) 8.08 (s, 1 H) 8.20 (t, J = 6.10 Hz, 1 H) 8.40 (s, 1 H) |

Example 14

8-Iodo-4,5-dihydro-1H-pyrazolo[4,3-h]quinazoline-3-carboxamide

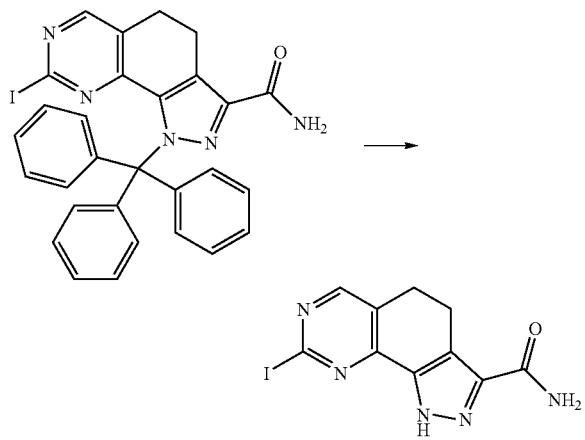

8-Iodo-1-trityl-4,5-dihydro-1H-pyrazolo[4,3-h]quinazoline-3-carboxamide (291 mg, 0.5 mmol) in DCM (10 mL) was treated with trifluoroacetic acid (0.5 mL). The resulting mixture was stirred at room temperature for 1 hour. DCM (40 mL) was added and the organic phase was washed with saturated solution of sodium hydrogen carbonate, then with brine, dried over sodium sulfate and concentrated. The crude solid was purified by flash chromatography on silica gel (eluant: DCM/EtOH 90/10) to afford 143 mg of the title compound (84% yield).

$^1$H NMR (400 MHz, DMSO-$d_6$) δ ppm 2.93 (m, 2H) 3.04 (m, 2H) 7.27 (s, 1H) 7.58 (s, 1H) 8.44 (s, 1H) 14.25 (s, 1H).

By working according to this method, the following compound was prepared:

TABLE XI

| Code | NMR data |
|---|---|
| A51B8C1Z | $^1$H NMR (400 MHz, DMSO-$d_6$) δ ppm: 2.22 (s, 3 H) 2.45 (m, 4 H) 2.84 (m, 2 H) 2.99 (m, 2 H) 3.17 (m, 4 H) |

TABLE XI-continued

| Code | NMR data |
|---|---|
| | 6.71 (m, 1 H) 7.17 (m, 1 H) 7.22 (bs, 1 H) 7.29 (m, 1 H) 7.49 (bs, 1 H) 7.61 (bs, 1 H) 8.31 (bs, 1 H) 8.36 (s, 1 H) 13.94 (bs, 1 H) |

Example 15

8-Iodo-1-(2-fluoroethyl)-4,5-dihydro-1H-pyrazolo[4,3-h]quinazoline-3-carboxamide

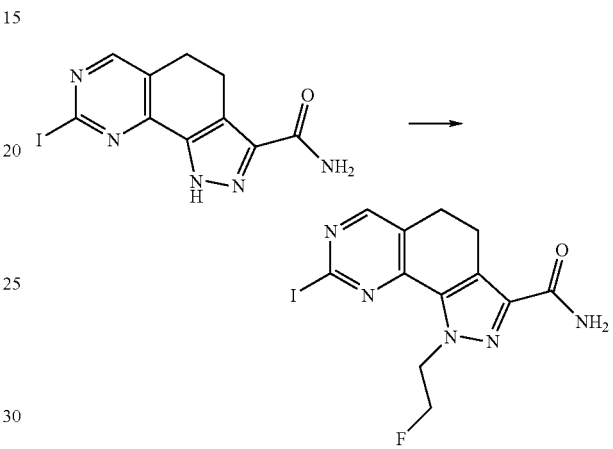

A mixture of 8-iodo-4,5-dihydro-1H-pyrazolo[4,3-h]quinazoline-3-carboxamide (104 mg, 0.3 mmol) in THF (3 mL) was treated with triphenylphosphine supported on resin (0.4 g, 3 mmol/g, 1.2 mmol), di-t-butylazadicarboxylate (276 mg, 1.2 mmol), 2-fluoroethanole (70 microL, 1.2 mmol) for 1 h at room temperature. The resine was filtered off and the solution was concentrated. Crystallization from diethyl ether gave 74 mg of the title compound (62% yield).

$^1$H NMR (400 MHz, DMSO-$d_6$) δ ppm 2.92 (m, 2 H) 3.05 (m, 2 H) 4.86 (m, 1 H) 4.96 (m, 2 H) 5.05 (m, 1 H) 7.36 (s, 1 H) 7.55 (s, 1 H) 8.49 (s, 1 H).

By working according to the above method and using the suitable alcohol the following compounds were prepared:

TABLE XII

| Code | NMR data |
|---|---|
| A45B2C1Z | $^1$H NMR (400 MHz, DMSO-$d_6$) δ ppm 2.82 (m, 2 H) 2.99 (m, 2 H) 4.57 (m, 1 H) 4.69 (m, 1 H) 4.85 (m, 1 H) 4.91 (m, 1 H) 7.26 (m, 1 H) 7.29 (bs, 1 H) 7.40 (m, 2 H) 7.45 (bs, 1 H) 7.76 (m, 1 H) 8.38 (s, 1 H) 9.10 (s, 1 H) |
| A45B3C1Z | $^1$H NMR (400 MHz, DMSO-$d_6$) δ ppm 1.29 (d, J = 6.71 Hz, 6 H) 2.78 (m, 2 H) 2.95 (m, 2 H) 4.60 (m, 1 H) 7.23 (bs, 1 H) 7.27 (m, 1 H) 7.31 (bs, 1 H) 7.40 (m, 2 H) 7.73 (m, 1 H) 8.36 (s, 1 H) 9.06 (s, 1 H) |
| A45B4C1Z | $^1$H NMR (400 MHz, DMSO-$d_6$) δ ppm 1.33 (m, 6 H) 2.79 (m, 2 H) 2.98 (m, 2 H) 3.26 (m, 1 H) 3.39 (m, 1 H) 3.64 (m, 1 H) 3.80 (m, 1 H) 4.41 (m, 1 H) 4.74 (m, 1 H) 4.90 (m, 1 H) 7.22 (m, 1 H) 7.25 (bs, 1 H) 7.39 (m, 2 H) 7.42 (bs, 1 H) 7.87 (m, 1 H) 8.38 (s, 1 H) 9.03 (s, 1 H) |
| A51B2C1Z | $^1$H NMR (400 MHz, DMSO-$d_6$) δ ppm 2.42 (s, 3 H) 2.68 (m, 4 H) 2.82 (m, 2 H) 2.99 (m, 2 H) 3.22 (m, 4 H) 4.54 (m, 1 H) 4.66 (m, 1 H) 4.83 (m, 1 H) 4.90 (m, 1 H) 6.83 (m, 1 H) 7.20 (m, 1 H) 7.25 (m, 1 H) 7.29 (bs, 1 H) 7.43 (bs, 1 H) 8.36 (s, 1 H) 8.99 (s, 1 H) |

TABLE XII-continued

| Code | NMR data |
|---|---|
| A51B7C1Z | ¹H NMR (400 MHz, DMSO-$d_6$) δ ppm 1.15 (t, 3 H) 2.42 (s, 3 H) 2.64 (m, 4 H) 2.82 (m, 2 H) 2.97 (m, 2 H) 3.22 (m, 4 H) 4.54 (q, 2 H) 6.86 (m, 1 H) 7.22 (m, 1 H) 7.25 (m, 1 H) 7.28 (bs, 1 H) 7.38 (bs, 1 H) 8.35 (s, 1 H) 8.98 (s, 1 H) |
| A49B4C1Z | ¹H NMR (400 MHz, DMSO-$d_6$) δ ppm 1.33 (m, 6 H) 2.79 (m, 2 H) 2.98 (m, 2 H) 3.27 (m, 2 H) 3.71 (m, 1 H) 3.87 (m, 1 H) 4.42 (m, 1 H) 4.80 (m, 1 H) 4.98 (m, 1 H) 7.28 (m, 1 H) 7.38 (bs, 2 H) 7.45 (m, 2 H) 8.19 (s, 1 H) 8.45 (s, 1 H) 9.25 (s, 1 H) |
| A51B4C1Z | ¹H NMR (400 MHz, DMSO-$d_6$) δ ppm 1.33 (m, 6 H) 2.54 (m, 5 H) 2.77-2.81 (m, 2 H) 2.93-3.03 (m, 2 H) 3.12-3.27 (m, 5 H) 3.37-3.46 (m, 1 H) 3.55-3.65 (m, 1 H) 3.71-3.82 (m, 1 H) 4.37 (t, J = 2.87 Hz, 1 H) 4.66-4.77 (m, 1 H) 4.84-4.94 (m, 1 H) 6.80 (dd, J = 9.21, 2.99 Hz, 1 H) 7.22 (d, J = 9.02 Hz, 1 H) 7.25-7.28 (m, 2 H) 7.36-7.43 (m, 1 H) 8.36 (s, 1 H) 8.88 (s, 1 H) |

Example 16

8-[(2-acetylphenyl)amino]-1-methyl-4,5-dihydro-1H-pyrazolo[4,3-h]quinazoline-3-carboxamide (A2B1C1Z)

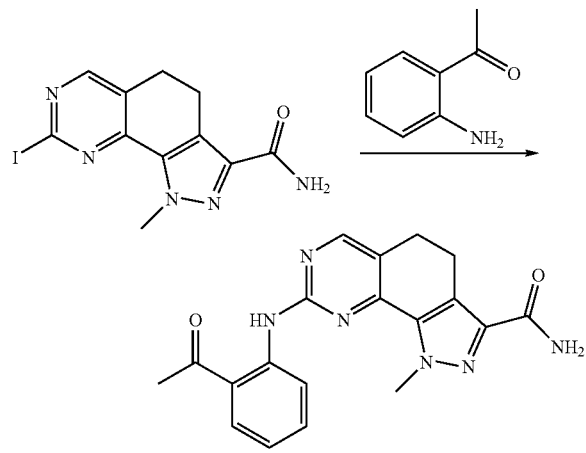

Palladium acetate Pd(OAc)$_2$ (20 mg, 0.09 mmol), (±)-BINAP (55 mg, 0.09 mmol) and dimethylformamide (5 mL) were charged in a round-bottom flask flushed with argon. The flask was evacuated and backfilled with argon. The mixture was stirred under argon for 30 minutes and added to a mixture of 2-acetylaniline (0.162 ml, 1.35 mmol), 8-iodo-1-methyl-4,5-dihydro-1H-pyrazolo[4,3-h]quinazoline-3-carboxamide (319 mg, 0.9 mmol), potassium carbonate (1.24 g, 9 mmol) in dimethylformamide (10 mL). The resulting mixture was stirred at 80° C. for 4 hours under argon. After cooling to room temperature, the reaction mixture was filtered on a pad of celite. The solvent was concentrated, the crude solid was purified by flash chromatography on silica gel (eluant: DCM/EtOH 90/10) to afford 153 mg (47% yield) of the title compound.

¹H NMR (400 MHz, DMSO-$d_6$) δ ppm 2.69 (s, 3 H) 2.87 (t, J=7.68 Hz, 2 H) 3.02 (t, J=7.68 Hz, 2 H) 4.36 (s, 3H) 7.10 (ddd, J=8.08, 7.10, 1.16 Hz, 1 H) 7.28 (s, 1H) 7.51 (s, 1 H) 7.65 (ddd, J=8.54, 7.19, 1.46 Hz, 1 H) 8.08 (dd, J=7.99, 1.52 Hz, 1 H) 8.52 (s, 1 H) 8.75 (dd, J=8.54, 0.98 Hz, 1 H) 11.61 (s, 1 H)

By working according to the same procedure the following compounds were prepared:

TABLE XIII

| Code | NMR data |
|---|---|
| A1B1C1Z | ¹H NMR (400 MHz, DMSO-$d_6$) δ ppm 2.04 (t, J = 7.70 Hz, 2 H) 3.01 (t, J = 7.70 Hz, 2 H) 4.21 (s, 3 H) 7.26 (m, 1 H) 7.27 (bs, 1 H) 7.47 (bs, 1 H) 7.73 (m, 1 H) 7.89 (m, 1 H) 8.12 (m, 2 H) 10.02 (s, 1 H) |
| A34B1C1Z | ¹H NMR (400 MHz, DMSO-$d_6$) δ ppm 2.87 (t, J = 7.70 Hz, 2 H) 3.01 (t, J = 7.70 Hz, 2 H) 3.27 (s, 3 H) 4.27 (s, 3 H) 7.25-7.30 (bs, 1 H) 7.27 (m, 1 H) 7.47-7.52 (bs, 1 H) 7.74 (m, 1 H) 7.89 (m, 1 H) 8.49 (m, 1 H) 8.51 (m, 1 H) 9.23 (s, 1 H) |
| A39B2C1Z | ¹H NMR (400 MHz, DMSO-$d_6$) δ ppm 2.23 (s, 3 H) 2.45 (m, 4 H) 2.54 (s, 3 H) 2.86 (m, 2 H) 3.02 (m, 2 H) 3.34 (m, 4 H) 4.87 (m, 1 H) 4.99 (m, 1 H) 5.06 (m, 1 H) 5.13 (m, 1 H) 6.61 (dd, J = 9.2 and 2.5 Hz, 1 H) 7.33 (bs, 1 H) 7.50 (bs, 1 H) 7.88 (bd, J = 9.2 Hz, 1 H) 8.33 (d, 2.5 Hz, 1 H) 8.53 (s, 1 H) 12.15 (s, 1 H) |
| A40B2C1Z | ¹H NMR (400 MHz, DMSO-$d_6$) δ ppm 2.23 (s, 3 H) 2.46 (m, 4 H) 2.52 (s, 3 H) 2.82 (m, 2 H) 2.93 (m, 4 H) 3.01 (m, 2 H) 4.66 (m, 1 H) 4.78 (m, 1 H) 4.91 (m, 1 H) 4.97 (m, 1 H) 7.01 (d, J = 8.0 Hz, 1 H) 7.31 (bs, 1 H) 7.42 (t, J = 8.0 Hz, 1 H) 7.47 (bs, 1 H) 7.53 (d, J = 8.0 Hz, 1 H) 8.37 (s, 1 H) 9.01 (s, 1 H) |
| A2B2C1Z | ¹H NMR (400 MHz, DMSO-$d_6$) δ ppm 2.68 (s, 3 H) 2.87 (m, 2 H) 3.02 (m, 2 H) 4.88 (m, 1 H) 4.99 (m, 1 H) 5.08 (m, 1 H) 5.13 (m, 1 H) 7.10 (m, 1 H) 7.33 (bs, 1 H) 7.50 (bs, 1 H) 7.65 (m, 1 H) 8.07 (dd, J = 8.05 and 1.5 Hz, 1 H) 8.51 (s, 1 H) 8.62 (dd, J = 8.54 and 0.9 Hz, 1 H) 11.54 (s, 1 H) |

TABLE XIII-continued

| Code | NMR data |
|---|---|
| A84B1C1Z | $^1$H NMR (400 MHz, DMSO-$d_6$) δ ppm 2.26 (s, 3 H) 2.47-2.55 (m, 4 H) 2.66 (s, 3 H) 2.83 (t, J = 7.68 Hz, 2 H) 3.00 (t, J = 7.68 Hz, 2 H) 3.14-3.19 (m, 4 H) 4.32 (s, 3 H) 7.27 (bs, 1 H) 7.32 (dd, J = 9.15, 2.68 Hz, 1 H) 7.45 (d, J = 2.80 Hz, 1 H) 7.48 (bs, 1 H) 8.43 (s, 1 H) 8.49 (d, J = 9.15 Hz, 1 H) 11.04 (s, 1 H) |
| A39B1C1Z | $^1$H NMR (400 MHz, DMSO-$d_6$) δ ppm 2.23 (s, 3 H) 2.45 (m, 4 H) 2.55 (s, 3 H) 2.85 (t, J = 7.8 Hz, 2 H) 3.00 (t, J = 7.8 Hz, 2 H) 3.35 (m, 4 H) 4.35 (s, 3 H) 6.63 (dd, J = 9.2 and 2.5 Hz, 1 H) 7.29 (bs, 1 H) 7.49 (bs, 1 H) 7.88 (bd, J = 9.2 Hz, 1 H) 8.33 (d, J = 2.5 Hz, 1 H) 8.53 (s, 1 H) 12.13 (s, 1 H) |
| A40B1C1Z | $^1$H NMR (400 MHz, DMSO-$d_6$) δ ppm 2.23 (s, 3 H) 2.46 (m, 4 H) 2.57 (s, 3 H) 2.81 (t, J = 7.32 Hz, 2 H) 2.93 (m, 4 H) 3.99 (t, J = 7.68 Hz, 2 H) 4.24 (s, 3 H) 6.96 (dd, J = 8.17 Hz, 1 H) 7.27 (bs, 1 H) 7.41 (t, J = 8.17 Hz 1 H) 7.46 (bs, 1 H) 7.71 (bd, J = 8.17 Hz, 1 H) 8.37 (s, 1 H) 9.05 (s, 1 H) |
| A51B6C1Z | $^1$H NMR (400 MHz, DMSO-$d_6$) δ ppm 2.23 (s, 3 H) 2.45 (m, 4 H) 2.72 (t, J = 7.50 Hz, 2 H) 3.06 (m, 2 H) 3.09 (m, 4 H) 6.55 (m, 2 H) 7.08 (m, 6 H) 7.14 (d, J = 9.02 Hz, 1 H) 7.23 (m, 9 H) 7.40 (bs, 1 H) 7.96 (d, J = 2.93 Hz, 1 H) 8.26 (s, 1 H) |
| A41B1C1Z | $^1$H NMR (400 MHz, DMSO-$d_6$) δ ppm 1.62 (m, 2 H) 1.78 (m, 2 H) 2.02 (m, 2 H) 2.21 (bs, 3 H) 2.81 (m, 2 H) 2.84 (t, J = 7.74 Hz 2 H) 2.99 (t, J = 7.68 Hz 2 H) 3.75 (m, 1 H) 4.24 (s, 3 H) 7.25 (bs, 1 H) 7.46 (bs, 1 H) 7.88 (m, 2 H) 8.13 (d, J = 8.54 Hz, 1 H) 8.31 (d, J = 7.68 Hz, 1 H) 8.44 (s, 1 H) 9.25 (s, 1 H) |
| A42B1C1Z | $^1$H NMR (400 MHz, DMSO-$d_6$) δ ppm 1.70 (m, 2 H) 1.91 (m, 2 H) 2.50 (s, 3 H) 2.84 (t, J = 7.80 Hz, 1 H) 3.01 (t, J = 7.80 Hz, 2 H) 3.88 (m, 1 H) 3.94 (s, 3 H) 4.32 (s, 3 H) 7.26 (bs, 1 H) 7.46 (bs, 1 H) 7.52 (m, 2 H) 8.20 (m, 1 H) 8.25 (m, 1 H) 8.45 (s, 1 H) 9.22 (s, 1H) |
| A44B1C1Z | $^1$H NMR (400 MHz, DMSO-$d_6$) δ ppm 2.86 (t, J = 7.68 Hz, 2 H) 3.00 (t, J = 7.8 Hz 2 H) 4.24 (s, 3 H) 7.26 (bs, 1 H) 7.47 (bs, 1 H) 7.70 (dq, J = 9.08 and 2.87 Hz, 1 H) 8.01 (dd, J = 9.07 and 1.61 Hz, 1 H) 8.50 (s, 1 H) 8.99 (d, J = 2.80 Hz, 1 H) 9.53 (s, 1 H) |
| A47B1C1Z | $^1$H NMR (400 MHz, DMSO-$d_6$) δ ppm 2.81 (t, J = 7.74 Hz, 2 H) 2.97 (t, J = 7.8 Hz, 2 H) 3.84 (s, 3 H) 4.28 (s, 3 H) 4.44 (d, J = 5.37 Hz, 2 H) 5.05 (t, J = 5.55 Hz, 1 H) 6.94-6.97 (m, 1 H) 6.99 (m, 1 H) 7.25 (bs, 1 H) 7.45 (bs, 1 H) 8.07 (m, 2 H) 8.39 (s, 1 H) |
| A113B1C1Z | $^1$H NMR (400 MHz, DMSO-$d_6$) δ ppm 2.76 (br. s., 2 H) 2.80-2.85 (m, 2 H) 2.91 (d, J = 4.51 Hz, 3 H) 2.95-3.02 (m, 2 H) 3.21-3.34 (m, 1 H) 3.63 (d, J = 10.36 Hz, 1 H) 3.73-3.82 (m, 1 H) 3.96-4.05 (m, 1 H) 4.14 (s, 3 H) 6.22 (br. s., 1 H) 7.28 (br. s., 1 H) 7.32-7.35 (m, 1 H) 7.37 (br. s., 1 H) 7.40-7.45 (m, 1 H) 7.93 (d, J = 2.19 Hz, 1 H) 8.38 (s, 0 H) 9.15 (s, 1 H) |
| A114B1C1Z | $^1$H NMR (400 MHz, DMSO-$d_6$) δ ppm 1.73-1.89 (m, 2 H) 1.99-2.08 (m, 2 H) 2.78-2.86 (m, 2 H) 2.82 (d, J = 4.63 Hz, 3 H) 2.99 (t, J = 7.50 Hz, 2 H) 3.03-3.15 (m, 2 H) 3.49-3.57 (m, 2 H) 4.17 (s, 3 H) 7.09 (dd, J = 8.54, 2.11 Hz, 1 H) 7.28 (br. s., 1 H) 7.38 (dd, J = 9.45, 1.04 Hz, 1 H) 7.40 (br. s., 1 H) 7.72 (d, J = 2.11 Hz, 1 H) 8.38 (s, 1 H) 9.07 (s, 1 H) |
| A49B6C1Z | $^1$H NMR (400 MHz, DMSO-$d_6$) δ ppm 2.72-2.78 (m, 2 H) 3.06-3.12 (m, 2 H) 6.26 (s, 1 H) 6.56 (br. s., 1 H) 7.08 (m, 6 H) 7.23 (m, 10 H) 7.33 (m, 1 H) 7.41 (br. s., 1 H) 8.33 (s, 1 H) 8.59 (d, J = 2.44 Hz, 1 H) |
| A116B1C1Z | $^1$H NMR (400 MHz, DMSO-$d_6$) δ ppm 2.04 (s, 3 H) 2.22 (s, 3 H) 2.45 (br. s., 4 H) 2.78-2.85 (m, 2 H) 2.95-3.03 (m, 2 H) 3.05-3.12 (m, 4 H) 4.19 (s, 3 H) 6.70 (dd, J = 8.72, 2.74 Hz, 1 H) 7.22 (d, J = 9.02 Hz, 1 H) 7.25 (br. s., 1 H) 7.34 (d, J = 2.80 Hz, 1 H) 7.45 (br. s., 1 H) 8.35 (s, 1 H) 8.46 (s, 1 H) 9.50 (s, 1 H) |
| A119B1C1Z | $^1$H NMR (400 MHz, DMSO-$d_6$) δ ppm 2.79-2.84 (m, 2 H) 2.87 (s, 3 H) 2.95-3.02 (m, 2 H) 4.17 (s, 3 H) 4.47 (s, 2 H) 6.82 (dd, J = 9.15, 2.93 Hz, 1 H) 7.25-7.29 (m, 1 H) 7.32 (d, J = 3.05 Hz, 1 H) 7.23-7.40 (m, 5 H) 8.36 (s, 1 H) 9.00 (s, 1 H) |
| A120B1C1Z | $^1$H NMR (400 MHz, DMSO-$d_6$) δ ppm 2.79-2.84 (m, 2 H) 2.87 (s, 3 H) 2.95-3.02 (m, 2 H) 4.17 (s, 3 H) 4.47 (s, 2 H) 6.82 (dd, J = 9.15, 2.93 Hz, 1 H) 7.25-7.29 (m, 1 H) 7.32 (d, J = 3.05 Hz, 1 H) 7.23-7.40 (m, 5 H) 8.36 (s, 1 H) 9.00 (s, 1 H) |

The tables below show the analytical HPLC/Mass data for some representative compounds of the invention.

TABLE XIV

| Code | M + H | RT | METHOD |
|---|---|---|---|
| A3B1C1Z | 389.13 | 2.2 | 4 |
| A4B1C1Z | 335.16 | 2.0 | 4 |
| A5B1C1Z | 339.14 | 2.0 | 4 |
| A6B1C1Z | 351.16 | 1.5 | 4 |
| A9B1C1Z | 425.17 | 2.7 | 4 |
| A19B1C1Z | 364.15 | 1.5 | 4 |

TABLE XIV-continued

| Code | M + H | RT | METHOD |
|---|---|---|---|
| A18B1C1Z | 419.23 | 2.1 | 4 |
| A10B1C1Z | 397.18 | 2.5 | 4 |
| A11B1C1Z | 346.14 | 1.7 | 4 |
| A13B1C1Z | 400.12 | 1.5 | 4 |
| A14B1C1Z | 446.27 | 3.8 | 4 |
| A15B1C1Z | 440.18 | 2.3 | 4 |
| A16B1C1Z | 406.20 | 2.1 | 4 |
| A17B1C1Z | 386.17 | 2.3 | 4 |
| A22B1C1Z | 411.19 | 2.6 | 4 |
| A26B1C1Z | 436.19 | 1.38 | 3 |
| A20B1C1Z | 429.15 | 1.65 | 3 |
| A24B1C1Z | 345.14 | 1.8 | 4 |
| A27B1C1Z | 350.17 | 1.8 | 4 |
| A28B1C1Z | 363.19 | 2.4 | 4 |
| A29B1C1Z | 367.13 | 2.2 | 4 |
| A45B1C1Z | 405.13 | 2.4 | 4 |
| A33B1C1Z | 379.15 | 2.4 | 4 |
| A32B1C1Z | 413.17 | 2.7 | 4 |
| A30B1C1Z | 412.19 | 2.5 | 4 |
| A31B1C1Z | 357.13 | 1.8 | 4 |
| A105B1C1Z | 351.37 | 2.4 | 4 |
| A106B1C1Z | 353.36 | 2.3 | 4 |

Example 17

8-(2-Trifluoromethoxy-phenylamino)-1-(2-hydroxy-ethyl)-4,5-dihydro-1H-pyrazolo[4,3-h]quinazoline-3-carboxamide (A45B5C₁Z)

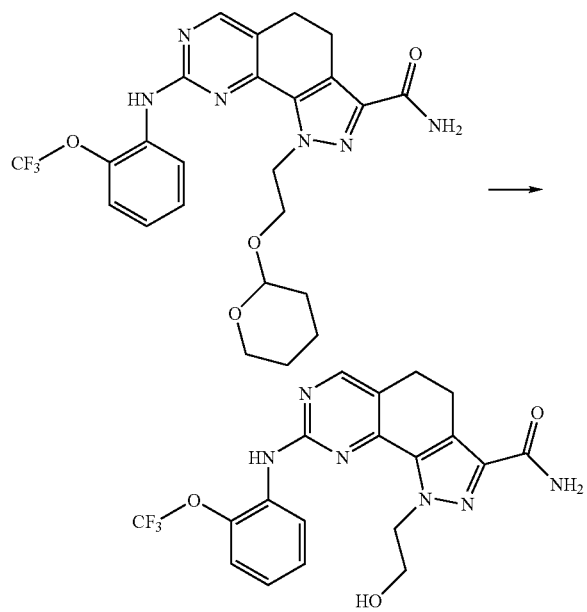

0.085 g (0.15 mmol) of 8-(2-trifluoromethoxy-phenylamino)-1-[2-(tetrahydro-pyran-2-yloxy)-ethyl]-4,5-dihydro-1H-pyrazolo[4,3-h]quinazoline-3-carboxamide were dissolved in 10 mL of ethanol and 28 mg of p-toluensulfonic acid (0.15 mmol) were added. The solution was stirred at room temperature overnight and the solvent removed in vacuo. The residue was purified by flash chromatography on silica gel (eluant: ethyl acetate/hexane 80/20) to afford 59 mg (90% yield) of the title compound.

$^1$H NMR (400 MHz, DMSO-$d_6$) δ ppm 2.80 (m, 2 H) 2.98 (m, 2 H) 3.67 (m, 2 H) 4.66 (m, 2 H) 7.22 (m, 1 H) 7.24 (bs, 1 H) 7.39 (m, 2 H) 7.43 (bs, 1 H) 7.87 (m, 1 H) 8.36 (s, 1 H) 9.0 (s, 1 H).

By working according to the above method the following compound was prepared:

1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B5C1Z)

$^1$H NMR (400 MHz, DMSO-$d_6$) δ ppm 2.24 (s, 3 H) 2.46 (br. s., 4 H) 2.80 (t, J=7.62 Hz, 2 H) 2.98 (t, J=7.62 Hz, 2 H) 3.15 (br. s., 4 H) 3.64 (q, J=5.49 Hz, 2 H) 4.59 (t, J=5.79 Hz, 1 H) 4.63 (t, J=5.37 Hz, 2 H) 6.79 (dd, J=8.96, 2.99 Hz, 1 H) 7.19-7.24 (m, 1 H) 7.24 (br. s., 1 H) 7.25 (d, J=2.93 Hz, 1 H) 7.43 (s, 1 H) 8.34 (s, 1 H) 8.85 (s, 1H).

Example 18

8-[5-(4-Ethyl-piperazin-1-yl)-2-trifluoromethoxy-phenylamino]-1-methyl-4,5-dihydro-1H-pyrazolo[4,3-h]quinazoline-3-carboxamide (A94B1C1Z)

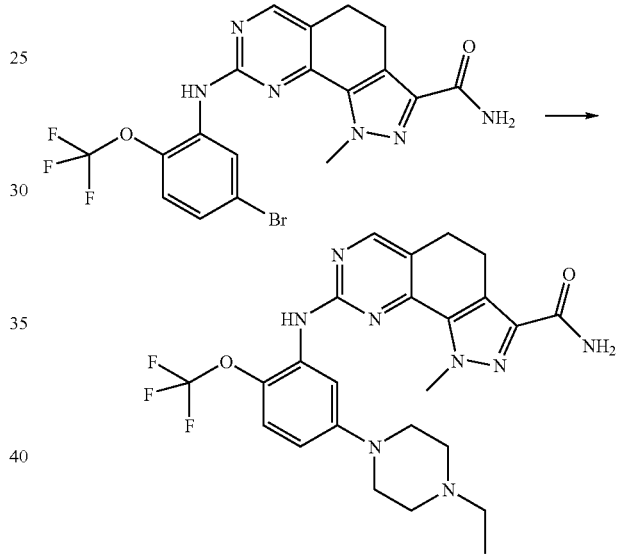

Tris(dibenzilideneacetone)dipalladium, Pd₂(dba)₃, (9.1 mg, 0.01 mmol), 2-dicyclohexylphosphino-2'-(N,N-dimethylamino)-biphenyl (7.8 mg, 0.02 mmol), 8-[2-trifluoromethoxy-5-bromo-phenylamino]-1-methyl-4,5-dihydro-1H-pyrazolo[4,3-h]quinazoline-3-carboxamide (200 mg, 0.41 mmol) in THF (4.5 mL) were charged in a round-bottom flask flushed with argon. The flask was evacuated and back-filled with argon. LiN(TMS)₂ solution (1M in THF, 2.7 mL) and N-ethylpiperazine (0.125 mL, 0.98 mmol) were added and the reaction mixture refluxed for 3 h. The reaction mixture was then allowed to cool to room temperature and concentrated. The crude solid was purified by flash chromatography on silica gel (eluant: DCM/EtOH 90/10) to afford 46 mg (52% yield) of the title compound.

$^1$H NMR (400 MHz, DMSO-$d_6$) δ ppm 1.02-1.07 (m, 3 H) 2.32-2.64 (m, 6 H) 2.77-2.83 (m, 2 H) 2.97 (t, J=7.80 Hz, 2 H) 3.14 (bs, 4 H) 4.16 (s, 3 H) 6.76 (dd, J=9.08, 2.99 Hz, 1 H) 7.17-7.22 (m, 1 H) 7.24 (bs, 1 H) 7.31 (d, J=2.93 Hz, 1 H) 7.43 (br.s, 1 H) 8.35 (s, 1 H) 8.88 (s, 1 H).

By working according to the same procedure the following compounds were prepared:

TABLE XV

| Code | NMR data |
|---|---|
| A95B1C1Z | $^1$H NMR (400 MHz, DMSO-$d_6$) δ ppm 1.87 (d, J = 12.68 Hz, 2 H) 2.02 (t, J = 10.79 Hz, 2 H) 2.17 (s, 3 H) 2.73 (d, J = 10.97 Hz, 2 H) 2.80 (t, J = 7.68 Hz, 2 H) 2.97 (t, J = 7.62 Hz, 2 H) 4.18 (s, 3 H) 5.66 (d, J = 8.05 Hz, 1 H) 6.36 (dd, J = 8.90, 2.80 Hz, 1 H) 7.00 (d, J = 2.68 Hz, 1 H) 7.04 (dd, J = 8.90, 1.22 Hz, 1 H) 7.23 (bs, 1 H) 7.44 (s, 1 H) 8.33 (s, 1 H) 8.71 (s, 1 H) |
| A96B1C1Z | $^1$H NMR (400 MHz, DMSO-$d_6$) δ ppm 1.42 (s, 9 H) 2.80 (t, J = 7.74 Hz, 2 H) 2.97 (t, J = 7.68 Hz, 2 H) 3.07-3.14 (m, 2 H) 3.41-3.47 (m, 2 H) 4.16 (s, 3 H) 6.77 (dd, J = 9.08, 2.99 Hz, 1 H) 7.22 (dq, J = 9.02, 1.34 Hz, 1 H) 7.24 (bs, 1 H) 7.33 (none, 1 H) 7.42 (bs, 1 H) 8.35 (s, 1 H) 8.35 (none, 1 H) 8.90 (s, 1 H) |
| A99B1C1Z | $^1$H NMR (400 MHz, DMSO-$d_6$) δ ppm 1.65 (m, 2 H) 1.90 (bs, 4 H) 2.08 (m, 2 H) 2.74 (m, 2 H) 2.80 (m, 2 H) 2.98 (m, 2 H) 3.05-3.34 (m, 5 H) 3.78 (d, J = 13.90 Hz, 2 H) 4.18 (s, 3 H) 6.80 (dd, J = 9.21, 2.99 Hz, 1 H) 7.22 (dd, J = 9.02, 1.34 Hz, 1 H) 7.27 (s, 1 H) 7.36 (d, J = 2.93 Hz, 1 H) 7.40 (s, 1 H) 8.36 (s, 1 H) 8.91 (s, 1 H) |
| A100B1C1Z | $^1$H NMR (400 MHz, DMSO-$d_6$) δ ppm 1.67 (t, J = 6.89 Hz, 2 H) 2.12 (s, 3 H) 2.29 (m, 4 H) 2.33 (m, 2 H) 2.80 (t, J = 7.62 Hz, 2 H) 2.97 (t, J = 7.80 Hz, 2 H) 3.02 (d, J = 5.73 Hz, 2 H) 4.19 (s, 3 H) 5.86 (t, J = 5.61 Hz, 1 H) 6.34 (dd, J = 8.90, 2.80 Hz, 1 H) 6.98 (d, J = 2.80 Hz, 1 H) 7.06 (dd, J = 8.84, 1.28 Hz, 1 H) 7.24 (s, 1 H) 7.43 (s, 1 H) 8.35 (s, 1 H) 8.71 (s, 1 H) |
| A101B1C1Z | $^1$H NMR (400 MHz, DMSO-$d_6$) δ ppm 1.67 (m, 2 H) 2.37 (m, 8 H) 2.59 (bs, 2 H) 2.81 (t, J = 7.74 Hz, 2 H) 2.98 (t, J = 7.50 Hz, 2 H) 3.15 (m, 4 H) 4.17 (s, 3 H) 6.76 (dd, J = 9.15, 2.93 Hz, 1 H) 7.21 (dd, J = 9.08, 1.28 Hz, 1 H) 7.25 (bs, 1 H) 7.32 (d, J = 2.80 Hz, 1 H) 7.43 (s, 1 H) 8.36 (s, 1 H) 8.89 (s, 1 H) |
| A107B1C1Z | $^1$H NMR (400 MHz, DMSO-$d_6$) δ ppm 1.60 (m, 4 H) 1.93 (m, 4 H) 2.37 (m, 6 H) 2.80 (m, 2 H) 2.95 (m, 2 H) 3.04 (m, 2 H) 3.76 (bs, 1 H) 4.17 (s, 3 H) 6.35 (d, J = 8.41 Hz, 1 H) 6.98 (d, J = 2.80 Hz, 1 H) 7.15 (dd, J = 9.15, 1.10 Hz, 1 H) 7.24 (bs, 1 H) 7.43 (bs, 1 H) 8.33 (s, 1 H) 8.81 (s, 1 H) |
| A108B1C1Z | $^1$H NMR (400 MHz, DMSO-$d_6$) δ ppm 0.90 (t, J = 7.07 Hz, 6 H) 2.45 (m, 4 H) 2.79 (m, 2 H) 2.91 (s, 3 H) 2.96 (m, 2 H) 3.37 (m, 2 H) 4.16 (s, 3 H) 6.48 (dd, J = 9.15, 3.05 Hz, 1 H) 7.02 (d, J = 3.05 Hz, 1 H) 7.14 (m, 1 H) 7.23 (br. s., 1 H) 7.43 (s, 1 H) 8.32 (s, 1 H) 8.79 (s, 1 H) |
| A109B1C1Z | $^1$H NMR (400 MHz, DMSO-$d_6$) δ ppm 1.47 (m, 2 H) 1.65 (m, 2 H) 1.92 (m, 2 H) 2.25 (m, 6 H) 2.81 (m, 2 H) 2.98 (m, 2 H) 3.02 (m, 2 H) 4.19 (s, 3 H) 5.81 (m, 1 H) 6.35 (dd, J = 8.90, 2.80 Hz, 1 H) 7.00 (d, J = 2.80 Hz, 1 H) 7.08 (dd, J = 8.84, 1.28 Hz, 1 H) 7.25 (bs, 1 H) 7.44 (b s, 1 H) 8.35 (s, 1 H) 8.71 (s, 1 H) |
| A110B1C1Z | $^1$H NMR (400 MHz, DMSO-$d_6$) δ ppm 1.04 (s, 6 H) 1.08 (s, 6 H) 1.22 (m, 3 H) 1.81 (d, J = 11.34 Hz, 1 H) 2.19 (s, 3 H) 2.81 (t, J = 7.74 Hz, 2 H) 2.98 (t, J = 7.56 Hz, 2 H) 3.47 (m, 1 H) 4.19 (s, 3 H) 5.59 (d, J = 7.44 Hz, 1 H) 6.37 (dd, J = 8.90, 2.44 Hz, 1 H) 7.04-7.09 (m, 2 H) 7.25 (bs, 1 H) 7.44 (bs, 1 H) 8.34 (s, 1 H) 8.72 (s, 1 H) |
| A111B1C1Z | $^1$H NMR (400 MHz, DMSO-$d_6$) δ ppm 2.03 (m, 2 H) 2.79 (m, 2 H) 2.96 (m, 2 H) 3.41 (m, 2 H) 3.60 (m, 2 H) 4.17 (s, 3 H) 6.55 (dd, J = 9.15, 2.93 Hz, 1 H) 7.03 (d, J = 2.56 Hz, 1 H) 7.16 (d, J = 8.05 Hz, 1 H) 7.24 (bs, 1 H) 7.41 (s, 1 H) 8.32 (s, 1 H) 8.84 (s, 1 H) |
| A112B1C1Z | $^1$H NMR (400 MHz, DMSO-$d_6$) δ ppm 1.65 (m, 1 H) 2.05 (m, 1 H) 2.79 (m, 2 H) 2.98 (m, 2 H) 3.86 (m, 1 H) 4.19 (s, 3 H) 5.95 (d, J = 6.22 Hz, 1 H) 6.37 (dd, J = 8.90, 2.80 Hz, 1 H) 7.03 (d, J = 2.80 Hz, 1 H) 7.11 (m, 1 H) 7.26 (bs, 1 H) 7.44 (bs, 1 H) 8.35 (s, 1 H) 8.77 (s, 1 H) |
| A51B11C1Z | $^1$H NMR (400 MHz, DMSO-$d_6$) δ ppm 2.23 (s, 3 H) 2.42-2.47 (m, 4 H) 2.78 (t, J = 7.80 Hz, 2 H) 2.97 (t, J = 7.68 Hz, 2 H) 3.10-3.16 (m, 4 H) 3.67 (s, 3 H) 5.73 (s, 2 H) 6.69 (d, J = 8.54 Hz, 2 H) 6.76 (dd, J = 9.15, 2.93 Hz, 1 H) 6.98 (d, J = 8.54 Hz, 2 H) 7.20 (dd, J = 9.08, 1.28 Hz, 1 H) 7.25 (d, J = 2.93 Hz, 1 H) 7.28 (s, 1 H) 7.47 (s, 1 H) 8.33 (s, 1 H) 9.01 (s, 1 H) |

Example 19

8-(5-piperazin-1-yl-2-trifluoromethoxy-phenylamino)-1-methyl-4,5-dihydro-1H-pyrazolo[4,3-h]quinazoline-3-carboxamide (A97B1C1Z)

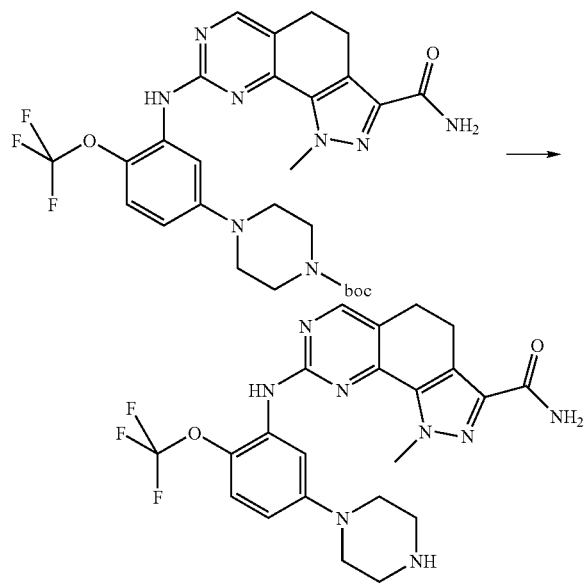

To a solution of 8-[5-(4-t-butoxycarbonyl-piperazin-1-yl)-2-trifluoromethoxy-phenylamino]-1-methyl-4,5-dihydro-1H-pyrazolo[4,3-h]quinazoline-3-carboxamide (94 mg, 0.16 mmol) in dioxane (3 ml), 4M HCl in dioxane (0.89 ml, 3.42 mmol) was added. The mixture was stirred at room temperature for 3 h. The solvent was removed under reduced pressure and the crude was diluted with Et$_2$O and decanted, to give the final compound as a hydrochloride salt in quantitative yield.

$^1$H NMR (400 MHz, DMSO-d$_6$) δ ppm 2.80 (t, J=7.68 Hz, 2 H) 2.97 (t, J=7.44 Hz, 2 H) 3.19-3.43 (m, 8 H) 4.17 (s, 3 H) 6.83 (dd, J=9.02, 3.05 Hz, 1 H) 7.25-7.29 (m, 2 H) 7.38 (d, J=3.05 Hz, 1 H) 7.39 (bs, 1 H) 8.35 (s, 1 H) 8.97 (bs, 2 H) 9.02 (s, 1 H).

Example 20

8-(2-Trifluoromethoxy-5-(4-methyl-4-oxy-piperazin-1-yl)-phenylamino)-1-methyl-4,5-dihydro-1H-pyrazolo[4,3-h]quinazoline-3-carboxamide (A102B1C1Z)

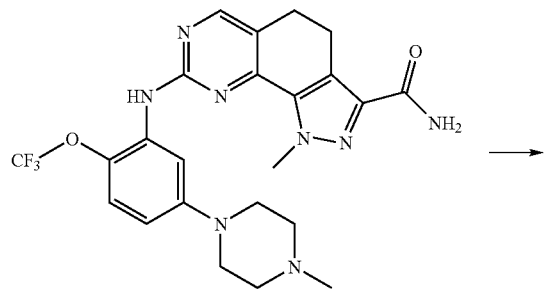

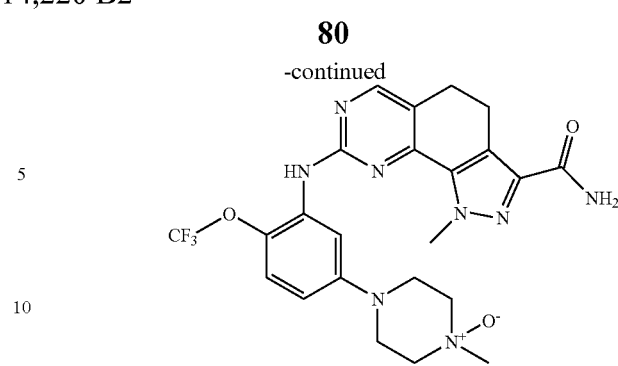

To a solution of 8-(2-trifluoromethoxy-5-(4-methyl-piperazin-1-yl)-phenylamino)-1-methyl-4,5-dihydro-1H-pyrazolo[4,3-h]quinazoline-3-carboxamide (50 mg, 0.1 mmol) in a mixture (1:1) DCM/Acetone (10 ml), 0.1M 3,3-dimethyldioxirane (2 ml, 0.2 mmol) was added. The mixture was stirred at room temperature for 1 h. The solvent was removed under reduced pressure and the crude was purified by flash chromatography (DCM/MeOH/7N NH$_3$ in methanol 9:1:0.2), to give the final compound (16 mg, 30%) as a white solid.

$^1$H NMR (400 MHz, DMSO-d$_6$) δ ppm 2.81 (t, J=7.68 Hz, 2 H) 2.98 (t, J=7.68 Hz, 2 H) 3.03 (d, J=7.68 Hz, 2 H) 3.14 (s, 3 H) 3.44-3.53 (m, 6 H) 4.18 (s, 3 H) 6.83 (dd, J=9.08, 2.99 Hz, 1 H) 7.23 (d, J=1.34 Hz, 1 H) 7.25 (bs, 1 H) 7.39 (d, J=3.05 Hz, 1 H) 7.43 (s, 1H) 8.37 (s, 1H) 8.94 (s, 1H).

Example 21

8-(2-Trifluoromethoxy-5-(4-methyl-1,4-dioxy-piperazin-1-yl)-phenylamino)-1-methyl-4,5-dihydro-1H-pyrazolo[4,3-h]quinazoline-3-carboxamide (A103B1C1Z)

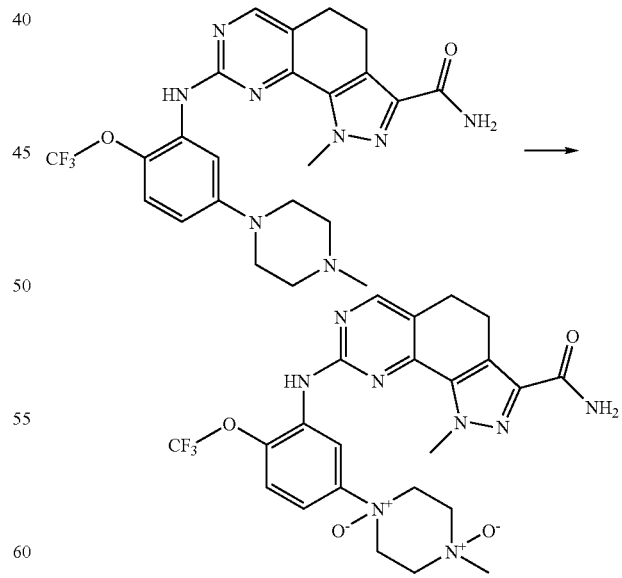

To a solution of 8-(2-trifluoromethoxy-5-(4-methyl-piperazin-1-yl)-phenylamino)-1-methyl-4,5-dihydro-1H-pyrazolo[4,3-h]quinazoline-3-carboxamide (50 mg, 0.1 mmol) in a mixture (1:1) DCM/Acetone (10 ml), 0.1 M 3,3-dimethyldioxirane (5 ml, 0.5 mmol) was added. The mixture was stirred at room temperature for 1 h. The solvent was removed under reduced pressure and the crude was purified by flash chromatography (DCM/MeOH/7N NH$_3$ in methanol 9:1:0.2), to give the final compound (21 mg, 40%) as a white solid.

$^1$H NMR (400 MHz, DMSO-d$_6$) δ ppm 4.24 (s, 3 H) 7.54 (dd, J=2.07, 1.46 Hz, 1 H) 7.84 (dd, J=3.78, 3.41 Hz, 1 H) 8.44 (s, 1 H) 8.94 (d, J=2.56 Hz, 1 H) 9.29 (s, 1H).

By working according to the same procedure the following compound was prepared:

1-(2-Hydroxy-ethyl)-8-(2-trifluoromethoxy-5-(4-methyl-1,4-dioxy-piperazin-1-yl)-phenylamino)-4,5-dihydro-1H-pyrazolo[4,3-h]quinazoline-3-carboxamide (A103B5C1Z).

$^1$H NMR (400 MHz, DMSO-d$_6$) δ ppm 2.82 (t, J=7.62 Hz, 2 H) 2.97 (t, J=7.56 Hz, 2 H) 3.08 (t, J=9.57 Hz, 4 H) 3.23 (s, 3 H) 3.68 (q, J=6.38 Hz, 2 H) 4.25 (td, J=11.67, 2.01 Hz, 2 H) 4.52-4.76 (m, 4 H) 6.53 (t, J=5.30 Hz, 1 H) 7.25 (br. s., 1 H) 7.42 (br. s., 1 H) 7.56 (dq, J=9.08, 1.40 Hz, 1 H) 7.78 (dd, J=9.14, 2.80 Hz, 1 H) 8.44 (s, 1 H) 8.77 (d, J=2.80 Hz, 1H) 9.26 (s, 1H).

Example 22

8-(5-amino-2-trifluoromethoxy-phenylamino)-1-methyl-4,5-dihydro-1H-pyrazolo[4,3-h]quinazoline-3-carboxamide (A46B1C1Z)

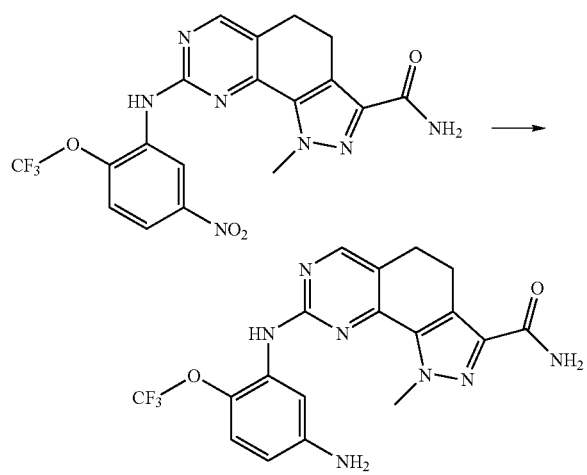

To a suspension of 8-(5-nitro-2-trifluoromethoxy-phenylamino)-1-methyl-4,5-dihydro-1H-pyrazolo[4,3-h]quinazoline-3-carboxamide (630 mg, 1.4 mmol) in methanol (6 mL) ammonium chloride (240 mg, 4.3 mmol) in water (25 mL) and iron (397 mg, 7.4 mmol) were added. The mixture was heated under reflux for 3 hours until HPLC revealed the disappearance of the starting material. The solvent was removed and the crude was diluted with trifluoroethanol. Iron was removed and the filtrate was concentrated to give the final compound as a light brown solid in quantitative yield.

$^1$H NMR (400 MHz, DMSO-d$_6$) δ ppm 2.80 (t, J 7.74 Hz, 2 H) 2.97 (t, J=7.56 Hz, 2 H) 4.20 (s, 3 H) 5.31 (bs, 2 H) 6.34 (dd, J=8.78 and 2.68 Hz, 1 H) 7.00 (dq, J=8.79, 1.37 and 1.33 Hz, 1 H) 7.07 (d, J=2.70 Hz, 1 H) 7.23 (bs, 1 H) 7.44 (bs, 1 H) 8.35 (s, 1 H) 8.65 (s, 1 H).

Example 23

8-{5-[(pyrrolidine-2-carbonyl)-amino]-2-trifluoromethoxy-phenylamino}-1-methyl-4,5-dihydro-1H-pyrazolo[4,3-h]quinazoline-3-carboxamide (A50B1C1Z)

To a suspension of 8-(5-amino-2-trifluoromethoxy-phenylamino)-1-methyl-4,5-dihydro-1H-pyrazolo[4,3-h]quinazoline-3-carboxamide (146 mg, 0.4 mmol) in anhydrous dimethylformamide (5 mL) TBTU (190 g, 0.6 mmol) HOBT (81 mg, 0.6 mmol), and DIPEA (0.104 ml, 0.6 mmol) were added. The mixture was stirred at room temperature for 30 minutes. Then BOC-L-proline (129 mg, 0.6 mmol) was added and the reaction was stirred for an additional 3 h. The reaction mixture was diluted with water and the precipitate was collected, diluted with DCM (10 mL) and treated with TFA (1 mL). Evaporation of the solvent gave the title compound as trifluoroacetate salt (113 mg, 44% yield).

| Code | M + H | RT | METHOD |
| --- | --- | --- | --- |
| A50B1C1Z | 517.19 | 3.7 | 2 |
| A82B1C1Z | 545.21 | 3.4 | 2 |

Example 24

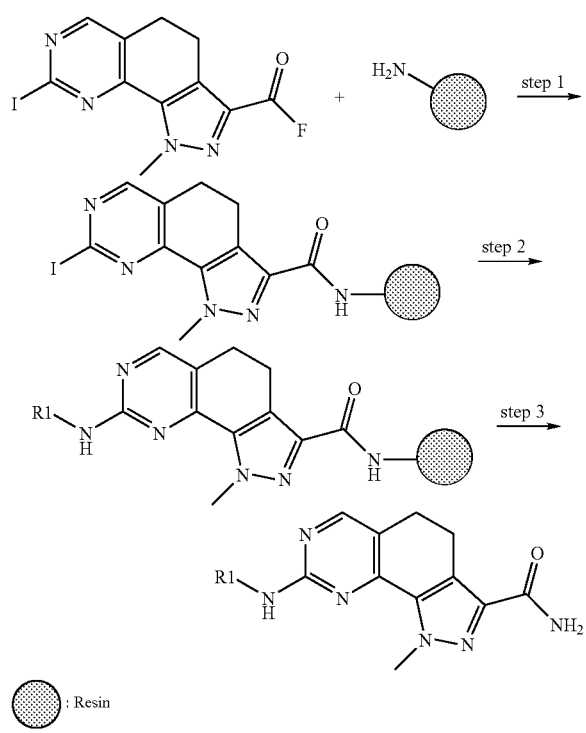

: Resin

Step 1. Acylation of the solid supported amine with 8-iodo-1-methyl-4,5-dihydro-1H-pyrazolo[4,3-h]quinazoline-3-carbonyl fluoride In this case, the "resin" is Rink amide, 4-(2',4'-dimethoxyphenyl-fmoc-aminomethyl)phenoxy (copolystyrene-1% DVB):

8.8 g (4.8 mmol) of the aforementioned resin were charged into a 100 mL Argonaut Quest 205 reaction tube. Removal of the Fmoc protecting group was accomplished by treating the resin with 60 mL of 20% piperidine in DMF for 5 minutes and followed by a second treatment for 30 minutes at room temperature. The resin was washed with DMF (3×50 mL, 5 min.), methanol (3×50 mL, 5 min.) and finally with dichloromethane (3×50 mL, 5 min).

To the 8.8 g (4.8 mmol) of previously deprotected resin, the following pre-activated carboxylic acid fluoride reagent was added. In 50 mL of 1,4-dioxane, 2.78 g (7.81 mmol, 1.6 equivalents) of 8-iodo-1-methyl-4,5-dihydro-1H-pyrazolo[4,3-h]quinazoline-3-carboxylate, 2.41 g (9.12 mmol, 1.9 equivalents) of tetramethylfluoroformamidinium hexafluorophosphate and 1.59 mL (9.12 mmol, 1.9 equivalents) of N,N-diisopropylethylamine were dissolved. N,N-dimethylacetamide was added dropwise to the solution until all reagents were in solution with sonication. The reaction system was stirred at room temperature for 30 minutes. An additional 1.59 mL (9.12 mmol, 1.9 equivalents) of N,N-diisopropylethylamine were added to the solution and the entire contents was charged to the resin on the Quest 210 synthesizer. The resin was mixed for 6 hours at 60° C. followed by an additional 12 hours at room temperature. The resin was drained of the acylation cocktail and washed with 1,4-dioxane (3×50 mL, 5 min.) whereby the acylation procedure was repeated a second time using the previously described protocol. Upon completion of the second acylation cycle, the resin was again drained of the acylation cocktail and washed with 1,4-dioxane (3×50 mL, 5 min.), DMF (3×50 mL, 5 min.), and finally with DCM (3×50 mL, 5 min.). The resin was dried from DCM under vacuum. The resin was qualitatively tested for the acylation reaction completion using the ninhydrin test method.

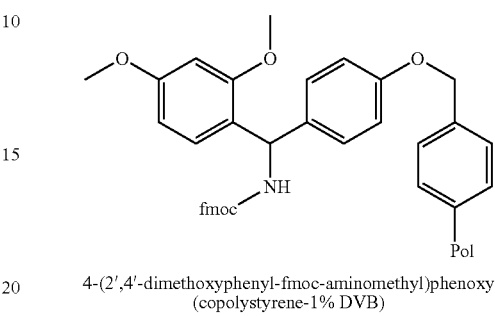

4-(2',4'-dimethoxyphenyl-fmoc-aminomethyl)phenoxy (copolystyrene-1% DVB)

Step 2. Catalytic amination of the solid supported 8-iodo-1-methyl-4,5-dihydro-1H-pyrazolo[4,3-h]quinazoline-3-carboxamide Using a 4 mL Argonaut Trident synthesizer cassette, 200 mg (0.11 mmol) of the resin from step 1 above, were charged into separate vials. To each of the reactor vials flushed with argon, finely divided potassium carbonate (0.15 g, 1.1 mmol), palladium acetate [$Pd(OAc)_2$] (2.5 mg, 0.011 mmol, 10%), (±)-BINAP (6.8 mg, 0.011 mmol, 10%) and the corresponding amine (0.22 mmol, 2 equivalents) in degassed (argon) dimethyacetamide (2 mL) were added. The resulting mixture was agitated at 60° C. for 10 hours on the Argonaut Trident Automated Library Synthesizer (ALS) station. The Trident ALS station was programmed to continuously mechanically agitate the resin at 60° C. while a nitrogen gas "sparge" was incorporated to re-suspend the scarcely soluble potassium carbonate. Nitrogen gas sparging was incorporated once per hour, for a 30 second duration, throughout the 16-hour heating cycle.

The resin was drained from the synthesis cocktail and washed using the Argonaut Trident External Agitation Thermal Unit (EATU) synthesis station with DMA (3×2 mL, 5 min.). The above catalytic amination cycle was repeated a second time using the previously described procedure.

Upon completion of the second amination cycle, the resin was drained from the synthesis cocktail and washed using the Argonaut Trident EATU synthesis station with DMF (1×2 mL, 5 min.), with water (1×2 mL, 5 min.), with DMF/water (1:1) (3×2 mL, 5 min.), with DMF (3×2 mL, 5 min.), with methanol (3×2 mL, 5 min.) and with DCM (3×2 mL, 5 min.).

Step 3. Cleavage of the differentially substituted 8-amino-1-methyl-4,5-dihydro-1H-pyrazolo[4,3-h]quinazoline-3-carboxamide from the solid support To each Argonaut Trident reactor vial, 2 mL of the following resin cleavage cocktail were added: dichloromethane (100 mL), trifluoroacetic acid (98 mL) and water (2 mL). The resin, suspended in the cleavage cocktail, was shaken for 2 hours at room temperature on the Argonaut Trident EATU synthesis station. The solution containing the crude products was captured into separate vials. The resin was treated to a second cycle of the aforementioned cleavage cocktail and three additional resin washes with dichloromethane (2 mL each) were also captured to the same corresponding vials.

By working analogously, the following compounds were prepared:

TABLE XVI

| Code | M + H | RT | method |
|---|---|---|---|
| A52B1C1Z | 403.3 | 1.444 | 1 |
| A53B1C1Z | 390.2 | 0.951 | 1 |
| A66B1C1Z | 464.3 | 0.943 | 1 |
| A65B1C1Z | 447.3 | 1.141 | 1 |
| A54B1C1Z | 387.2 | 0.739 | 1 |
| A55B1C1Z | 377.2 | 1.477 | 1 |
| A56B1C1Z | 427.3 | 1.6 | 1 |
| A57B1C1Z | 463.7 | 1.845 | 1 |
| A58B1C1Z | 446.7 | 1.592 | 1 |
| A59B1C1Z | 461.3 | 1.361 | 1 |
| A60B1C1Z | 361.3 | 1.443 | 1 |
| A61B1C1Z | 437.1 | 1.47 | 1 |
| A62B1C1Z | 455.3 | 1.413 | 1 |
| A63B1C1Z | 431.7 | 1.617 | 1 |
| A64B1C1Z | 400.3 | 1.525 | 1 |
| A67B1C1Z | 415.3 | 1.508 | 1 |
| A79B1C1Z | 404.3 | 1.369 | 1 |
| A68B1C1Z | 387.2 | 1.273 | 1 |
| A69B1C1Z | 439.3 | 1.311 | 1 |
| A70B1C1Z | 411.3 | 1.634 | 1 |
| A71B1C1Z | 431.7 | 1.615 | 1 |
| A72B1C1Z | 384.1 | 1.279 | 1 |
| A73B1C1Z | 380.2 | 1.282 | 1 |
| A74B1C1Z | 393.2 | 1.255 | 1 |
| A75B1C1Z | 393.2 | 1.228 | 1 |
| A76B1C1Z | 363.2 | 0.919 | 1 |
| A77B1C1Z | 378.2 | 0.832 | 1 |
| A78B1C1Z | 421.2 | 1.577 | 1 |

Example 25

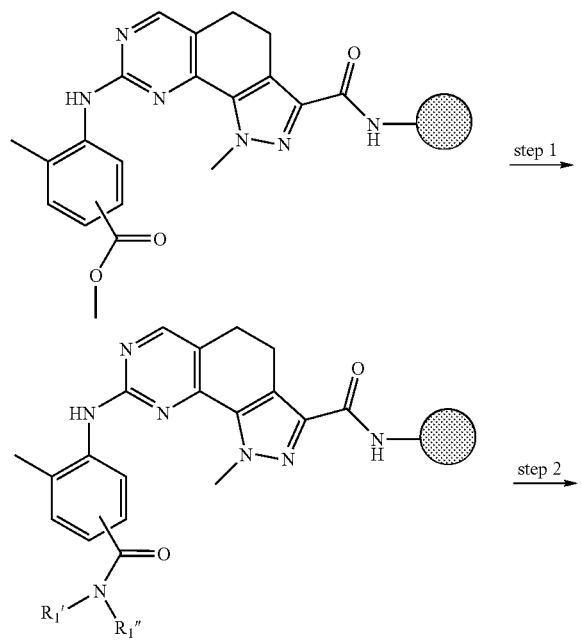

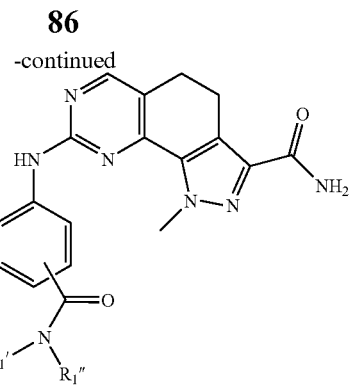

Step 1. Direct acylation of the solid supported methyl esters of methyl 4-[(3-carbamoyl-1-methyl-4,5-dihydro-1H-pyrazolo[4,3-h]quinazoline-8-yl)amino]-3-methylbenzoate A modified protocol of Weinreb amide acylation chemistry (Tetrahedron Lett. 1977, 48, 4171) was applied in the generation of the desired carboxamides directly from methyl ester compounds tethered to a solid support. To a Biotage/Personal Chemistry, Smith Creator 0.5-2 mL microwave reactor vial was charged 200 mg (1.1 mmol) of dry resin prepared in step 2 (catalytic amination) above. The vial was purged with argon gas and placed aside. To an argon gas purged, 1-dram vial containing 2 mL of dry DCM was charged 0.045 g (0.44 mmol, 4 equivalents) of the appropriate amine followed by 225 microL of a trimethylaluminum solution (2M in toluene). The vial was agitated on a vortex mixer for 30 seconds and allowed to stand at room temperature for 15 minutes, after which time the entire contents was charged to the microwave reactor vial containing the dry resin. The microwave vial was placed in the Smith Creator microwave system that was programmed to irradiate the vial for 10 minutes at 110° C. with simultaneous cooling. Upon completion of the heating and cool down cycle, the reaction was quenched with methanol/water (1:1) and washed with DMF (3×2 mL, 5 min.), with methanol (3×2 mL, 5 min.) and with DCM (3×2 mL, 5 min.).

Step 2. Cleavage of the differentially substituted 8-[(5-carbamoyl-2-methylphenyl)amino]-1-methyl-4,5-dihydro-1H-pyrazolo[4,3-h]quinazoline-3-carboxamide compounds from the solid support To each reactor vials, 2 mL of the following resin cleavage cocktail were added: dichloromethane (100 mL), trifluoroacetic acid (98 mL) and water (2 mL). The resin suspended in the cleavage cocktail was shaken for 2 hours at room. The solution containing the crude products was captured into separate vials. The resin was treated to a second cycle of the aforementioned cleavage cocktail and three additional resin washes with dichloromethane (2 mL each) were also captured to the same corresponding vials.

TABLE XVII

| Code | M + H | RT | method |
|---|---|---|---|
| A86B1C1Z | 378.2 | 0.832 | 1 |
| A87B1C1Z | 378.1 | 0.705 | 1 |
| A83B1C1Z | 394.1 | 0.764 | 1 |
| A93B1C1Z | 394.4 | 0.792 | 1 |

Example 26

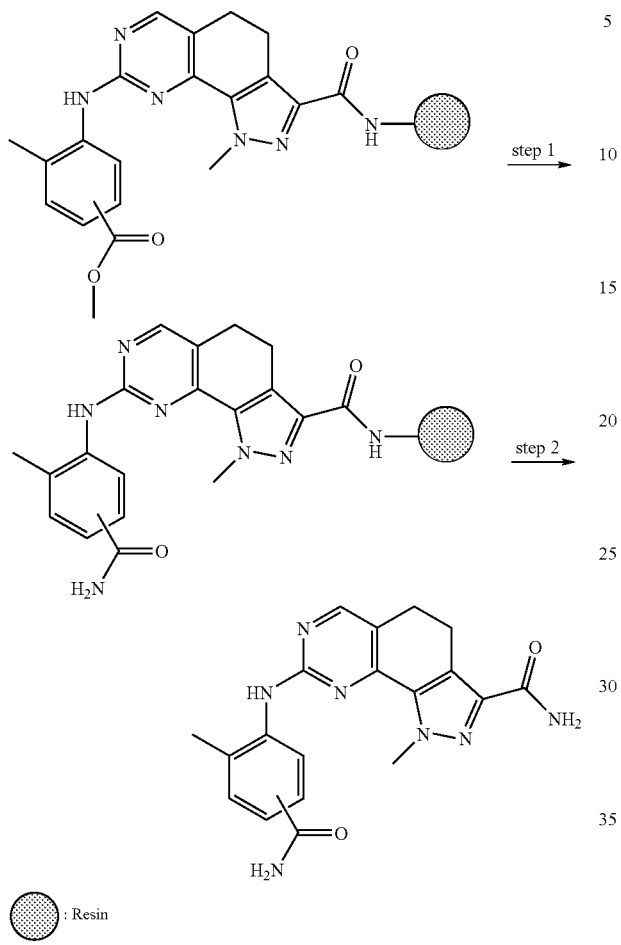

○ : Resin

Step 1. Direct acylation of the solid supported methyl esters of methyl 4-[(3-carbamoyl-1-methyl-4,5-dihydro-1H-pyrazolo[4,3-h]quinazoline-8-yl) amino]-3-methylbenzoate To a 4 mL Argonaut Trident synthesizer cassette, was placed 200 mg (0.11 mmol) of the dry resin prepared in step 2 (catalytic amination) above. The vials were purged with argon gas and 1 mL of dry THF was added to pre-swell the resin. To the suspended resin was charged 1.1 mL (1.1 mmol, 10 equivalents) of lithium bis(trimethylsilyl)amide (1.0 M in THF) followed by 0.058 g of a ammonium chloride (1.1 mol, 10 equivalents). The cassette was agitated for 60 minutes at room temperature after which time the contents of the cassette was drained and washed with DMF (3×2 mL, 5 min.), with methanol (3×2 mL, 5 min.) and with DCM (3×2 mL, 5 min.).

Step 2. Cleavage of the differentially substituted 8-[(5-carbamoyl-2-methylphenyl)amino]-1-methyl-4,5-dihydro-1H-pyrazolo[4,3-h]quinazoline-3-carboxamide compounds from the solid support To each Argonaut Trident reactor vial, 2 mL of the following resin cleavage cocktail were added: dichloromethane (100 mL), trifluoroacetic acid (98 mL) and water (2 mL). The resin suspended in the cleavage cocktail was shaken for 2 hours at room temperature on the Argonaut Trident EATU synthesis station. The solution containing the crude products was captured into separate vials. The resin was treated to a second cycle of the aforementioned cleavage cocktail and three additional resin washes with dichloromethane (2 mL each) were also captured to the same corresponding vials.

TABLE XVIII

| Code | M + H | RT | Method |
|---|---|---|---|
| A77B1C1Z | 378.2 | 0.832 | 1 |
| A88B1C1Z | 378.1 | 0.705 | 1 |

Example 27

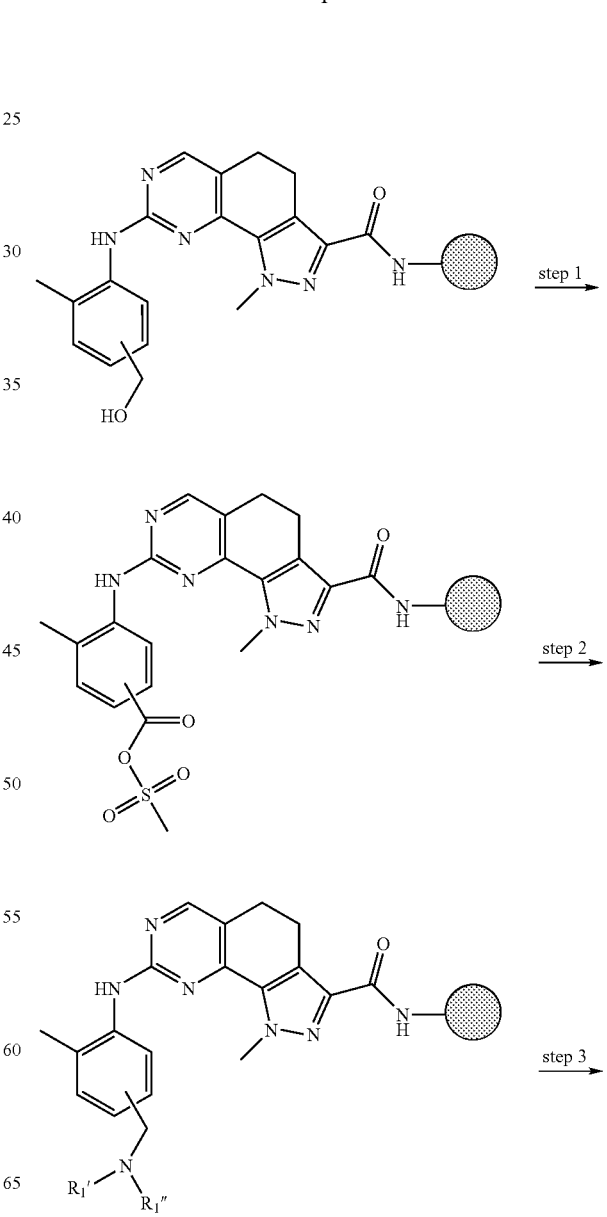

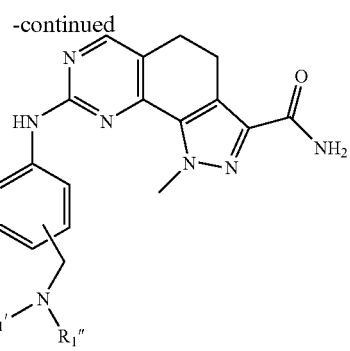

Step 1. Mesylation of solid supported 8-{[5-(hydroxymethyl)-2-methylphenyl]amino}-1-methyl-4,5-dihydro-1H-pyrazolo[4,3-h]quinazoline-3-carboxamide In the case where a hydroxymethyl group was to be converted to an aminomethyl group bearing a variety of substituents, the 4 mL Argonaut Trident synthesizer cassette, containing 200 mg (0.11 mmol) of the resin from step 2 (catalytic amination) above, was utilized. To each of the reactor vials was added methanesulfonyl chloride (0.085 mL, 1.1 mmol, 10 equivalents), and triethylamine (0.11 mL, 1.1 mmol, 10 equivalents) in dichloromethane (2 mL). The resulting mixture was agitated at ambient temperature for 2 hours on the Argonaut Trident Automated Library Synthesizer (ALS) station. Upon completion of the reaction cycle, the resin was drained of the synthesis cocktail and washed using the Argonaut Trident EATU synthesis station DMF (3×2 mL, 5 min.), with methanol (3×2 mL, 5 min.), with DCM (3×2 mL, 5 min.) and with THF (3×2 mL, 5 min.).

Step 2. Nucleophilic displacement of solid supported mesylates of 8-{[5-(hydroxymethyl)-2-methylphenyl]amino}-1-methyl-4,5-dihydro-1H-pyrazolo[4,3-h]quinazoline-3-carboxamide To the mesylate compounds prepared above in step 1, was added to the appropriate amine (0.11 mL, 1.1 mmol, 10 equivalents) in 2 mL of THF. The resulting mixture was agitated at 60° C. for 5 hours on the Argonaut Trident Automated Library Synthesizer (ALS) station. Upon completion of the reaction cycle, the resin was drained from the synthesis cocktail and washed using the Argonaut Trident EATU synthesis station DMF (3×2 mL, 5 min.), with methanol (3×2 mL, 5 min.), and with DCM (3×2 mL, 5 min.)

Step 3. Cleavage of the differentially substituted 8-{[5-(aminomethyl)-2-methylphenyl]amino}-1-methyl-4,5-dihydro-1H-pyrazolo[4,3-h]quinazoline-3-carboxamide compounds from the solid support To each Argonaut Trident reactor vial, 2 mL of the following resin cleavage cocktail were added: dichloromethane (100 mL), trifluoroacetic acid (98 mL) and water (2 mL). The resin suspended in the cleavage cocktail was shaken for 2 hours at room temperature on the Argonaut Trident EATU synthesis station. The solution containing the crude products was captured into separate vials. The resin was treated to a second cycle of the aforementioned cleavage cocktail and three additional resin washes with dichloromethane (2 mL each) were also captured to the same corresponding vials.

Defined below are the analytical HPLC/Mass data for some representative compounds:

TABLE XIX

| Code | M + H | RT | Method |
|---|---|---|---|
| A91B1C1Z | 447.5 | 3.26 | 2 |
| A92B1C1Z | 420.5 | 3.30 | 2 |

Example 28

4-Amino-N-(1-methyl-piperidin-4-yl)-3-trifluoromethoxy-benzamide

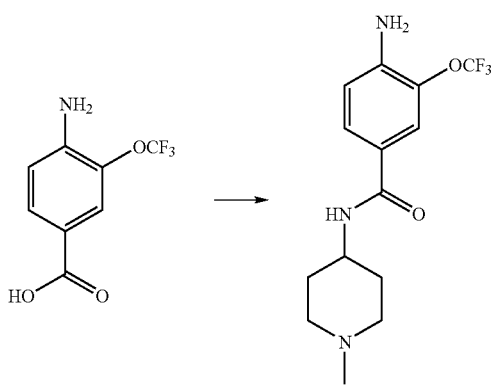 [SMILES: Nc1ccc(C(=O)O)cc1OC(F)(F)F ; CN1CCC(NC(=O)c2ccc(N)c(OC(F)(F)F)c2)CC1]

To a suspension of 4-amino-3-(trifluoromethoxy)benzoic acid (900 mg, 4 mmol) in dichloromethane (60 ml) TBTU (1.9 g, 6 mmol) and DIPEA (1.04 ml, 6 mmol) were added. The mixture was stirred at room temperature for 30 minutes. Then 1-methylpiperidin-4-amine (513 mg, 4.5 mmol) was added and the reaction was stirred for an additional 3 h. The solution was washed with water and the organic phase was dried over anhydrous $Na_2SO_4$. The crude was purified by flash chromatography (DCM/MeOH/$NH_3$aq, 9:1:0.5), to give the title compound (900 mg, 71%), as an orange solid.

$^1$H NMR (400 MHz, DMSO-$d_6$) δ ppm 1.55 (dq, J=3.90, 3.54 Hz, 2 H) 1.73 (d, J=14.51 Hz, 2 H) 1.92-2.03 (m, 2 H) 2.19 (bs, 3 H) 2.79 (d, J=10.73 Hz, 2 H) 3.69 (m, 1 H) 5.89 (bs, 1 H) 6.78 (d, J=8.54 Hz, 1 H) 7.61 (dd, J=1.95 Hz, 1 H) 7.64 (m, 1 H) 7.93 (d, J=7.56 Hz, 1H).

Example 29

5-(4-Methyl-piperazin-1-yl)-2-trifluoromethoxy-phenylamine trihydrochloride salt

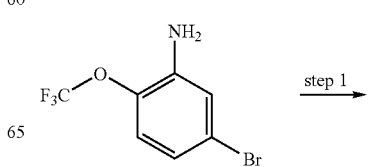

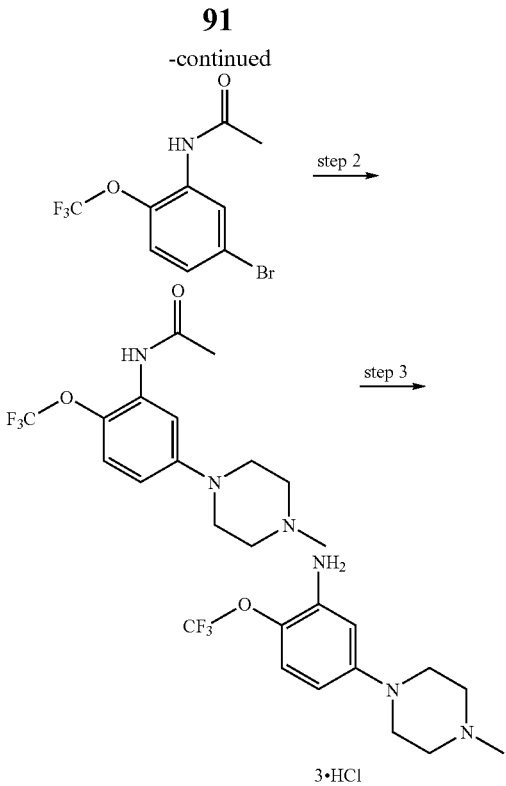

Step 1.
N-(5-bromo-2-trifluoromethoxy-phenyl)-acetamide

To a solution of 5-bromo-2-trifluoromethoxy-phenylamine (5.12 g, 20 mmol) in EtOH (50 mL) at 0° C. was added a solution of acetic anhydride (4.7 mL, 50 mmol) in EtOH (10 mL). The mixture was stirred at room temperature overnight. The solvent was evaporated to dryness and the solid was tritured with diethyl ether and filtered to give 5.64 g (95% yield) of N-(5-bromo-2-trifluoromethoxy-phenyl)-acetamide.

$^1$H NMR (400 MHz, DMSO-$d_6$) δ ppm: 2.11 (s, 3 H) 7.39 (m, 2 H) 8.21 (s, 1 H) 9.87 (s, 1 H).

By working according to the same procedure the following compounds were prepared:

N-(4-Bromo-2-trifluoromethoxy-phenyl)-acetamide $^1$H NMR (400 MHz, DMSO-$d_6$) δ ppm 2.09 (s, 3 H) 7.57 (dd, J=8.8 and 2.2 Hz, H) 7.63 (m, 1 H) 7.90 (d, J=8.8 Hz, 1 H) 9.80 (s, 1 H);

N-(4-Bromo-2-methoxy-phenyl)-acetamide $^1$H NMR (400 MHz, DMSO-$d_6$) δ ppm 2.07 (s, 3 H) 3.84 (s, 3 H) 7.07 (dd, J=8.5 and 2.2 Hz, 1 H) 7.20 (d, J=2.2 Hz, 1 H) 7.89 (d, J=8.5 Hz, 1 H) 9.17 (s, 1 H);

N-(2-Acetyl-4-bromo-phenyl)-acetamide $^1$H NMR (400 MHz, DMSO-$d_6$) δ ppm 2.10 (s, 3 H) 2.60 (s, 3 H) 7.75 (dd, J=8.9 and 2.4 Hz, 1 H) 8.04 (d, J=2.4 Hz, 1 H) 8.11 (d, J=8.9 Hz, 1 H) 10.94 (s, 1 H).

Step 2. N-[2-trifluoromethoxy-5-(4-methyl-piperazin-1-yl)-phenyl]-acetamide

Pd$_2$(dba)$_3$ (155 mg, 0.17 mmol), 2-dicyclohexylphosphino-2'-(N,N-dimethylamino)-biphenyl (133 mg, 0.34 mmol), N-(5-bromo-2-trifluoromethoxy-phenyl)-acetamide (5.05 g, 17 mmol)) were charged in a round-bottom flask flushed with argon. The flask was evacuated and backfilled with argon. LiN(TMS)$_2$ solution (1M in THF, 37.6 mL) and N-methylpiperazine (2.3 mL, 20.5 mmol) were added and the reaction mixture refluxed for 3 h. The reaction mixture was then allowed to cool to room temperature and concentrated. The crude solid was purified by flash chromatography on silica gel (eluant: DCM/EtOH 90/10) to afford 4.78 g (88% yield) of the N-[5-(4-methyl-piperazin-1-yl)-2-trifluoromethoxy-phenyl]-acetamide.

$^1$H NMR (400 MHz, DMSO-$d_6$) δ ppm 2.06 (s, 3 H) 2.22 (s, 3 H) 2.45 (m, 4 H) 3.11 (m, 4 H) 6.75 (dd, J=9.15 and 3.05 Hz, 1 H) 7.17 (dd, J=9.15 and 1.46 Hz, 1 H) 7.41 (bs, 1 H) 9.54 (s, 1 H).

By working according to the same procedure the following compounds were prepared:

N-[4-(4-methyl-piperazin-1-yl)-2-trifluoromethoxy-phenyl]-acetamide $^1$H NMR (400 MHz, DMSO-$d_6$) δ ppm 2.01 (s, 3 H) 2.31 (s, 3 H) 2.54 (m, 4 H) 3.18 (m, 4 H) 6.85 (bs, 1 H) 6.93 (dd, J=8.90 and 2.68 Hz, 1 H) 7.51 (d, J=8.90 Hz, 1 H) 9.43 (s, 1 H);

N-[2-methoxy-4-(4-methyl-piperazin-1-yl)-phenyl]-acetamide $^1$H NMR (400 MHz, DMSO-$d_6$) δ ppm 2.01 (s, 3 H) 2.26 (s, 3 H) 2.52 (m, 4 H) 3.12 (m, 4 H) 3.80 (s, 3 H) 6.42 (dd, J=8.66 and 2.56 Hz, 1 H) 6.58 (d, J=2.56 Hz, 1 H) 7.59 (d, J=8.66, 1 H) 8.89 (s, 1 H).

Step 3. 5-(4-Methyl-piperazin-1-yl)-2-trifluoromethoxy-phenylamine trihydrochloride salt A solution of N-[5-(4-methyl-piperazin-1-yl)-2-trifluoromethoxy-phenyl]-acetamide (4.75 g, 15 mmol) in EtOH (100 mL) was treated with HCl 37% (35 mL). After 1 h under reflux the mixture was concentrated and tritured with hexane to give in quantitative yield, 5.74 g of 5-(4-methyl-piperazin-1-yl)-2-trifluoromethoxy-phenylamine trihydrochloride salt.

$^1$H NMR (400 MHz, DMSO-$d_6$) δ ppm 2.82 (d, J=4.76 Hz 3 H) 3.1 (m, 4 H) 3.48 (m, 4 H) 6.24 (dd, J=8.90 and 2.93 Hz, 1 H) 6.40 (d, J=2.93 Hz, 1 H) 6.98 (dd, J=8.90 and 1.34 Hz, 1 H) 10.31 (bs, 1 H).

By working according to the same procedure the following compounds were prepared:

4-(4-Methyl-piperazin-1-yl)-2-trifluoromethoxy-phenylamine trihydrochloride salt $^1$H NMR (400 MHz, DMSO-$d_6$) δ ppm 2.83 (d, J=4.02 Hz, 3 H) 3.01 (m, 4 H) 3.47 (m, 4 H) 6.90 (m, 2 H) 7.01 (m, 1 H) 10.44 (bs, 1 H);

2-Methoxy-4-(4-methyl-piperazin-1-yl)-phenylamine dihydrochloride salt $^1$H NMR (400 MHz, DMSO-$d_6$) δ ppm 2.83 (bs, 3 H) 3.13 (m, 4 H) 3.47 (m, 4 H) 3.91 (s, 3 H) 6.62 (dd, J=8.78 and 2.56 Hz, 1 H) 6.80 (d, J=2.56 Hz, 1 H) 7.27 (d, J=8.78 Hz, 1 H) 9.77 (bs, 3 H) 10.72 (bs, 1H);

1-[2-Amino-5-(4-methyl-piperazin-1-yl)-phenyl]-ethanone hydrochloride salt

¹H NMR (400 MHz, DMSO-d₆) δ ppm 2.53 (s, 3 H) 2.82 (bs, 3 H) 2.98 (m, 4 H) 3.61 (m, 4 H) 6.84 (d, J=8.54 Hz, 1 H) 7.15 (dd, J=8.54 and 2.56 Hz, 1 H) 7.27 (d, J=2.56 Hz, 1 H) 10.40 (bs, 1 H).

Example 30

1-[2-Amino-4-(4-methyl-piperazin-1-yl)-phenyl]-ethanone

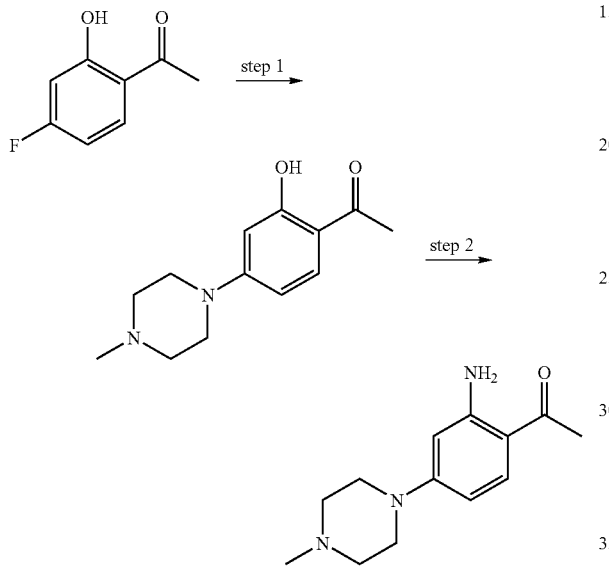

Step 1. 1-[2-Hydroxy-4-(4-methyl-piperazin-1-yl)-phenyl]ethanone 1-(4-Fluoro-2-hydroxy-phenyl)-ethanone (4.5 g, 29.22 mmol) was treated with N-methylpiperazine (5 mL) at 130° C. for 3 h to give 1-[2-hydroxy-4-(4-methyl-piperazin-1-yl)-phenyl]-ethanone in quantitative yield.

¹H NMR (400 MHz, DMSO-d₆) δ ppm 2.20 (s, 3 H) 2.39 (m, 4 H) 2.47 (s, 3 H) 3.35 (m, 4 H) 6.27 (d, J=2.6 Hz, 1 H) 6.52 (dd, J=9.15 and 2.6 Hz, 1 H) 7.66 (d, J=9.15 Hz, 1 H) 12.73 (s, 1 H).

By working according to the same procedure the following compound was prepared:

5-(4-Methyl-piperazin-1-yl)-2-nitro-benzonitrile

¹H NMR (400 MHz, DMSO-d₆) δ ppm 2.23 (s, 3 H) 2.43 (m, 4H) 3.55 (m, 4 H) 7.28 (d, J=9.63 and 2.93 Hz, 1 H) 7.56 (d, J=2.93 Hz, 1 H) 8.18 (d, J=9.63 Hz, 1 H).

Step 2. 1-[2-Amino-4-(4-methyl-piperazin-1-yl)-phenyl]-ethanone

To a solution of 1-[2-hydroxy-4-(4-methyl-piperazin-1-yl)-phenyl]-ethanone (5.22 g, 22.2 mmol) in DMA (50 mL) NaOH (2.67 g, 66.6 mmol) was added. The mixture was stirred at room temperature for 1 h, after which time 11.1 g (66.7 mmol) of 2-bromo-2-methylpropanamide was added and the mixture was stirred at room temperature overnight. 8.01 g (200 mmol) of NaOH was added and the resulting mixture was stirred at 100° C. for 2 h, then 50 mL of water was added and the mixture was stirred at 100° C. for 1 h. After cooling to room temperature, the mixture was concentrated and then diluted with DCM and washed with water, dried over sodium sulfate and concentrated. The crude solid was purified by flash chromatography on silica gel (eluant: DCM/EtOH 95/5) to afford 1.51 g of the title compound (30% yield).

¹H NMR (400 MHz, DMSO-d₆) δ ppm 2.22 (s, 3 H) 2.37 (m, 4 H) 2.42 (s, 3 H) 3.23 (m, 4 H) 6.09 (d, J=2.56 Hz, 1 H) 6.23 (dd, J=9.15 and 2.56 Hz, 1 H) 7.08 (bs, 2 H) 7.53 (d, J=9.15 Hz, 1 H).

Example 31

2-Methoxy-5-(4-methyl-piperazin-1-yl)-phenylamine

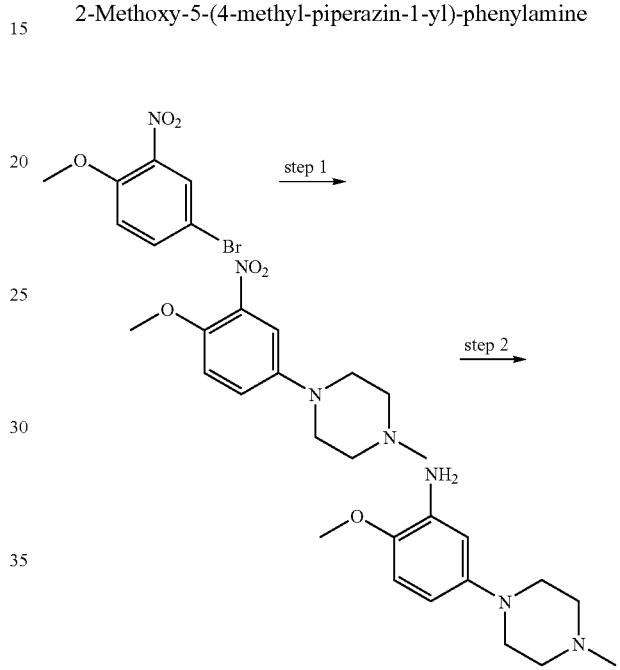

Step 1.
1-(4-Methoxy-3-nitro-phenyl)-4-methyl-piperazine

Pd(OAc)₂ (85 mg, 0.38 mmol), 2-dicyclohexylphosphino-2'-(N,N-dimethylamino)-biphenyl (225 mg, 0.57 mmol), K₃PO₄ (2.26 g, 10.68 mmol), 4-bromo-1-methoxy-2-nitro-benzene (1.77 g, 7.63 mmol) in THF (50 mL) were charged in a round-bottom flask flushed with argon. The flask was evacuated and backfilled with argon. N-methylpiperazine (1.01 mL, 9.15 mmol) was added and the reaction mixture was refluxed for 72 h. The reaction mixture was then allowed to cool to room temperature and concentrated. The crude solid was purified by flash chromatography on silica gel (eluant: DCM/EtOH 90/10) to afford 1.05 g (55% yield) of the title compound.

¹H NMR (400 MHz, DMSO-d₆) δ ppm 2.22 (s, 3 H) 2.45 (m, 4 H) 3.09 (m, 4 H) 3.83 (s, 3 H) 7.22 (d, J=9.27 Hz, 1 H) 7.26 (dd, J=9.27 and 2.93 Hz, 1 H) 7.35 (d, J=2.93 Hz, 1 H).

Step 2.
2-Methoxy-5-(4-methyl-piperazin-1-yl)-phenylamine

A solution of 1-(4-methoxy-3-nitro-phenyl)-4-methyl-piperazine (1.0 g, 4.0 mmol) in MeOH (100 mL) in the presence of Pd/C 10% (150 mg) was hydrogenated at 35 psi for 2 h. The mixture was filtered over a pad of celite and the solution was concentrated to afford 0.8 g (90% yield) of the title compound.

$^1$H NMR (400 MHz, DMSO-d$_6$) δ ppm 2.21 (s, 3 H) 2.43 (m, 4 H) 2.94 (m, 4 H) 3.68 (s, 3 H) 4.55 (s, 2 H) 6.09 (dd, J=8.66 and 2.80 Hz, 1 H) 6.30 (d, J=2.80 Hz, 1 H) 6.64 (d, J=8.66 Hz, 1H).

Example 32

1-[2-Amino-6-(4-methyl-piperazin-1-yl)-phenyl]-ethanone

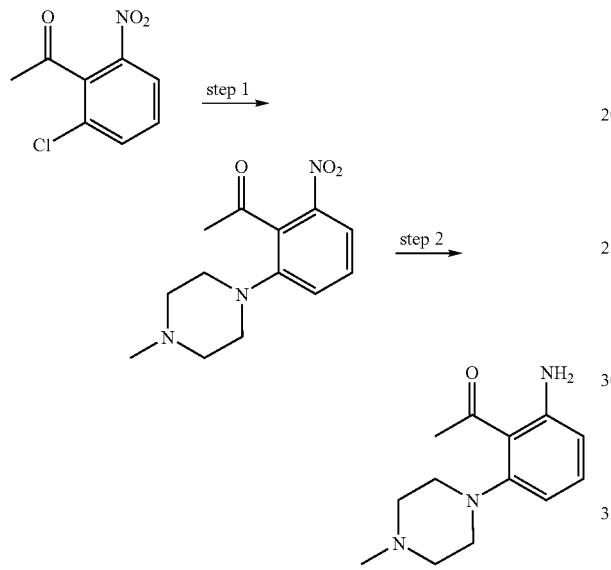

Step 1. 1-[2-(4-Methyl-piperazin-1-yl)-6-nitro-phenyl]-ethanone

In a cylindrical quartz tube were placed 1-(2-chloro-6-nitro-phenyl)-ethanone (300 mg, 1.5 mmol) and N-methyl-piperazine (12 ml, 180 mmol). The reaction was heated for 40 hours at 120° C. The solvent was removed under reduced pressure and the residue was dissolved in DCM. The solution was washed twice with water and the organic phase was dried over anhydrous Na$_2$SO$_4$. The crude was purified by flash chromatography (acetone/MeOH 75:25) affording the desired compound (272 mg, 46% yield), as a yellow solid.

Step 2. 1-[2-Amino-6-(4-methyl-piperazin-1-yl)-phenyl]-ethanone

To a solution of 1-[2-(4-methyl-piperazin-1-yl)-6-nitro-phenyl]-ethanone (270 mg, 1.02 mmol) in a mixture (1:1:1.5:2.5) of cyclohexene:THF:H$_2$O:EtOH (12 ml), Pd/C 10% (328 mg) and two drops of HCl 37% were added. The mixture was heated at 70° C. for 3 hours. The Pd was filtered from the reaction and the solvents were removed from the filtrate under reduced pressure. The crude was purified by flash chromatography (DCM/MeOH/7N NH$_3$ in methanol 9:1:1), to give the final compound (225 mg, 95% yield) as orange oil. This was treated with HCl in dioxane, in order to obtain a more manageable solid.

By working according to the same procedure the following compound was prepared:
5-(4-Methyl-piperazin-1-yl)-2-amino-benzonitrile $^1$H NMR (400 MHz, DMSO-d$_6$) δ ppm 2.25 (bs, 3 H) 2.95 (bs, 4 H) 5.49 (s, 2 H) 6.74 (d, J=9.02 Hz, 1 H) 6.85 (d, J=2.80 Hz, 1 H) 7.10 (dd, J=9.08, 2.87 Hz, 1 H).

Example 33

2-Methyl-5-(4-methyl-piperazin-1-yl)-phenylamine hydrochloride salt

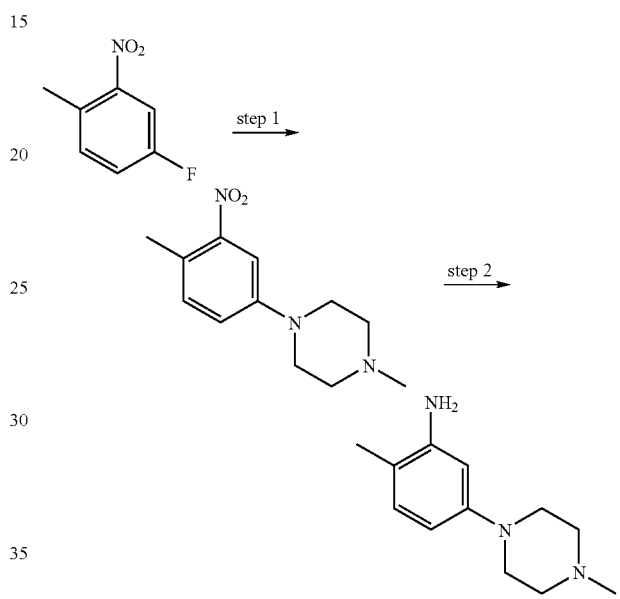

Step 1.
Methyl-4-(4-methyl-3-nitro-phenyl)-piperazine

In a cylindrical quartz tube were placed 4-fluoro-1-methyl-2-nitro-benzene (20.0 g, 129 mmol) and N-methyl-piperazine (26 g, 258 mmol). The reaction was heated for 48 hours at 200° C. The solvent was removed under reduced pressure and the residue was dissolved in DCM. The solution was washed twice with water and the organic phase was dried over anhydrous Na$_2$SO$_4$ and the solvent was removed under reduced pressure. The final compound (14.65 g, 48% yield) was obtained as a brown oil.

Step 2.
2-Methyl-5-(4-methyl-piperazin-1-yl)-phenylamine

To a solution of 1-methyl-4-(4-methyl-3-nitro-phenyl)-piperazine (9.0 g, 38.29 mmol) in ethanol (100 mL) and cyclohexene (7 ml), Pd/C 10% (1.5 g) was added. The mixture was heated at 80° C. for 6 hours. The Pd was filtered from the reaction and the solvents were removed from the filtrate under reduced pressure. The crude was diluted with DCM and treated with HCl in dioxane; the precipitate was collected and washed with diethyl ether to give the final compound as a brown solid in quantitative yield.

$^1$H NMR (400 MHz, DMSO-d$_6$) δ ppm 2.10 (s, 3 H) 2.82 (s, 3 H) 2.91-3.01 (m, 2 H) 3.06-3.21 (m, 2 H) 3.49 (d, J=14.02 Hz, 2 H) 3.66 (d, J=12.44 Hz, 2 H) 6.57 (bs, 1 H) 6.63 (bs, 1 H) 7.01 (d, J=7.68 Hz, 1 H) 10.21 (bs, 1 H).

Example 34

N-(5-Bromo-2-trifluoromethoxy-phenyl)-guanidine

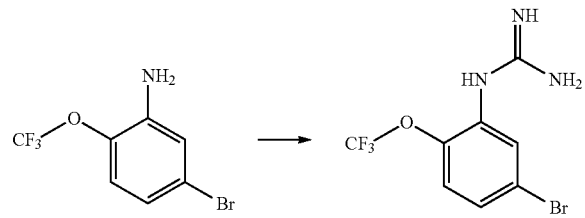 [SMILES: Nc1cc(Br)ccc1OC(F)(F)F ; N=C(N)Nc1cc(Br)ccc1OC(F)(F)F]

To a suspension of 5-bromo-2-trifluoromethoxy-phenylamine (5.0 g, 19.5 mmol) in EtOH (15 mL), cyanamide (1.64 g, 39 mmol) dissolved in 5 mL of EtOH and 1 mL $H_2O$, and HCl 37% (3.25 mL) diluted in 10 mL EtOH were added drop wise into the mixture under stirring. The mixture was refluxed for 72 h. The mixture was cooled down to room temperature, concentrated then diluted with water; NaOH 1N was added to basic pH and extracted several times with ethyl acetate, dried over sodium sulfate and concentrated to afford 5.2 g of the title compound (89% yield).

$^1$H NMR (400 MHz, DMSO-$d_6$) δ ppm 5.40 (s, 4 H) 6.98 (dd, J=8.72, 2.38 Hz, 1 H) 7.05 (d, J=1.83 Hz, 1 H) 7.11 (m, 1 H).

Example 35

N-[5-(4-Methyl-piperazin-1-yl)-2-trifluoromethoxy-phenyl]-guanidine

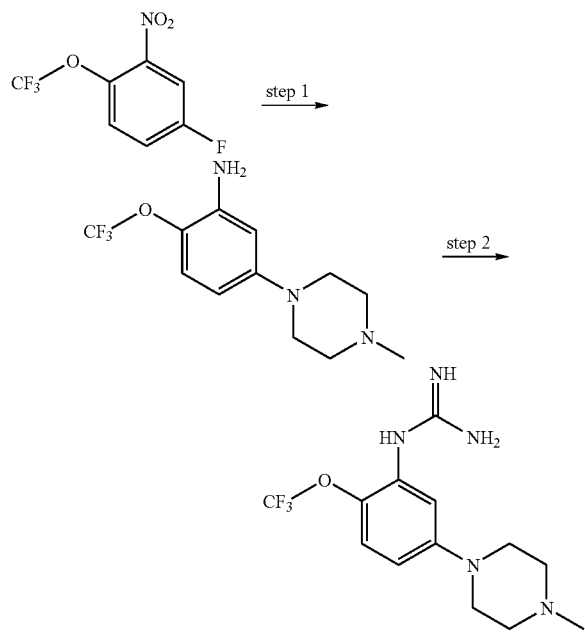

Step 1. 5-(4-Methyl-piperazin-1-yl)-2-trifluoromethoxy-phenylamine

Tris(dibenzilideneacetone)dipalladium, $Pd_2(dba)_3$ (1.1 g, 1.2 mmol), 2-dicyclohexylphosphino-2'-(N,N-dimethylamino)-biphenyl (0.94 g, 2.4 mmol), 5-bromo-2-trifluoromethoxy-phenylamine (30.7 g, 120 mmol) in THF (50 mL) were charged in a round-bottom flask flushed with argon. The flask was evacuated and backfilled with argon. $LiN(TMS)_2$ solution (1M in THF, 288 mL) and N-methylpiperazine (26.7 mL, 194 mmol) were added and the reaction refluxed for 1 h. The reaction mixture was then allowed to cool to room temperature and filtered through a pad of celite. The organic phase was concentrated, the residue dissolved in DCM (200 ml) and washed with water (1×100 ml). The organic phases were dried over anhydrous $Na_2SO_4$, the solvent evaporated in vacuo and the crude solid was purified by flash chromatography on silica gel (eluant: DCM/EtOH 90/10) to afford 21.1 g of 5-(4-methyl-piperazin-1-yl)-2-trifluoromethoxy-phenylamine (64% yield) as a light brown powder.

$^1$H NMR (400 MHz, DMSO-$d_6$) δ ppm 2.23 (s, 3 H) 2.42-2.47 (m, 4 H) 3.02-3.08 (m, 4 H) 5.10 (s, 2 H) 6.16 (dd, J=8.90, 2.93 Hz, 1 H) 6.33 (d, J=2.93 Hz, 1 H) 6.90 (dd, J=8.90, 1.46 Hz, 1 H).

By working according to the same procedure the following compounds were prepared:

N-[2-Amino-4-(4-methyl-piperazin-1-yl)-phenyl]-acetamide $^1$H NMR (400 MHz, DMSO-$d_6$) δ ppm 2.03 (s, 3 H) 2.23 (s, 3 H) 2.42-2.47 (m, 4 H) 3.02-3.08 (m, 4 H) 5.10 (s, 2 H) 6.70 (dd, J=8.72, 2.74 Hz, 1 H) 7.22 (d, J=9.02 Hz, 1 H) 7.34 (d, J=2.80 Hz, 1 H);

5-((S)-2-Benzyloxymethyl-4-methyl-piperazin-1-yl)-2-trifluoromethoxy-phenylamine $^1$H NMR (400 MHz, DMSO-$d_6$) δ ppm 2.87 (s, 3 H) 4.46-4.50 (m, 1 H) 4.52-4.56 (m, 1 H) 6.21 (dd, J=9.02, 2.93 Hz, 1 H) 6.37 (d, J=3.05 Hz, 1 H) 6.93-6.97 (m, 1 H) 7.22-7.38 (m, 5 H) 10.19 (br. s., 1 H);

5-((R)-2-Benzyloxymethyl-4-methyl-piperazin-1-yl)-2-trifluoromethoxy-phenylamine.

Step 2. N-[5-(4-Methyl-piperazin-1-yl)-2-trifluoromethoxy-phenyl]-guanidine

To a solution of 5-(4-methyl-piperazin-1-yl)-2-trifluoromethoxy-phenylamine (275 mg, 1 mmol) in HCl 6N (1 mL), cyanamide (336 mg, 8.0 mmol) was added and the reaction was stirred at 60° C. for 1 h. The mixture was cooled down to room temperature, diluted with water (3 mL), extracted with DCM (10 mL). NaOH 2N was added to pH>11. The aqueous phase was extracted with $Et_2O$ (3×10 mL), dried over sodium sulfate and concentrated. The residue was crystallized from diethyl ether to give the title compound (240 mg, 76% yield) as a white solid.

¹H NMR (400 MHz, DMSO-d₆) δ ppm 2.21 (s, 3 H) 2.39-2.45 (m, 4 H) 3.05-3.11 (m, 4 H) 6.40 (br. s., 1 H) 6.45 (dd, J=8.90, 3.05 Hz, 1 H) 6.99 (dd, J=8.96, 1.16 Hz, 1 H).

Example 36

Ethyl 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (A51B5C2Z)

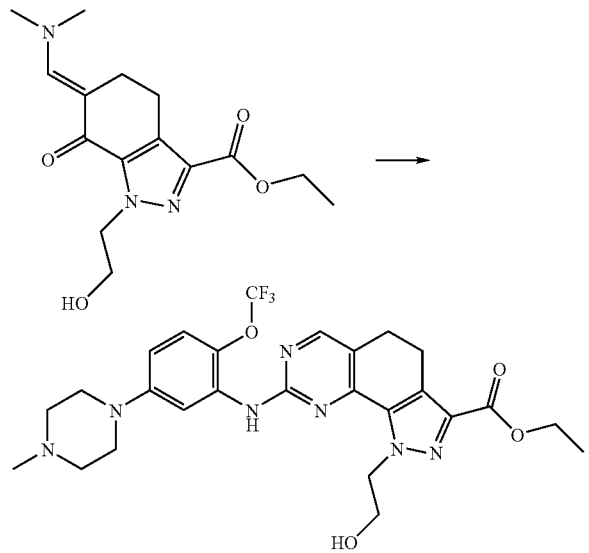

To a solution of 2.66 g (8.34 mmol) of ethyl 6-[(dimethylamino)methylene]-7-oxo-1-(2-hydroxy-ethyl)-4,5,6,7-tetrahydro-1H-indazole-3-carboxylate in 15 mL of DMF, 2.64 g (8.34 mmol) of N-[5-(4-methyl-piperazin-1-yl)-2-trifluoromethoxy-phenyl]-guanidine was added. The mixture was stirred for 4 h at 110° C. After cooling the mixture was poured into water (100 mL) and stirred for 30 minutes. The precipitate was filtered, washed with water and dried to yield 2.86 g of title compound (61%).

¹H NMR (401 MHz, DMSO-d₆) δ ppm 1.31 (t, J=7.07 Hz, 3 H) 2.23 (s, 3 H) 2.43-2.48 (m, 4 H) 2.83 (t, J=7.68 Hz, 2 H) 2.94-3.00 (m, 2 H) 3.12-3.18 (m, 4 H) 3.55-3.64 (m, 2 H) 4.29 (q, J=7.15 Hz, 2 H) 4.59 (t, J=5.67 Hz, 1 H) 4.65 (t, J=5.37 Hz, 2 H) 6.80 (dd, J=9.15, 3.05 Hz, 1 H) 7.21 (s, 1 H) 7.21-7.24 (m, 1 H) 8.36 (s, 1 H) 8.90 (s, 1 H).

Example 37

Potassium 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (A51B5C3Z)

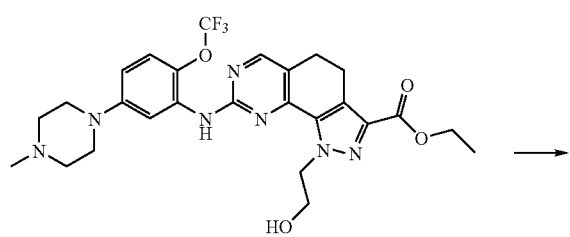

-continued

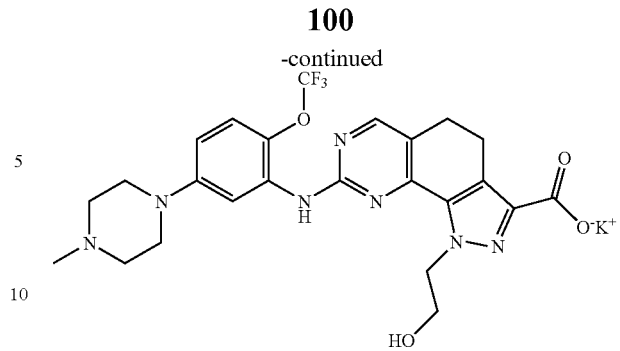

Ethyl 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (1.7 g, 3.03 mmol) was suspended in ethanol 96% (50 mL) and treated with a 1.5 M solution of potassium hydroxide in ethanol (8 mL, 12 mmol) at room temperature, overnight. The precipitate was collected by filtration to give the title compound (1.54 g, 89% yield) as a white solid.

¹H NMR (400 MHz, DMSO-d₆) δ ppm 2.22 (s, 3 H) 2.42-2.48 (m, 4 H) 2.72 (t, J=7.74 Hz, 2 H) 2.93 (t, J=7.62 Hz, 2 H) 3.12-3.17 (m, 4 H) 3.57-3.63 (m, 2 H) 4.53-4.59 (m, 3 H) 6.76 (dd, J=9.15, 3.05 Hz, 1 H) 7.20 (dd, J=9.02, 1.34 Hz, 1 H) 7.32 (d, J=2.93 Hz, 1 H) 8.26 (s, 1 H) 8.65 (s, 1 H).

Example 38

1-(2-Hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B5C1Z)

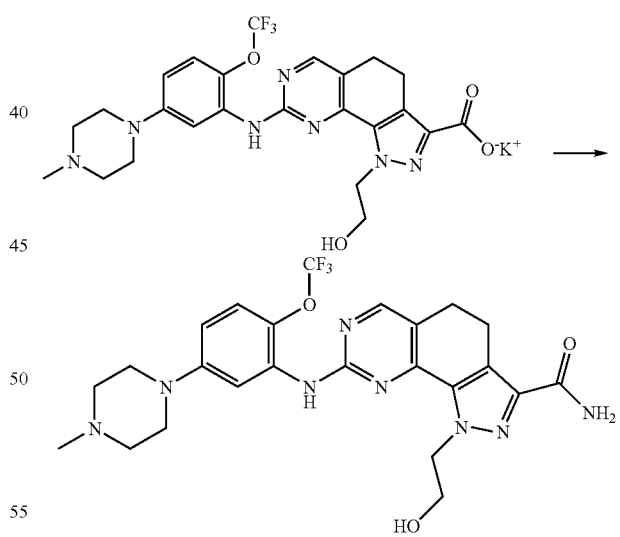

A suspension of potassium 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (1.54 g, 2.69 mmol) in anhydrous DMA (40 mL) was treated with N-ethyl-N',N'-diisopropyl carbodiimide hydrochloride (EDCI) (1.03 g, 5.38 mmol) and with ammonium 1H-1,2,3-benzotriazol-1-ate (0.819 g, 5.38 mmol). The reaction was stirred at room temperature overnight. The reaction was diluted with water and the resulting precipitate was collected by filtration to afford the title compound (1.32 g, 88% yield).

¹H NMR (400 MHz, DMSO-d₆) δ ppm 2.24 (s, 3 H) 2.46 (br. s., 4 H) 2.80 (t, J=7.62 Hz, 2 H) 2.98 (t, J=7.62 Hz, 2 H) 3.15 (br. s., 4 H) 3.64 (q, J=5.49 Hz, 2 H) 4.59 (t, J=5.79 Hz, 1 H) 4.63 (t, J=5.37 Hz, 2 H) 6.79 (dd, J=8.96, 2.99 Hz, 1 H) 7.19-7.24 (m, 1 H) 7.24 (br. s., 1 H) 7.25 (d, J=2.93 Hz, 1 H) 7.43 (s, 1 H) 8.34 (s, 1 H) 8.85 (s, 1 H).

Example 39

8-[5-(4-Methyl-piperazin-1-yl)-2-trifluoromethoxy-phenylamino]-4,5-dihydro-1H-pyrazolo[4,3-h]quinazoline-3-carboxamide (A51B8C1Z)

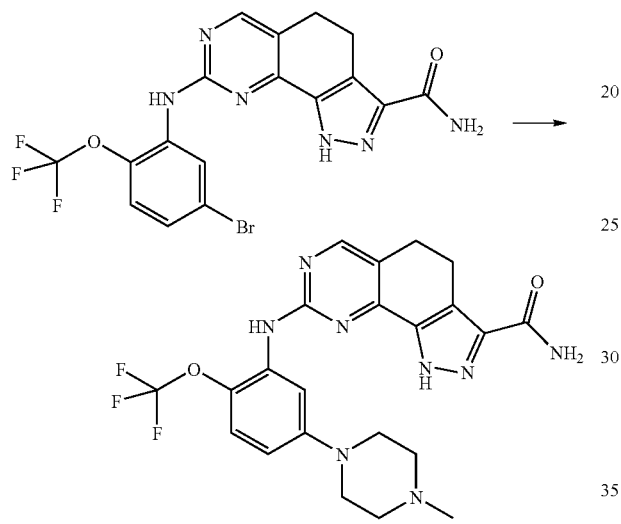

Tris(dibenzilideneacetone)dipalladium, Pd₂(dba)₃, (2.3 g, 2.5 mmol), 2-dicyclohexylphosphino-2'-(N,N-dimethylamino)-biphenyl (950 mg, 2.4 mmol), 8-[5-bromo-2-trifluoromethoxy-phenylamino]-4,5-dihydro-1H-pyrazolo[4,3-h]quinazoline-3-carboxamide (14.8 g, 31.54 mmol) in THF (160 mL) were charged in a round-bottom flask flushed with argon. The flask was evacuated and backfilled with argon. LiN(TMS)₂ solution (1M in THF, 630 mL) and N-methylpiperazine (69 mL, 50.64 mmol) were added and the reaction mixture refluxed for 1 h. The reaction mixture was then allowed to cool to room temperature and filtered through a pad of celite. The organic phase was concentrated. The crude solid was purified by flash chromatography on silica gel (eluant: DCM/MeOH 95/5) to afford 9.2 g (60% yield) of the title compound.

¹H NMR (400 MHz, DMSO-d₆) δ ppm 2.22 (s, 3 H) 2.45-2.48 (m, 4 H) 2.84 (t, J=7.62 Hz, 2 H) 3.00 (t, J=7.50 Hz, 2 H) 3.16-3.20 (m, 4 H) 6.71 (br. s., 1 H) 7.19 (dd, J=9.02, 1.34 Hz, 1 H) 7.32 (br. s., 1 H) 7.49 (br. s., 1 H) 8.34 (br. s., 1 H) 8.36 (s, 1H).

Example 40

1-(2-Chloro-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B9C1Z)

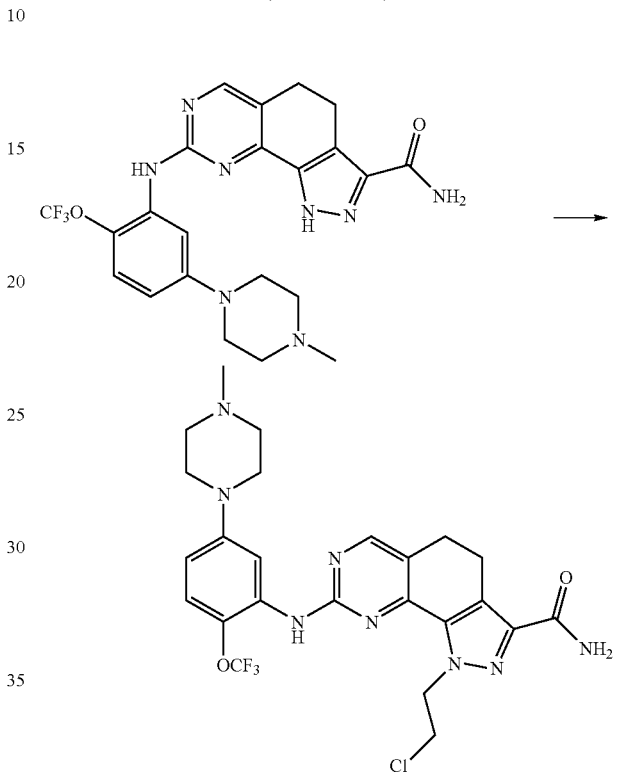

A suspension of 8-[5-(4-methyl-piperazin-1-yl)-2-trifluoromethoxy-phenylamino]-4,5-dihydro-1H-pyrazolo[4,3-h]quinazoline-3-carboxamide (488 mg, 1.0 mmol) and Cs₂CO₃ (490 mg, 1.5 mmol) was suspended in DMF (1 mL) and treated with 1-bromo-2-chloro-ethane (0.1 mL, 1.2 mmol) at room temperature. After 2 h the reaction mixture was poured into water and filtered, washed with water and dried to give the title compound (529 mg, 96% yield) as a white solid.

¹H NMR (400 MHz, DMSO-d₆) δ ppm 2.22 (s, 3 H) 2.42-2.48 (m, 4 H) 2.81 (t, J=7.68 Hz, 2H) 2.99 (t, J=7.80 Hz, 2 H) 3.12-3.18 (m, 4 H) 3.84 (t, J=5.91 Hz, 2 H) 4.87 (t, J=5.91 Hz, 2 H) 6.81 (dd, J=9.08, 2.99 Hz, 1 H) 7.19 (d, J=2.93 Hz, 1 H) 7.21-7.26 (m, 1 H) 7.29-7.33 (m, 1 H) 7.46 (s, 1 H) 8.36 (s, 1 H) 8.92 (s, 1 H).

By working according to the same procedure the following compounds were prepared:

TABLE XX

| Code | NMR data |
|---|---|
| A51B14C1Z | ¹H NMR (400 MHz, DMSO-d₆) δ ppm 1.65-1.74 (m, 2 H) 1.92 (t, J = 6.95 Hz, 2 H) 1.99 (s, 6 H) 2.22 (s, 3 H) 2.42-2.46 (m, 4 H) 2.77-2.84 (m, 2 H) 2.94-3.01 (m, 2 H) 3.12-3.18 (m, 4 H) 4.54 (t, J = 7.26 Hz, 2 H) 6.80 (dd, J = 9.08, 2.99 Hz, 1 H) 7.20-7.23 (m, 2 H) 7.24 (br. s., 1 H) 7.40 (s, 1 H) 8.36 (s, 1 H) 8.85 (s, 1 H) |

TABLE XX-continued

| Code | NMR data |
|---|---|
| A51B15C1Z | ¹H NMR (400 MHz, DMSO-d₆) δ ppm 2.23 (s, 3 H) 2.43-2.47 (m, 4 H) 2.77-2.83 (m, 2 H) 2.95-3.01 (m, 2 H) 3.06 (s, 3 H) 3.13-3.17 (m, 4 H) 3.54 (t, J = 5.43 Hz, 2 H) 4.72 (t, J = 5.43 Hz, 2 H) 6.81 (dd, J = 9.02, 2.93 Hz, 1 H) 7.20 (d, J = 3.29 Hz, 1 H) 7.23 (d, J = 1.10 Hz, 1 H) 7.26 (br. s., 1 H) 7.40 (s, 1 H) 8.35 (s, 1 H) 8.91 (s, 1 H) |
| A49B11C1Z | ¹H NMR (400 MHz, DMSO-d₆) δ ppm 2.78-2.85 (m, 2 H) 2.96-3.03 (m, 2 H) 3.67 (s, 3 H) 5.80 (s, 2 H) 6.70-6.75 (m, 2 H) 6.99-7.06 (m, 2 H) 7.30 (s, 1 H) 7.36 (s, 2 H) 7.48 (s, 1 H) 8.14 (s, 1 H) 8.41 (s, 1 H) 9.33 (s, 1 H) |
| A45B5C1Z | ¹H NMR (400 MHz, DMSO-d₆) δ ppm 2.79 (m, 2 H) 2.98 (m, 2 H) 3.64 (m, 1 H) 3.80 (m, 1 H) 4.74 (m, 1 H) 4.90 (m, 1 H) 7.22 (m, 1 H) 7.25 (bs, 1 H) 7.39 (m, 2 H) 7.42 (bs, 1 H) 7.87 (m, 1 H) 8.38 (s, 1 H) 9.03 (s, 1 H) |
| A51B5C1Z | ¹H NMR (400 MHz, DMSO-d₆) δ ppm 2.24 (s, 3 H) 2.46 (br. s., 4 H) 2.80 (t, J = 7.62 Hz, 2 H) 2.98 (t, J = 7.62 Hz, 2 H) 3.15 (br. s., 4 H) 3.64 (q, J = 5.49 Hz, 2 H) 4.59 (t, J = 5.79 Hz, 1 H) 4.63 (t, J = 5.37 Hz, 2 H) 6.79 (dd, J = 8.96, 2.99 Hz, 1 H) 7.19-7.24 (m, 1 H) 7.24 (br. s., 1 H) 7.25 (d, J = 2.93 Hz, 1 H) 7.43 (s, 1 H) 8.34 (s, 1 H) 8.85 (s, 1 H) |

Example 41

8-[5-(4-Methyl-piperazin-1-yl)-2-trifluoromethoxy-phenylamino]-1-vinyl-4,5-dihydro-1H-pyrazolo[4,3-h]quinazoline-3-carboxamide (A51B10C1Z)

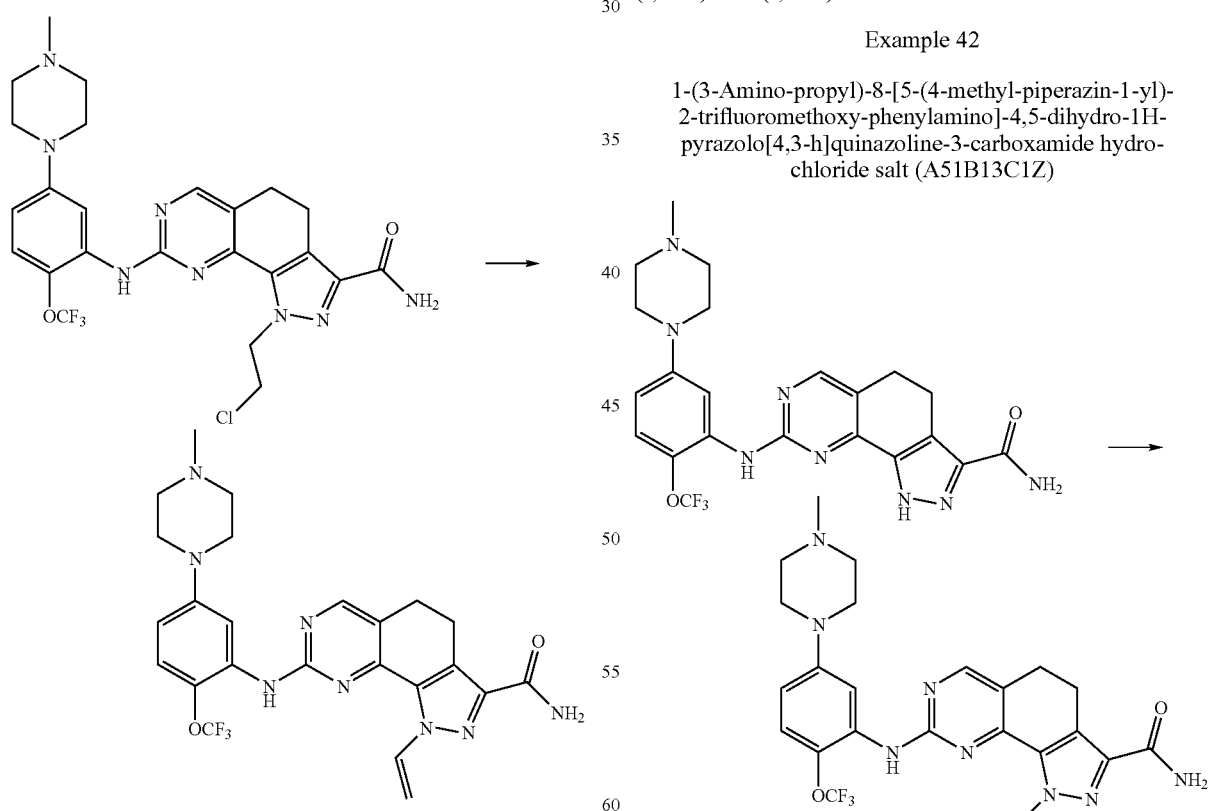

A mixture of 1-(2-chloro-ethyl)-8-[5-(4-methyl-piperazin-1-yl)-2-trifluoromethoxy-phenylamino]-4,5-dihydro-1H-pyrazolo[4,3-h]quinazoline-3-carboxamide (350 mg, 0.63 mmol) and DBU (3.5 mL) was heated to 80° C. for 1 h. After cooling the reaction mixture was poured into water and filtered. The crude solid was purified by flash chromatography on silica gel (eluant: DCM/MeOH 95/5) to afford 234 mg (71% yield) of the title compound.

¹H NMR (400 MHz, DMSO-d₆) δ ppm 2.22 (s, 3 H) 2.39-2.47 (m, 4 H) 2.83 (t, J=7.80 Hz, 2 H) 3.01 (t, J=7.74 Hz, 2 H) 3.12-3.20 (m, 4 H) 4.90 (d, J=8.7 Hz, 1 H) 5.89 (d, J=15.4 Hz, 1 H) 6.81 (dd, J=9.15, 2.93 Hz, 1 H) 7.18-7.32 (m, 2 H) 7.43 (s, 1 H) 7.66 (s, 1 H) 8.33 (dd, J=15.4, 8.7 Hz, 1 H) 8.39 (s, 1 H) 9.05 (s, 1 H).

Example 42

1-(3-Amino-propyl)-8-[5-(4-methyl-piperazin-1-yl)-2-trifluoromethoxy-phenylamino]-4,5-dihydro-1H-pyrazolo[4,3-h]quinazoline-3-carboxamide hydrochloride salt (A51B13C1Z)

A suspension of 8-[5-(4-methyl-piperazin-1-yl)-2-trifluoromethoxy-phenylamino]-4,5-dihydro-1H-pyrazolo[4,3-h]quinazoline-3-carboxamide (100 mg, 0.2 mmol) and $Cs_2CO_3$ (97.5 mg, 0.3 mmol) was suspended in DMF (0.5 mL) and treated with (3-bromo-propyl)-carbamic acid tert-butyl ester (71 mg, 0.3 mmol) at room temperature. After 2 h the reaction mixture was poured into water and filtered, washed with water and dried. The residue was suspended in dioxane (1 mL) and treated with HCl 4N in dioxane (0.1 mL) for 1 h. The precipitate was filtered and dried to give the title compound (52 mg, 45% yield) as a white solid.

$^1$H NMR (400 MHz, DMSO-$d_6$) δ ppm 1.89-2.01 (m, 2 H) 2.63-2.72 (m, 2 H) 2.79-2.86 (m, 2 H) 2.84 (d, J=4.63 Hz, 3 H) 2.96-3.04 (m, 2 H) 3.07-3.24 (m, 4 H) 3.38-3.42 (m, 2 H) 3.84 (d, J=11.83 Hz, 2 H) 4.71 (t, J=6.46 Hz, 2 H) 6.89 (dd, J=9.21, 2.99 Hz, 1 H) 7.30 (dd, J=8.96, 1.16 Hz, 1 H) 7.33-7.37 (m, 2 H) 7.46 (br. s., 1 H) 7.92 (br. s., 3 H) 8.38 (s, 1 H) 9.09 (s, 1 H).

By working according to the same procedure the following compound was prepared:
1-(3-Amino-ethyl)-8-[5-(4-methyl-piperazin-1-yl)-2-trifluoromethoxy-phenylamino]-4,5-dihydro-1H-pyrazolo[4,3-h]quinazoline-3-carboxamide hydrochloride salt (A51B12C1Z)

$^1$H NMR (400 MHz, DMSO-$d_6$) δ ppm 2.80-2.84 (m, 2 H) 2.86 (d, J=4.76 Hz, 3 H) 2.97-3.03 (m, 2 H) 3.06-3.28 (m, 4 H) 3.81 (d, J=0.61 Hz, 2 H) 4.90-4.96 (m, 2 H) 6.87 (dd, J=9.08, 2.99 Hz, 2 H) 7.28-7.33 (m, 2 H) 7.38 (br. s., 2 H) 7.41 (d, J=2.68 Hz, 1 H) 7.75 (br. s., 1 H) 8.19 (br. s., 3 H) 8.38 (s, 1 H) 9.17 (s, 1 H).

Example 43

5-(1-Methyl-piperidin-4-yl)-2-trifluoromethoxy-phenylamine

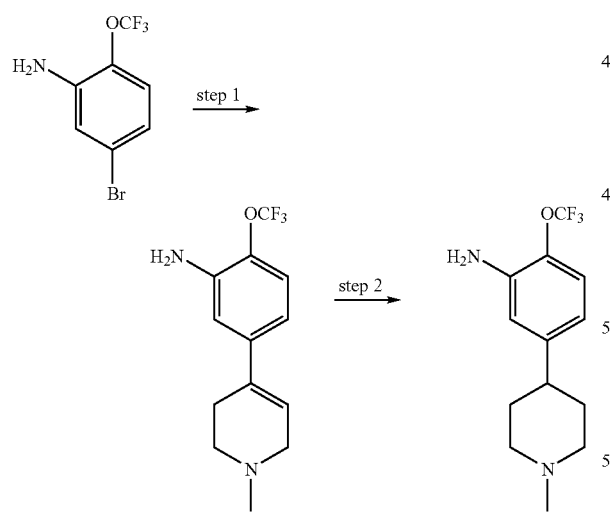

Step 1. 5-(1-Methyl-1,2,3,6-tetrahydro-pyridin-4-yl)-2-trifluoromethoxy-phenylamine 5-Bromo-2-trifluoromethoxy-phenylamine (0.43 g, 1.68 mmol), cesium carbonate (1.65 g, 5.06 mmol), 1,1'-bis(diphenylphosphino)ferrocenepalladium(ii) dichloride, complex with dichloromethane (1:1) (0.08 g, 0.1 mmol) in dry DMF (20 mL) were charged in a round-bottom flask flushed with argon. The flask was evacuated and backfilled with argon. A solution of 1-methyl-4-(4,4,5,5-tetramethyl-[1,3,2]dioxaborolan-2-yl)-1,2,3,6-tetrahydro-pyridine (0.45 g, 2.01 mmol) in dry DMF (10 mL) were added to the suspension and the reaction mixture warmed at 80° C. for 3 hours. The reaction mixture was then allowed to cool to room temperature, diluted with water (100 mL) and extracted with DCM (2×50 mL) and the combined organic phases were extracted with 1N HCl solution (50 mL). The aqueous layer was basified by addition of sodium bicarbonate and extracted with EtOAc (2×50 mL). The combined organic phases were dried over anhydrous $Na_2SO_4$, the solvent removed under reduced pressure and the crude solid purified by flash chromatography on silica gel (eluant: DCM/MeOH 90/10) to afford the intermediate as a light brown solid (0.3 g, 65% yield)

$^1$H NMR (400 MHz, DMSO-$d_6$) δ ppm 2.29 (s, 3 H) 2.38-2.44 (m, 2 H) 2.58 (t, J=5.55 Hz, 2 H) 3.02 (d, J=2.32 Hz, 2 H) 5.29 (s, 2 H) 6.03 (t, J=3.48 Hz, 1 H) 6.64 (dd, J=8.54, 2.19 Hz, 1 H) 6.86 (d, J=2.32 Hz, 1 H) 7.03 (dd, J=8.54, 1.34 Hz, 1 H).

Step 2. 5-(1-Methyl-piperidin-4-yl)-2-trifluoromethoxy-phenylamine

A suspension of 5-(1-methyl-1,2,3,6-tetrahydro-pyridin-4-yl)-2-trifluoromethoxy-phenylamine (0.3 g, 1.10 mmol), 10% Pd/C catalyst (100 mg) in EtOH (20 mL) was hydrogenated at 40 psi for 6 hours into a Parr apparatus. The mixture was filtered over a pad of celite, the solvent removed under vacuum and the crude residue purified by flash chromatography on silica gel (eluant: DCM/MeOH/$NH_3$ 95/05/005) to yield the title compound as a light brown solid (0.17 g, 56% yield).

$^1$H NMR (400 MHz, DMSO-$d_6$) δ ppm 1.56 (qd, J=12.32, 3.54 Hz, 2 H) 1.68 (d, J=11.80 Hz, 2 H) 1.93 (t, J=11.20 Hz, 2 H) 2.18 (s, 3 H) 2.30 (tt, J=12.00, 3.66 Hz, 1H) 2.84 (d, J=11.34 Hz, 2 H) 5.22 (s, 2 H) 6.43 (dd, J=8.41, 2.07 Hz, 1 H) 6.67 (d, J=2.19 Hz, 1 H) 6.98 (dq, J=8.37, 1.50 Hz, 1 H).

Example 44

5-((R)-2-Benzyloxymethyl-4-methyl-piperazin-1-yl)-2-trifluoromethoxy-phenylamine

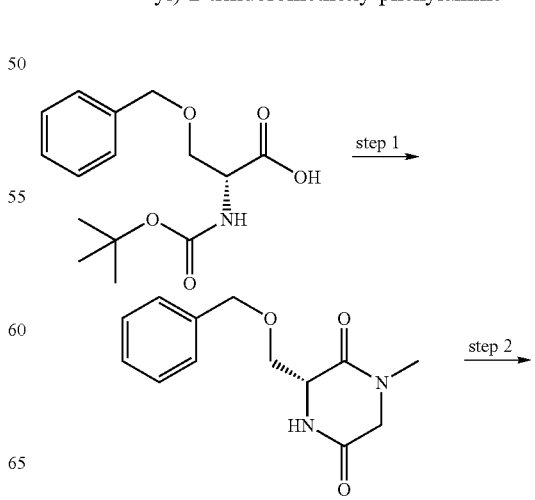

Step 1. (R)-3-Benzyloxymethyl-1-methyl-piperazine-2,5-dione

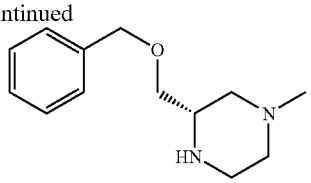

To a solution of sarcosine methyl ester hydrochloride (2.8 g, 18.6 mmol) in DMF dry (43 mL), DIPEA (3 ml, 16.9 mmol) was added and the mixture was stirred at room temperature for 20 min. Then THF (160 mL), EDDQ hydrochloride (3.2 g, 16.9 mmol) and BOC-D-Serine (5.0 g, 16.9 mmol) were added and the reaction mixture was stirred at the same temperature for 2 h. The solvent was removed under reduced pressure and the residue was dissolved in AcOEt. The solution was washed with water, 1N HCl and NaHCO$_3$ saturated solution and the organic phase was dried over anhydrous Na$_2$SO$_4$. Concentration of the solution gave 5 g (75% yield) of colourless oil that was diluted in DCM (325 mL). TFA (325 mL) was added and the mixture was stirred at room temperature for 2 h. The solvent was removed under reduced pressure and the residue was dissolved in MeOH (400 mL). TEA (21.5 mL, 149 mmol) was added and the solution was refluxed under N$_2$ atmosphere for 2 h. The solvent was removed under reduced pressure and the residue was dissolved in DCM. The solution was washed twice with water and the organic phase was dried over anhydrous Na$_2$SO$_4$. The solvent was removed under reduced pressure and the crude was diluted with Et$_2$O and decanted to give the final compound (1.93 g, 63% yield) as a white solid.

$^1$H NMR (400 MHz, DMSO-d$_6$) δ ppm 2.83 (s, 3 H) 3.56 (dd, J=9.63, 2.80 Hz, 1H) 3.77-3.83 (m, 2 H) 3.87-3.92 (m, 1H) 3.95 (q, J=2.68 Hz, 1H) 4.45-4.53 (m, 2 H) 7.25-7.31 (m, 3 H) 7.33-7.38 (m, 2 H) 8.23 (br. s., 1H).

By working according to the same procedure but using BOC-L-Serine the following compound was prepared:

(S)-3-Benzyloxymethyl-1-methyl-piperazine-2,5-dione.

Step 2. (S)-3-Benzyloxymethyl-1-methyl-piperazine

To a solution of (R)-3-Benzyloxymethyl-1-methyl-piperazine-2,5-dione (1.93 g, 7.78 mmol) in THF (30 mL), LiAlH$_4$ 1M in THF (15 mL, 15.5 mmol) was added dropwise over 30 min and the solution was refluxed under N$_2$ atmosphere for 3 h. The reaction was cooled to 0° C. and diluted with water (100 mL). Then 4 mL of a 15% aqueous NaOH solution was added. After 1 h 100 mL of water was added and the reaction stirred overnight. The white precipitate was filtered out and washed with DCM. The solvent was removed under reduced pressure and the residue was diluted with Et$_2$O and decanted. The crude was purified by flash chromatography (DCM/MeOH/7N NH$_3$ in methanol, 90:9:1) to give the desired compound (1.43 g, 83.5% yield) as yellow oil.

$^1$H NMR (400 MHz, DMSO-d$_6$) δ ppm 1.61 (t, J=10.12 Hz, 1 H) 1.85 (td, J=10.82, 3.23 Hz, 1 H) 2.13 (s, 3 H) 2.57-2.67 (m, 4 H) 2.83-2.89 (m, 1 H) 3.29-3.34 (m, 2 H) 4.47 (s, 2 H) 7.23-7.40 (m, 5 H).

By working according to the same procedure the following compound was prepared:

(R)-3-Benzyloxymethyl-1-methyl-piperazine.

Example 45

8-[5-((S)-2-Hydroxymethyl-4-methyl-piperazin-1-yl)-2-trifluoromethoxy-phenylamino]-1-methyl-4,5-dihydro-1H-pyrazolo[4,3-h]quinazoline-3-carboxamide (A117B1C1Z)

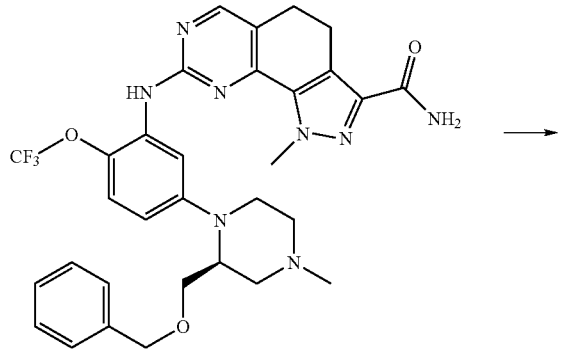

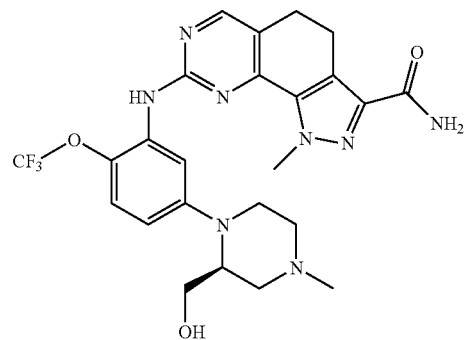

To a solution of 8-[5-((S)-2-benzyloxymethyl-4-methyl-piperazin-1-yl)-2-trifluoromethoxy-phenylamino]-1-methyl-4,5-dihydro-1H-pyrazolo[4,3-h]quinazoline-3-carboxamide (53 mg, 0.08 mmol) in DCM (1.7 mL) under an atmosphere of N$_2$, at −78° C. 1M BCl$_3$ in DCM (0.17 mL) was added dropwise. Under complete addition the solution was stirred at 0° C. for 30 min and at room temperature overnight. Then 2 mL of MeOH was added. The solvent was removed under reduced pressure and the residue was diluted with Et$_2$O and decanted to give the desired compound in quantitative yield (46 mg) as a brown solid.

$^1$H NMR (400 MHz, DMSO-d$_6$) δ ppm 2.79-2.84 (m, 2 H) 2.87 (s, 3 H) 2.95-3.02 (m, 2 H) 4.17 (s, 3 H) 6.82 (dd, J=9.15, 2.93 Hz, 1 H) 7.25-7.29 (m, 1 H) 7.32 (d, J=3.05 Hz, 1 H) 8.36 (s, 1 H) 9.00 (s, 1 H).

By working according to the same procedure the following compound was prepared:

8-[5-((R)-2-Hydroxymethyl-4-methyl-piperazin-1-yl)-2-trifluoromethoxy-phenylamino]-1-methyl-4,5-dihydro-1H-pyrazolo[4,3-h]quinazoline-3-carboxamide (A115B1C1Z).

Example 46

1-(2-Hydroxy-ethyl)-8-[2-trifluoromethoxy-5-(4-methyl-4-oxy-piperazin-1-yl)-phenylamino]-4,5-dihydro-1H-pyrazolo[4,3-h]quinazoline-3-carboxamide (A102B5C1Z)

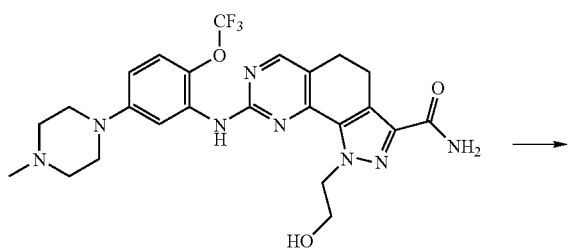

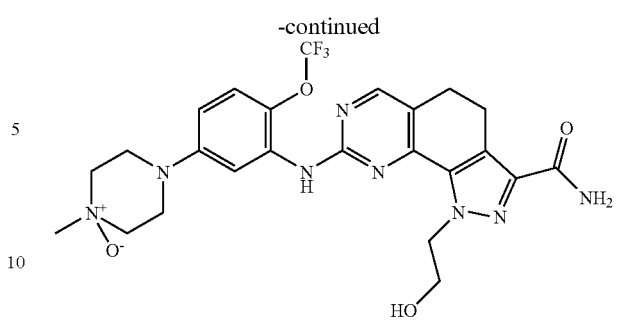

To a solution of 400 mg (0.751 mmol) of 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxamide, 17.4 mg (1.1 mmol) of 3-chlorobenzenecarboperoxoic acid were added and the mixture was stirred at room temperature. After 45 minutes an aqueous solution of $NaHCO_3$ was added and the organic phase removed. The aqueous solution was filtered through a sintered glass filter, the solid washed with water (20 mL) and finally purified by flash chromatography (eluant DCM/MeOH/$NH_3$ 80/20/02) to yield 170 mg (41% yield) of the title compound as a pale brown solid.

$^1$H NMR (400 MHz, DMSO-$d_6$) δ ppm 2.79 (t, J=7.68 Hz, 2 H) 2.97 (t, J=7.68 Hz, 2 H) 3.34 (t, J=11.50 Hz, 2 H) 3.50 (s, 3 H) 3.65 (t, J=5.42 Hz, 2 H) 3.69 (t, J=11.70 Hz, 2 H) 3.71-3.75 (m, 2 H) 3.77 (t, J=10.30 Hz, 2 H) 4.63 (t, J=5.42 Hz, 2 H) 6.88 (dd, J=9.08, 2.99 Hz, 1 H) 7.24 (br. s., 1 H) 7.28 (dq, J=9.02, 1.10 Hz, 1 H) 7.36 (d, J=2.93 Hz, 1 H) 7.39 (m, 1 H) 8.34 (s, 1 H) 8.95 (s, 1 H).

The invention claimed is:
1. A compound of formula (I):

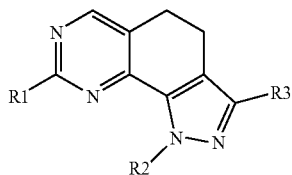

(I)

wherein
R1 is an ortho-substituted-arylamino of the formula:

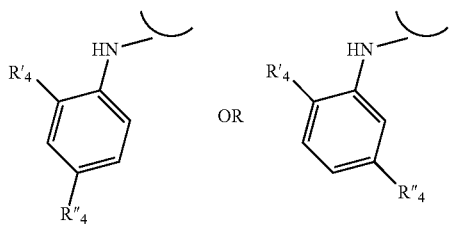

wherein R'$_4$ and R''$_4$ are independently selected from a group consisting of halogen, nitro, cyano, C$_1$-C$_6$ alkyl, polyfluorinated alkyl, polyfluorinated alkoxy, alkenyl, alkynyl, hydroxyalkyl, aryl, arylalkyl, heterocyclyl, C$_3$-C$_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate;
R2 is hydrogen or an optionally substituted group selected from straight or branched C$_1$-C$_6$ alkyl, straight or branched C$_2$-C$_6$ alkenyl, straight or branched C$_2$-C$_6$ alkynyl, C$_3$-C$_6$ cycloalkyl and heterocyclyl;
R3 is CO—OR' or CO—NR'R", wherein R' and R" are, each independently, hydrogen or an optionally substituted group selected from straight or branched C$_1$-C$_6$ alkyl, C$_3$-C$_6$ cycloalkyl and heterocyclyl, or R' and R" taken together with the nitrogen atom to which they are bonded, may form an optionally substituted heterocyclyl group optionally containing one additional heteroatom selected among N, O or S;
and isomers, tautomers, N-oxides and pharmaceutically acceptable salts thereof.
2. A compound of formula (I) as defined in claim 1 wherein:
R3 is CO—OH or CO—NR'R".
3. A compound of formula (I) as defined in claim 1 wherein:
R2 is an optionally substituted straight or branched C$_1$-C$_6$ alkyl or C$_2$-C$_6$ alkenyl.
4. A compound of formula (I) as defined in claim 1 wherein:
R3 is CO—NR'R".
5. A compound or a pharmaceutically acceptable salt thereof which is selected from the group consisting of:
8-[2-Acetyl-5-(4-methyl-piperazin-1-yl)-phenylamino]-1-methyl-4,5-dihydro-1H-pyrazolo[4,3-h]quinazoline-3-carboxamide (A39B1C1Z);
8-[2-Acetyl-5-(4-methyl-piperazin-1-yl)-phenylamino]-1-(2-fluoro-ethyl)-4,5-dihydro-1H-pyrazolo[4,3-h]quinazoline-3-carboxamide (A39B2C1Z); 1-Methyl-8-[5-(4-methyl-piperazin-1-yl)-2-trifluoromethoxy-phenylamino]-4,5-dihydro-1H-pyrazolo[4,3-h]quinazoline-3-carboxamide (A51B1C1Z);
Ethyl 1-methyl-8-[5-(4-methyl-piperazin-1-yl)-2-trifluoromethoxy-phenylamino]-4,5-dihydro-1H-pyrazolo[4,3-h]quinazoline-3-carboxylate (A51B1C2Z); 1-Methyl-8[2-methoxy-5-(4-methyl-piperazin-1-yl)-phenylamino]-1-methyl-4,5-dihydro-1H-pyrazolo[4,3-h]quinazoline-3-carboxamide (A85B1C1Z); 8-[5-(4Methyl-piperazin-1-yl)-2-trifluoromethoxy-phenylamino]-1-(2-fluoro-ethyl)-4,5-dihydro-1H-pyrazolo[4,3-h]quinazoline-3-carboxamide (A51B2C1Z);
1-Methyl-8-[4-(4-methyl-piperazin-1-yl)-2-trifluoromethoxy-phenylamino]-4,5-dihydro-1H-pyrazolo[4,3-h]quinazoline-3-carboxamide (A48B1C1Z);
1-Methyl-8-(2-trifluoromethoxy-5-piperazin-1-yl-phenylamino]-4,5-dihydro-1H-pyrazolo[4,3-h]quinazoline-3-carboxamide (A97B1C1Z);
1-Methyl-8-[2-methyl-5-(4-methyl-piperazin-1-yl)-phenylamino]-4,5-dihydro-1H-pyrazolo[4,3-h]quinazoline-3-carboxamide (A98B1C1Z);
1-Methyl-8-[5-(4-pyrrolidin-1-yl-piperidin-1-yl)-2-trifluoromethoxy phenylamino]4,5-dihydro-1H-1H-pyrazolo[4,3-h]quinazoline-3-carboxamide (A99B 1C1Z);
1-Methyl-8-[5-(4-methyl-piperazin-1-yl)-2-trifluoromethoxy-phenylamino]-4,5-dihydro-IH-pyrazolo[4,3-h]quinazoline-3-carboxylic acid methylamide (A51B1C4Z);
1-Methyl-8-[5-(4-methyl-piperazin-1-yl)-2-methoxy-phenylamino]-4,5-dihydro-1H-pyrazolo[4,3-h]quinazoline-3-carboxylic acid methylamide (A85B1C4Z);
1-Methyl-8-[2-methyl-5-(4-methyl-piperazine-1-carbonyl)-phenylamino]-4,5-dihydro-1H-pyrazolo[4,3-h]quinazoline-3-carboxamide (A87B1C1Z);
1-Methyl-8-[2-methyl-4-(4-methyl-piperazine-1-carbonyl)-phenylamino]-4,5-dihydro-1H-pyrazolo[4,3-h]quinazoline-3-carboxamide (A86B1C1Z);
1-Methyl-8-{2-trifluoromethoxy-5-[(1-methyl-piperidine-4-carbonyl)-amino]-phenylamino}-4,5-dihydro-1H-pyrazolo[4,3-h]quinazoline-3-carboxamide (A82B1C1Z);
Potassium8-[5-(4-methyl-piperazin-1-yl)-2-trifluoromethoxy-phenylamino]-1-methyl-4,5-dihydro-1H-pyrazolo[4,3-h]quinazoline-3-carboxylate (A51B1C3Z); 1-Ethyl-8-[5-(4-methyl-piperazin-1-yl)-2-trifluoromethoxy-phenylamino]-4,5-dihydro-1H-pyrazolo[4,3-h]quinazoline-3-carboxamide (A51B7C1Z);

1-Methyl-8-[5-(4-methyl-piperazin-1-yl)-2-trifluoromethoxy-phenylamino]-4,5-dihydro-1H-pyrazolo[4,3-h]quinazoline-3-carboxylic acid (2,2,2-trifluoroethyl)-amide (A51B1C7Z);
1-(2-Hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B5C1Z);
8-[5-(4-methyl-piperazin-1-yl)-2-trifluoromethoxy-phenylamino]-1-vinyl-4,5-dihydro-1H-pyrazolo[4,3-h]quinazoline-3-carboxamide (A51B10C1Z);
1-(2-Chloro-ethyl)-8-[5-(4-methyl-piperazin-1-yl)-2-trifluoromethoxy-phenylamino]-4,5-dihydro-1H-pyrazolo[4,3-h]quinazoline-3-carboxamide (A51B9C1Z);
8-[5-(4-Methyl-piperazin-1-yl)-2-trifluoromethoxy-phenylamino]-4,5-dihydro-1H-pyrazolo[4,3-h]quinazoline-3-carboxamide (A51B8C1Z);
Potassium 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (A51B5C3Z);
Ethyl 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxylate (A51B5C2Z);
1-Methyl-8-[5-(1-methyl-1,2,3,6-tetrahydro-pyridin-4-yl)-2-trifluoromethoxy-phenylamino]-4,5-dihydro-1H-pyrazolo[4,3-h]quinazoline-3-carboxamide (A113B1C1Z);
1-Methyl-8-[5-(1-methyl-piperidin-4-yl)-2-trifluoromethoxy-phenylamino]-4,5-dihydro-1H-pyrazolo[4,3-h]quinazoline-3-carboxamide (A114B1C1Z);
8-(5-Bromo-2-trifluoromethoxy-phenylamino)-1-methyl-4,5-dihydro-1H-pyrazolo[4,3-h]quinazoline-3-carboxamide (A49B1C1Z), and 8-(5-Bromo-2-trifluoromethoxy-phenylamino)-4,5-dihydro-1H-pyrazolo[4,3-h]quinazoline-3-carboxamide (A49B8C1Z).

6. A process for preparing a compound of formula (I) as defined in claim 1, which process comprises:
st.1) reacting the compound of formula (II):

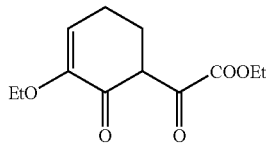

(II)

with a hydrazine derivative of formula (III):

(III)

wherein R2 and R1 are defined in claim 1, in the presence of acetic acid to give a compound of formula (IV):

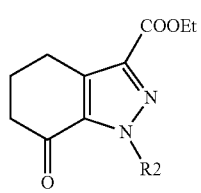

(IV)

wherein R2 is as defined above;

optionally alkylating a compound of formula (IV) wherein R2 is hydrogen with the compounds of formula (V):

(V)

wherein Y is a suitable leaving group, and R2 is as defined above but not hydrogen, to give a compound of formula (IV) wherein R2 is as defined above but not hydrogen;
st.2) reacting the compound of formula (IV) with dimethylformamide-di-tert-butylacetale or dimethylformamide-diisopropylacetale to give a compound of formula (VI):

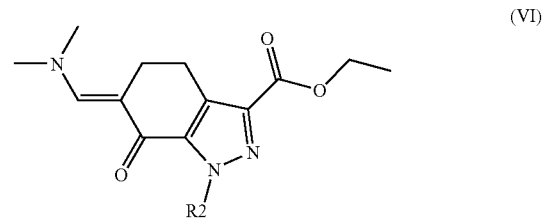

(VI)

wherein R2 is as defined above; and
st3.) reacting the compound of formula (VI) according to (st.3b):
st.3b) with a guanidine derivative of formula (X):

(X)

wherein R1 is as defined above, to give a compound of formula (I):

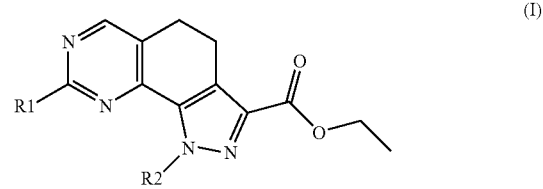

(I)

wherein R1 and R2 are as defined above, and optionally converting it into a pharmaceutically acceptable salt thereof.

7. A process for preparing a compound of formula (I) according to claim 6, characterized in that the compound of formula (I) is prepared according to a process which comprises:
st.4.) converting the ethoxycarbonyl group of a compound of formula (VIII):

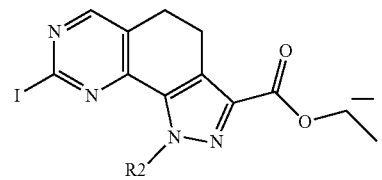

to a compound of formula (XIII) or corresponding salt through basic hydrolysis; converting the resulting compound of formula (XIII) or corresponding salt into the compound of formula (XIV) through reaction under basic conditions and in presence of a suitable condensing agent, with an amine of formula R'R"—NH (XI); reacting the compound of formula (XIV) with an orthosubstituted-arylamine of formula R1-H (IX), to obtain a compound of formula (I), wherein R1, R2, R' and R" are as defined above and optionally converting it into a pharmaceutically acceptable salt thereof.

8. A process for preparing a compound of formula (I) according to claim 6, characterized in that the optional conversion of a compound of formula (I) into another compound of formula (I), is carried out by the following reaction:
   a) converting a compound of formula (I) wherein R3 is ethoxycarbonyl into a compound of formula (I) wherein R3 is aminocarbonyl by treatment with ammonium hydroxide.

9. A library of two or more compounds of formula (I):

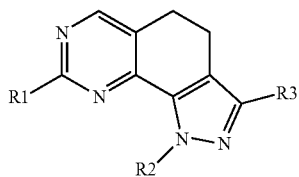

wherein
R1 is an ortho-substituted-arylamino of the formula:

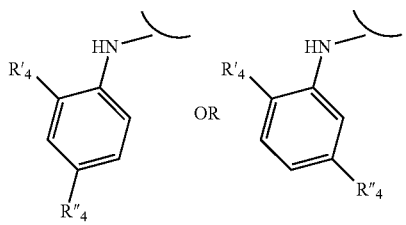

wherein $R'_4$ and $R''_4$ are independently selected from a group consisting of halogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate;

R2 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl and heterocyclyl;

R3 is CO—OR' or CO—NR'R", wherein R' and R" are, each independently, hydrogen or an optionally substituted group selected from straight or branched $C_1$-$C_6$ alkyl, $C_3$-$C_6$ cycloalkyl and heterocyclyl, or R' and R" taken together with the nitrogen atom to which they are bonded, may form an optionally substituted heterocyclyl group optionally containing one additional heteroatom selected among N, O or S;

or an isomer, tautomer, hydrate, solvate, complex, N-oxide, and a pharmaceutically acceptable salt thereof.

10. A method for treating a disease caused by and/or associated with a dysregulated protein kinase activity which comprises administering to a mammal in need thereof an effective amount of a compound of formula (I) as defined in claim 1, wherein the disease is selected from the group consisting of ovarian cancer, breast cancer, colon cancer, lung cancer, pancreatic cancer, prostate cancer, skin cancer, squamous cell carcinoma, hematopoietic tumors of lymphoid lineage, hematopoietic tumors of myeloid lineage, and tumors of the central and peripheral nervous system.

11. The method according to claim 10 further comprising subjecting the mammal in need thereof to a radiation therapy or chemotherapy regimen in combination with at least one cytostatic or cytotoxic agent.

12. The method according to claim 10 wherein the mammal in need thereof is a human.

13. A method for inhibiting the activity po PLK-1 protein which comprises contacting said protein with an effective amount of a compound as defined in claim 1.

14. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

15. A product or kit comprising a compound of formula (I) or a pharmaceutically acceptable salt thereof, as defined in claim 1, or pharmaceutical compositions comprising a therapeutically effective amount of a compound of formula (I) or a pharmaceutically acceptable salt thereof and at least one pharmaceutically acceptable excipient, carrier and/or diluents, and one or more chemotherapeutic agent, as a combined preparation for simultaneous, separate or sequential use in anticancer therapy.

16. A process for preparing a compound of formula (I) according to claim 6, characterized in that the optional conversion of a compound of formula (I) into another compound of formula (I), is carried out by the following reaction:
   h) converting a compound of formula (I) wherein R2 is an haloethyl into a compound of formula (I) wherein R2 is vinyl.

\* \* \* \* \*